(12) United States Patent
Bikard et al.

(10) Patent No.: US 11,357,831 B2
(45) Date of Patent: Jun. 14, 2022

(54) SEQUENCE-SPECIFIC ANTIMICROBIALS BY BLOCKING DNA REPAIR

(71) Applicants: INSTITUT PASTEUR, Paris (FR); ELIGO BIOSCIENCE, Paris (FR)

(72) Inventors: David Bikard, Paris (FR); Lun Cui, Paris (FR); Xavier Duportet, Paris (FR); Jesus Fernandez Rodriguez, Paris (FR)

(73) Assignees: INSTITUT PASTEUR, Paris (FR); ELIGO BIOSCIENCE, Paris (FR)

( * ) Notice: Subject to any disclaimer, the term of this patent is extended or adjusted under 35 U.S.C. 154(b) by 75 days.

(21) Appl. No.: 16/671,978

(22) Filed: Nov. 1, 2019

(65) Prior Publication Data

US 2020/0121768 A1 Apr. 23, 2020

Related U.S. Application Data

(63) Continuation of application No. 15/744,039, filed as application No. PCT/EP2016/066702 on Jul. 13, 2016, now abandoned.

(Continued)

(51) Int. Cl.
*A61K 38/46* (2006.01)
*C12N 15/10* (2006.01)
(Continued)

(52) U.S. Cl.
CPC ............ *A61K 38/465* (2013.01); *A61P 31/04* (2018.01); *C12N 1/20* (2013.01); *C12N 9/22* (2013.01);
(Continued)

(58) Field of Classification Search
None
See application file for complete search history.

(56) References Cited

U.S. PATENT DOCUMENTS

| | | | |
|---|---|---|---|
| 2003/0049841 A1* | 3/2003 | Short | C12N 15/1034 435/449 |
| 2005/0079618 A1 | 4/2005 | Court et al. | |
| 2015/0064138 A1 | 3/2015 | Lu et al. | |

FOREIGN PATENT DOCUMENTS

| | | |
|---|---|---|
| WO | 2014085698 A1 | 6/2014 |
| WO | 2014124226 A1 | 8/2014 |
| WO | 20140130922 A1 | 8/2014 |

OTHER PUBLICATIONS

Murphy KC. Lambda Gam protein inhibits the helicase and chi-stimulated recombination activities of *Escherichia coli* RecBCD enzyme. J Bacteriol. Sep. 1991; 173(18):5808-21. doi: 10.1128/jb.173.18.5808-5821.1991. PMID: 1653221; PMCID: PMC208314. (Year: 1991).*

(Continued)

*Primary Examiner* — Michelle S Horning
(74) *Attorney, Agent, or Firm* — Arrigo, Lee, Guttman & Mouta-Bellum LLP

(57) ABSTRACT

The invention relates to the improvement of endonuclease-based antimicrobials by blocking DNA repair of double-strand break(s) (DSB(s)) in prokaryotic cells. In this respect, the invention especially concerns a method involving blocking DNA repair after a nucleic acid has been submitted to DSB, in particular by a Clustered Regularly Interspaced Short Palindromic Repeats (CRISPR) associated programmable double-strand endonuclease. The invention particularly relates to the use of an exogenous molecule that inhibits DNA repair, preferably a protein that binds to the ends of the double-stranded break to block DSB repair. The invention also relates to vectors, particularly phagemids and plasmids, comprising nucleic acids encoding nucleases and Gam proteins, and a pharmaceutical composition and a product containing these vectors and their application.

18 Claims, 14 Drawing Sheets

Specification includes a Sequence Listing.

Related U.S. Application Data

(60) Provisional application No. 62/191,572, filed on Jul. 13, 2015.

(51) Int. Cl.
    *C12N 1/20*     (2006.01)
    *C12N 9/22*     (2006.01)
    *C12N 15/70*     (2006.01)
    *A61P 31/04*     (2006.01)
    *C12N 15/63*     (2006.01)

(52) U.S. Cl.
    CPC ......... *C12N 15/10* (2013.01); *C12N 15/1024* (2013.01); *C12N 15/63* (2013.01); *C12N 15/70* (2013.01); *C12N 2310/20* (2017.05); *C12N 2795/10122* (2013.01); *Y02A 50/30* (2018.01)

(56) References Cited

OTHER PUBLICATIONS

Communication Pursuant to rule 114(2) EPC, European Application No. 16741899.5, dated June 7, 2 018.
Ciu and Bikard, "Consequences of Cas9 cleavage in the chromosome of *Escherichia coli*," Nucleic Acids Research, vol. 44, No. 9, 4243-4251 (2016).
Kenan C. Murphy, Iamda Gam Protein Inhibits the Helicase and x-Stimulated Recombination Activities of *Escherichia coli* RecBCD Enzyme, Journal of Bacteriology, vol. 173, No. 18, pp. 5808-5821 (1991).
Murphy and Lewis. Properties of *Escherichia coli* expressing bacteriophage P22 Abe (anti-Rec BCD) proteins, ncluding inhibition of Chi activity. J Bacteriol. Mar. 1993; 175(6): 1756-66. (Year: 1993).
Aggarwal. Structure and function of restriction endonucleases. Curr Opin Struct Biol. Feb. 1995;5(1 ): 11-9. Review. (Year: 1995).
Sorek et al., "CRISPR-mediated adaptive immune systems in bacteria and archaea," Annual review of biochemistry 82:237-266 (2013).
Hsu et al., "Development and applications of CRISPR-Cas9 for genome engineering," Cell, 157:1262-1278 (2014).
Deltcheva et al., "CRISPR RNA maturation by trans-encoded small RNA and host factor RNase III," Nature, 471:602-607(2011).
Jinek et al., "A programmable dual-RNA-guided DNA endonuclease in adaptive bacterial immunity," Science, 337:816-821(2012).
Sternberg et al., "DNA interrogation by the CRISPR RNA-guided endonuclease Cas9," Nature, 507:62-67 (2014).
Jinek et al., "Structures of Cas9 endonucleases reveal RNA-mediated conformational activation," Science, 343 (1247997):1-28 (2014).
Jiang et al., "RNA-guided editing of bacterial genomes using CRISPR-Cas systems," Nature biotechnology, 31:233-239 (2013).
Oh et al., "CRISPR-Cas9-assisted recombineering in Lactobacillus reuteri," Nucleic acids research, 42(e131):1-11 (2014).
Cobb et al., "High-Efficiency Multiplex Genome Editing of *Streptomyces* Species Using an Engineered CRISPR/Cas System," ACS synthetic biology, 4:723-728 (2015).
Cong et al., "Multiplex genome engineering using CRISPR/Cas systems," Science, 339:819-823 (2013).
Mali et al., "RNA-guided human genome engineering via Cas9," Science, 339:823-826 (2013).
Shuman et al., "Bacterial DNA repair by non-homologous end joining," Nature reviews Microbiology, 5:852-861m (2007).
Bowater et al., "Making ends meet: repairing breaks in bacterial DNA by non-homologous end-joining," PLoS genetics 2(e8):93-99 (2006).
Citorik et al., "Sequence-specific antimicrobials using efficiently delivered RNA-guided nucleases," Nature Biotechnology, 32(11):1141-1148 (2014).

Bikard et al., "Exploiting CRISPR-Cas nucleases to produce sequence-specific antimicrobials," Nature Biotechnology, 32(11):1146-1151 (2014).
Bikard et al., "CRISPR interference can prevent natural transformation and virulence acquisition during in vivo bacterial infection," Cell Host & Microbe, 12:177-186 (2012).
Edgar et al., "The *Escherichia coli* CRISPR system protects from lambda lysogenization, lysogens, and prophage induction," Journal of Bacteriology, 192:6291-6294 (2010).
Stern et al., "Self-targeting by CRISPR: gene regulation or autoimmunity?" Trends in Genetics, 26(8):335-340 (2010).
Gomaa et al., "Programmable removal of bacterial strains by use of genome-targeting CRISPR-Cas systems," mBio, 5 (1):1-9 (2014).
Qi et al., "Repurposing CRISPR as an RNA-guided platform for sequence-specific control of gene expression," Cell, 152:1173-1183 (2013).
Bikard et al., "Programmable repression and activation of bacterial gene expression using an engineered CRISPR-Cas system," Nucleic Acids Research, 41:7429-7437 (2013).
Ton-Hoang et al., "Structuring the bacterial genome: Y1-transposases associated with REP-BIME sequences," Nucleic Acids Research, 40:3596-3609 (2012).
Kofoid et al., "Formation of an F' plasmid by recombination between imperfectly repeated chromosomal Rep sequences: a closer look at an old friend (F'(128) pro lac)," Journal of Bacteriology, 185:660-663 (2003).
Malyarchuk et al., "Expression of Mycobacterium tuberculosis Ku and Ligase D in *Escherichia coli* results in RecA and RecB-independent DNA end-joining at regions of microhomology," DNA Repair, 6:1413-1424 (2007).
Chayot et al., "An end-joining repair mechanism in *Escherichia coli*.," Proceedings of the National Academy of Sciences of the United States of America, 107:2141-2146 (2010).
Wang et al., "Genetic screens in human cells using the CRISPR-Cas9 system," Science, 343:80-84 (2014).
Shalem et al., "Genome-scale CRISPR-Cas9 knockout screening in human cells," Science, 343:84-87 (2014).
Doench et al., "Rational design of highly active sgRNAs for CRISPR-Cas9-mediated gene inactivation," Nature Biotechnology, 32:1262-1267 (2014).
Meddows et al., "RecN protein and transcription factor DksA combine to promote faithful recombinational repair of DNA double-strand breaks," Molecular Microbiology, 57:97-110 (2005).
Bieme et al., "uvrD mutations enhance tandem repeat deletion in the *Escherichia coli* chromosome via SOS induction of the RecF recombination pathway," Molecular Microbiology, 26:557-567 (1997).
Gibson et al., "Enzymatic assembly of DNA molecules up to several hundred kilobases," Nature Methods 6:343-345 (2009).
Lutz et al., "Independent and tight regulation of transcriptional units in *Escherichia coli* via the LacR/O, the TetR/O and AraC/I1-I2 regulatory elements," Nucleic Acids Research, 25:1203-1210 (1997).
Cormack et al., "FACS-optimized mutants of the green fluorescent protein (GFP)," Gene, 173:33-38 (1996).
Dole, S. T., "Characterisation of the promoter for the LexA regulated sulA gene of *Escherichia coli*. Molecular & general genetics," MGG, 189:400-404 (1983).
St-Pierre et al., "One-step cloning and chromosomal integration of DNA," ACS Synthetic Biology 2:537-541 (2013).
Makarova et al., "Evolution and classification of the CRISPR-Cas systems," Nat Rev Microbiol 9(6):467-477 (2011).
Pennisi, E., "The CRISPR craze," Science, 341(6148):833-836 (2013).
Weller G.R., "Identification of a DNA Nonhomologous End-Joining Complex in Bacteria," Science, 297, pp. 1686-1689 (2002).
Zhu et al., "Novel 3'-Ribonuclease and 3'-Phosphatase Activities of the Bacterial Non-homologous End-joining Protein, DNA Ligase D," J Biol Chem, 280:25973-25981(2005).
Gong et al., "Mechanism of nonhomologous end-joining in mycobacteria: a low-fidelity repair system driven by Ku, ligase D and ligase C," Nat Struct. Mol. Biol., 12:304-312 (2005).
Datsenko et al., "One-step inactivation of chromosomal genes in *Escherichia coli* K-12 using PCR products," PNAS, 97 (12):6640-6645 (2000).

(56) References Cited

OTHER PUBLICATIONS

Fernandez de Henestrosa A.R., "Identification of additional genes belonging to the LexA regulon in *Escherichia coli*," Molecular Microbiology, 35(6):1560-1572 (2002).
Murphy, "Properties of *Escherichia coli* Expressing Bacteriophage P22 Abe (Anti-RecBCD) Proteins, Including nhibition of Chi Activity," J Bacteriol., 175(6):1756-1766 (1993).
Di Fagagna et al., "The Gam protein of bacteriophage Mu is an orthologue of eukaryotic Ku.," Embo Reports, 4 (1):47-52 (2003).
Akroyd et al., "Localization of the Gam Gene of Bacteriophage-Mu and Characterization of the Gene-Product," Gene, 49(2):273-282 (1986).
Shee et al., "Engineered proteins detect spontaneous DNA breakage in human and bacterial cells," Elife, 2:e01222 (25 pages) (2013).
Suzman et al., "Tight Regulation, Modulation, and High-Level Expression by Vectors Containing the Arabinose PBAD Promoter," J Bacteriology, 177(14): 4121-4130 (1995).

\* cited by examiner

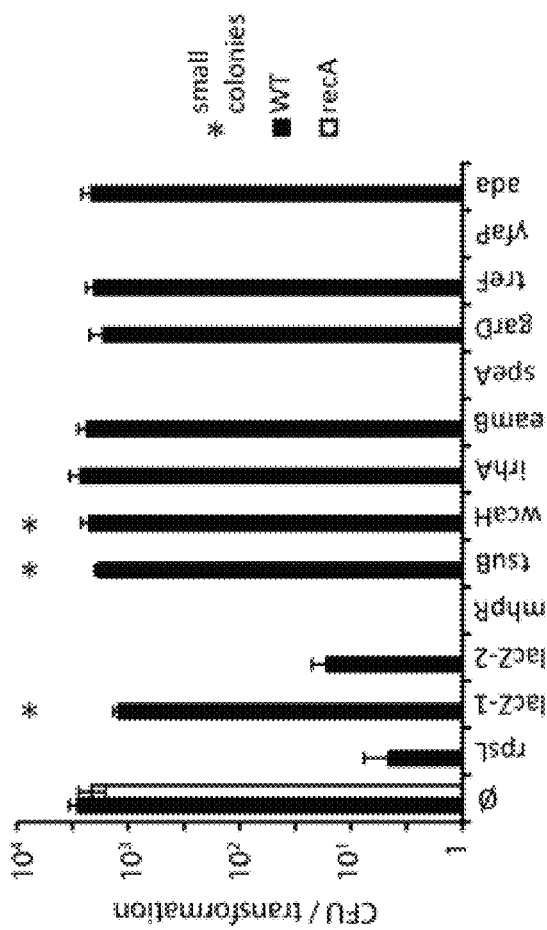
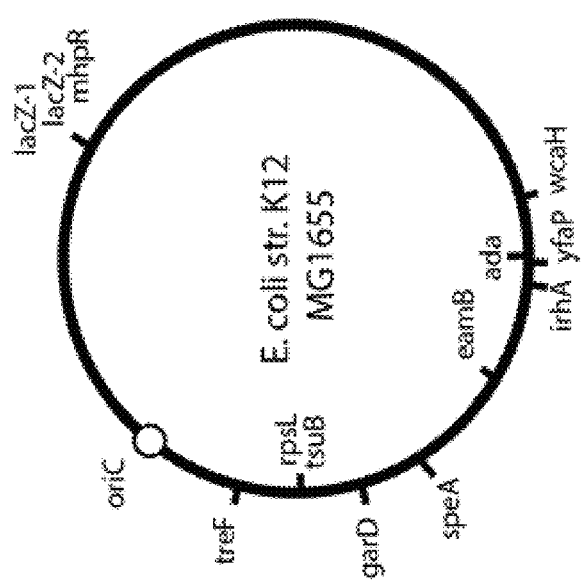
FIG. 1A
FIG. 1B

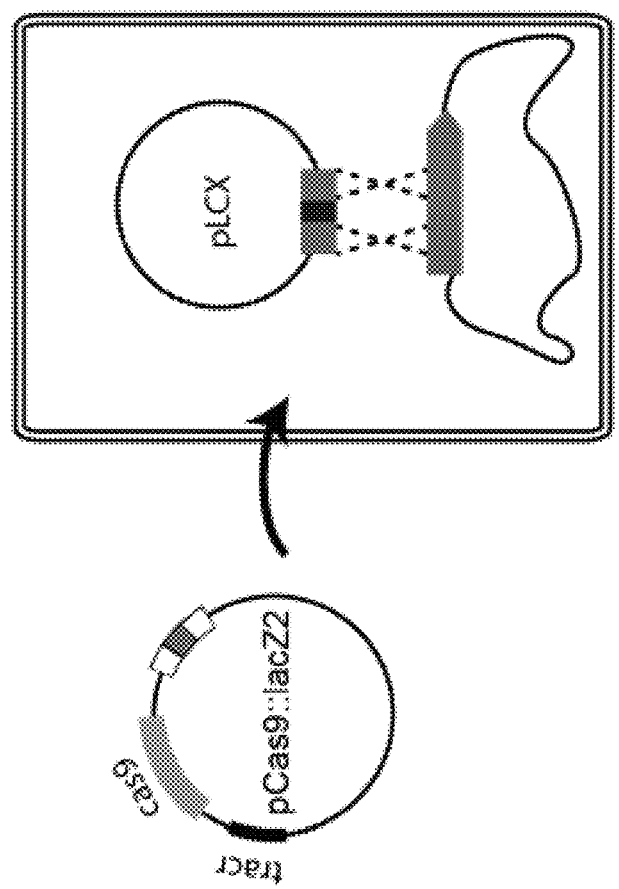
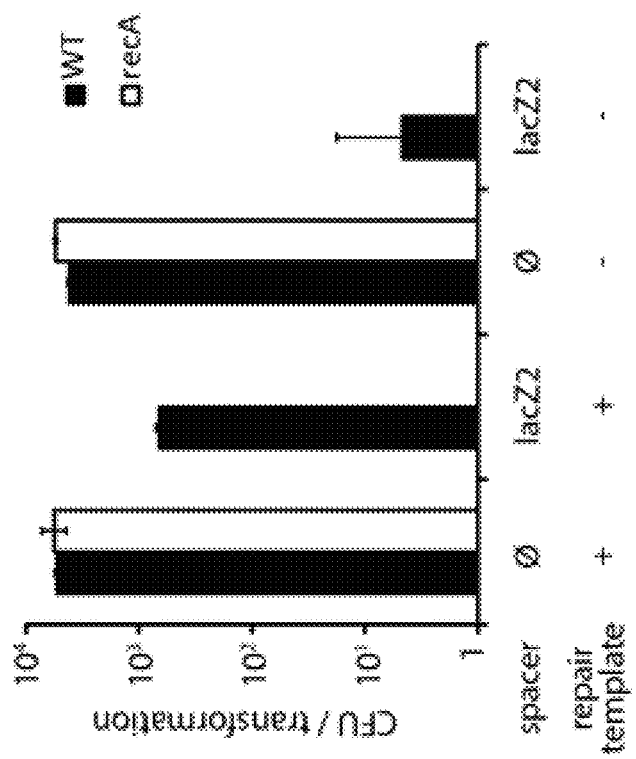
FIG. 1C
FIG. 1D

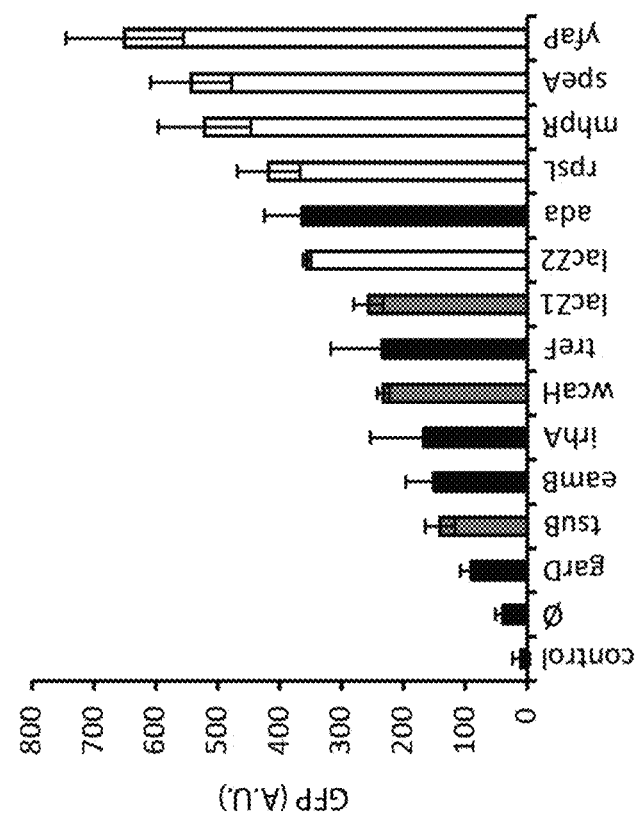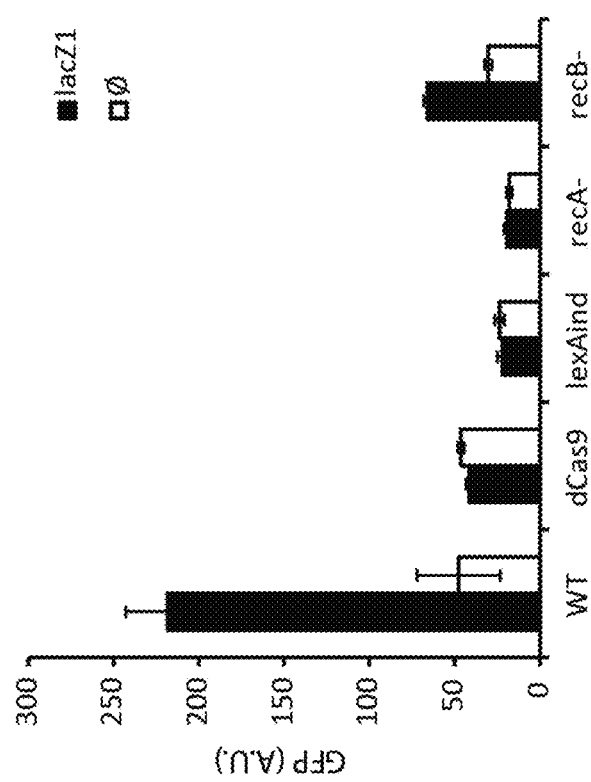
FIG. 3A  FIG. 3B  FIG. 3C

SEQUENCE LISTING

```
<160> NUMBER OF SEQ ID NOS: 72

<210> SEQ ID NO 1
<211> LENGTH: 36
<212> TYPE: DNA
<213> ORGANISM: Artificial
<220> FEATURE:
<223> OTHER INFORMATION: repeat sequence

<400> SEQUENCE: 1
gtttttgtac tctcaagatt taagtaactg tacaac                              36

<210> SEQ ID NO 2
<211> LENGTH: 36
<212> TYPE: DNA
<213> ORGANISM: Artificial
<220> FEATURE:
<223> OTHER INFORMATION: repeat sequence

<400> SEQUENCE: 2
gatataaacc taattacctc gagaggggac ggaaac                              36

<210> SEQ ID NO 3
<211> LENGTH: 36
<212> TYPE: DNA
<213> ORGANISM: Artificial
<220> FEATURE:
<223> OTHER INFORMATION: repeat sequence
```

<400> SEQUENCE: 3
gttttggaac cattcgaaac aacacagctc taaaac                         36

<210> SEQ ID NO 4
<211> LENGTH: 36
<212> TYPE: DNA
<213> ORGANISM: Artificial
<220> FEATURE:
<223> OTHER INFORMATION: repeat sequence

<400> SEQUENCE: 4
gttttagagc tatgctgttt tgaatggtcc caaaac                         36

<210> SEQ ID NO 5
<211> LENGTH: 32
<212> TYPE: DNA
<213> ORGANISM: Artificial
<220> FEATURE:
<223> OTHER INFORMATION: repeat sequence

<400> SEQUENCE: 5
atttcaatcc actcacccat gaagggtgag ac                             32

<210> SEQ ID NO 6
<211> LENGTH: 37
<212> TYPE: DNA
<213> ORGANISM: Artificial
<220> FEATURE:
<223> OTHER INFORMATION: repeat sequence

<400> SEQUENCE: 6
gtttcagtag ctagattatt tgatatactg ctgttag                        37

<210> SEQ ID NO 7
<211> LENGTH: 36
<212> TYPE: DNA
<213> ORGANISM: Artificial
<220> FEATURE:
<223> OTHER INFORMATION: repeat sequence

<400> SEQUENCE: 7
aatcagagaa taccccgtat aaaaggggac gagaac                         36

<210> SEQ ID NO 8
<211> LENGTH: 28
<212> TYPE: DNA
<213> ORGANISM: Artificial
<220> FEATURE:
<223> OTHER INFORMATION: repeat sequence

<400> SEQUENCE: 8
gttcactgcc gcacaggcag cttagaaa                                  28

<210> SEQ ID NO 9
<211> LENGTH: 37
<212> TYPE: DNA
<213> ORGANISM: Artificial
<220> FEATURE:
<223> OTHER INFORMATION: repeat sequence

<400> SEQUENCE: 9
ggttgtagct cccttcctca tttcgcagtg ctacaat                        37

<210> SEQ ID NO 10
<211> LENGTH: 28

```
<212> TYPE: DNA
<213> ORGANISM: Artificial
<220> FEATURE:
<223> OTHER INFORMATION: repeat sequence

<400> SEQUENCE: 10
ccggattccc gcctgcgcgg gaatgacg                                            28

<210> SEQ ID NO 11
<211> LENGTH: 5120
<212> TYPE: DNA
<213> ORGANISM: Artificial
<220> FEATURE:
<223> OTHER INFORMATION: pLC13

<400> SEQUENCE: 11
atcgatgcat aatgtgcctg tcaaatggac gaagcaggga ttctgcaaac cctatgctac        60
tccgtcaagc cgtcaattgt ctgattcgtt accaattatg acaacttgac ggctacatca       120 ttcactttt cttcacaacc ggcacggaac tcgctcgggc tggccccggt gcatttttta        180
aatacccgcg agaaatagag ttgatcgtca aaaccaacat tgcgaccgac ggtggcgata       240
ggcatccggt tggtgctcaa aagcagcttc gcctggctga tacgttggtc ctcgcgccag       300
cttaagacgc taatccctaa ctgctggcgg aaaagatgtg acagacgcga cggcgacaag       360
caaacatgct gtgcgacgct ggcgatatca aaattgctgt ctgccaggtg atcgctgatg       420
tactgacaag cctcgcgtac ccgattatcc atcggtggat ggagcgactc gttaatcgct       480
tccatgcgcc gcagtaacaa ttgctcaagc agatttatcg ccagcagctc cgaatagcgc       540
ccttcccctt gcccggcgtt aatgatttgc ccaaacaggt cgctgaaatg cggctggtgc       600
gcttcatccg ggcgaaagaa ccccgtattg gcaaatattg acggccagtt aagccattca       660
tgccagtagg cgcgcggacg aaagtaaacc cactggtgat accattcgcg agcctccgga       720
tgacgaccgt agtgatgaat ctctcctggc gggaacagca aaatatcacc cggtcggcaa       780
acaaattctc gtccctgatt tttcaccacc ccctgaccgc gaatggtgag attgagaata       840
taacctttca ttcccagcgg tcggtcgata aaaaaatcga gataaccgtt ggcctcaatc       900
ggcgttaaac ccgccaccag atgggcatta acgagtatc cggcagcag gggatcattt        960 tgcgcttcag ccatactttt catactcccg ccattcagag aagaaaccaa ttgtccatat      1020
tgcatcagac attgccgtca ctgcgtcttt tactggctct tctcgctaac caaaccggta      1080
accccgctta ttaaaagcat tctgtaacaa agcgggacca aagccatgac aaaaacgcgt      1140
aacaaaagtg tctataatca cggcagaaaa gtccacattg attatttgca cggcgtcaca      1200
ctttgctatg ccatagcatt tttatccata agattagcgg atcctacctg acgcttttta      1260
tcgcaactct ctactgtttc tccatacccg ttttttgggg ctagcgaatt cgagctcggt      1320
aactttaaga aggagatata ccatggctaa accagcaaaa cgtatcaaga gtgccgcagc      1380
ggcttatgtg ccacaaaacc gcgatgcggt gattaccgat attaaacgca tcggggattt      1440
acagcgcgaa gcatcacgtc tggaaacgga aatgaatgat gccatcgcgg aaattacgga      1500
gaaatttgcg gccggattg caccgattaa aaccgatatt gaaacccttt caaaaggcgt       1560
tcagggatgg tgtgaagcga accgcgacga actgacgaac ggcggcaaag tgaagacggc      1620
gaatcttgtc accggtgatg tatcgtggcg ggtccgtcca ccatcagtaa gtattcgtgg      1680
tatggatgca gtgatggaaa cgctggacg tcttggcctg caacgcttta ttcgcacgaa      1740
gcaggaaatc aacaaggaag cgattttact ggaaccgaaa gcggtcgcag gcgttgccgg      1800
```

```
aattacagtt aaatcaggca ttgaggattt ttctattatt ccatttgaac aggaagccgg   1860
tatttaattg gctgttttgg cggatgagag aagattttca gcctgataca gattaaatca   1920
gaacgcagaa gcggtctgat aaaacagaat ttgcctggcg gcagtagcgc ggtggtccca   1980
cctgacccca tgccgaactc agaagtgaaa cgccgtagcg ccgatggtag tgtggggtct   2040
ccccatgcga gagtagggaa ctgccaggca tcaaataaaa cgaaaggctc agtcgaaaga   2100
ctgggccttt cgttttatct gttgtttgtc ggtgaacgct ctcctgagta ggacaaatcc   2160
gccgggagcg gatttgaacg ttgcgaagca acggcccgga gggtggcggg caggacgccc   2220
gccataaact gccaggcatc aaattaagca gaaggccatc ctgacggatg cccttttttgc  2280 gtttctacaa actcttttgt ttattttttct aaatacattc aaatatgtat ccgctcatga   2340
gacaataacc ctgataaatg cttcaataat attgaaaaag gaagagtatg agtattcaac   2400
atttccgtgt cgcccttatt cccttttttg cggcattttg ccttcctgtt tttgctcacc   2460
cagaaacgct ggtgaaagta aaagatgctg aagatcagtt gggtgcacga gtgggttaca   2520
tcgaactgga tctcaacagc ggtaagatcc ttgagagttt cgccccgaa gaacgttttc     2580 caatgatgag cacttttaaa gttctgctat gtggcgcggt attatcccgt gttgacgccg   2640
ggcaagagca actcggtcgc cgcatacact attctcagaa tgacttggtt gagtactcac   2700
cagtcacaga aaagcatctt acggatggca tgacagtaag agaattatgc agtgctgcca   2760
taaccatgag tgataacact gcggccaact tacttctgac aacgatcgga ggaccgaagg   2820
agctaaccgc ttttttgcac aacatggggg atcatgtaac tcgccttgat cgttgggaac   2880
cggagctgaa tgaagccata ccaaacgacg agcgtgacac cacgatgcct gcagcaatgg   2940
caacaacgtt gcgcaaacta ttaactggcg aactacttac tctagcttcc cggcaacaat   3000
taatagactg gatggaggcg gataaagttg caggaccact tctgcgctcg gcccttccgg   3060
ctggctggtt tattgctgat aaatctggag ccggtgagcg tgggtctcgc ggtatcattg   3120
cagcactggg gccagatggt aagccctccc gtatcgtagt tatctacacg acggggagtc   3180
aggcaactat ggatgaacga atagacaga tcgctgagat aggtgcctca ctgattaagc      3240
attggtaact gtcagaccaa gtttactcat atatacttta gattgattta cgcgccctgt   3300
agcggcgcat taagcgcggc gggtgtggtg gttacgcgca gcgtgaccgc tacacttgcc   3360
agcgccctag cgcccgctcc tttcgctttc ttcccttcct ttctcgccac gttcgccggc   3420
tttccccgtc aagctctaaa tcgggggctc cctttagggt tccgatttag tgctttacgg   3480
cacctcgacc ccaaaaaact tgatttgggt gatggttcac gtagtgggcc atcgccctga   3540
tagacggttt ttcgcccttt gacgttggag tccacgttct ttaatagtgg actcttgttc   3600
caaacttgaa caacactcaa ccctatctcg ggctattctt ttgatttata agggattttg   3660
ccgatttcgg cctattggtt aaaaaatgag ctgatttaac aaaaatttaa cgcgaatttt   3720
aacaaaatat taacgtttac aatttaaaag gatctaggtg aagatccttt ttgataatct   3780
catgaccaaa atcccttaac gtgagttttc gttccactga gcgtcagacc ccgtagaaaa   3840
gatcaaagga tcttcttgag atcctttttt tctgcgcgta atctgctgct tgcaaacaaa   3900
aaaaccaccg ctaccagcgg tggtttgttt gccggatcaa gagctaccaa ctctttttcc   3960
gaaggtaact ggcttcagca gagcgcagat accaaatact gtccttctag tgtagccgta   4020
gttaggccac cacttcaaga actctgtagc accgcctaca tacctcgctc tgctaatcct   4080
gttaccagtg gctgctgcca gtggcgataa gtcgtgtctt accgggttgg actcaagacg   4140
atagttaccg gataaggcgc agcggtcggg ctgaacgggg ggttcgtgca cacagcccag   4200
```

```
cttggagcga acgacctaca ccgaactgag atacctacag cgtgagctat gagaaagcgc    4260
cacgcttccc gaagggagaa aggcggacag gtatccggta agcggcaggg tcggaacagg    4320
agagcgcacg agggagcttc caggggggaaa cgcctggtat ctttatagtc ctgtcgggtt    4380
tcgccacctc tgacttgagc gtcgattttt gtgatgctcg tcagggggc ggagcctatg    4440 gaaaaacgcc agcaacgcgg ccttttttacg gttcctggcc ttttgctggc cttttgctca    4500
catgttcttt cctgcgttat cccctgattc tgtggataac cgtattaccg cctttgagtg    4560
agctgatacc gctcgccgca gccgaacgac cgagcgcagc gagtcagtga gcgaggaagc    4620
ggaagagcgc ctgatgcggt attttctcct tacgcatctg tgcggtattt cacaccgcat    4680
atggtgcact ctcagtacaa tctgctctga tgccgcatag ttaagccagt atacactccg    4740
ctatcgctac gtgactgggt catggctgcg ccccgacacc cgccaacacc cgctgacgcg    4800
ccctgacggg cttgtctgct cccggcatcc gcttacagac aagctgtgac cgtctccggg    4860
agctgcatgt gtcagaggtt ttcaccgtca tcaccgaaac gcgcgaggca gcaaggagat    4920
ggcgcccaac agtcccccgg ccacggggcc tgccaccata cccacgccga aacaagcgct    4980
catgagcccg aagtggcgag cccgatcttc cccatcggtg atgtcggcga tataggcgcc    5040
agcaaccgca cctgtggcgc cggtgatgcc ggccacgatg cgtccggcgt agaggatctg    5100
ctcatgtttg acagcttatc                                                5120

<210> SEQ ID NO 12
<211> LENGTH: 30
<212> TYPE: DNA
<213> ORGANISM: Artificial
<220> FEATURE:
<223> OTHER INFORMATION: primer LC2

<400> SEQUENCE: 12
ccttcttaaa gttaccgagc tcgaattcgc                                        30

<210> SEQ ID NO 13
<211> LENGTH: 60
<212> TYPE: DNA
<213> ORGANISM: Artificial
<220> FEATURE:
<223> OTHER INFORMATION: primer LC296

<400> SEQUENCE: 13
tatattttag gaattctaaa gatctttgac agctagctca gtcctaggta taatactagt       60

<210> SEQ ID NO 14
<211> LENGTH: 39
<212> TYPE: DNA
<213> ORGANISM: Artificial
<220> FEATURE:
<223> OTHER INFORMATION: primer LC397

<400> SEQUENCE: 14
atccgccaaa acagccaatt aaataccggc ttcctgttc                              39

<210> SEQ ID NO 15
<211> LENGTH: 61
<212> TYPE: DNA
<213> ORGANISM: Artificial
<220> FEATURE:
<223> OTHER INFORMATION: primer LC398

<400> SEQUENCE: 15
```
gcgaattcga gctcggtaac tttaagaagg agatatacca tggctaaacc agcaaaacgt    60
a                                                                    61

<210> SEQ ID NO 16
<211> LENGTH: 30
<212> TYPE: DNA
<213> ORGANISM: Artificial
<220> FEATURE:
<223> OTHER INFORMATION: CRISPR spacer LacZ1

<400> SEQUENCE: 16
tcactggccg tcgttttaca acgtcgtgac                                     30

<210> SEQ ID NO 17
<211> LENGTH: 30
<212> TYPE: DNA
<213> ORGANISM: Artificial
<220> FEATURE:
<223> OTHER INFORMATION: CRISPR spacer LacZ2

<400> SEQUENCE: 17
ccattacggt caatccgccg tttgttccca                                     30

<210> SEQ ID NO 18
<211> LENGTH: 30
<212> TYPE: DNA
<213> ORGANISM: Artificial
<220> FEATURE:
<223> OTHER INFORMATION: CRISPR spacer rpsL

<400> SEQUENCE: 18
tactttacgc agcgcggagt tcggtttttt                                     30

<210> SEQ ID NO 19
<211> LENGTH: 30
<212> TYPE: DNA
<213> ORGANISM: Artificial
<220> FEATURE:
<223> OTHER INFORMATION: CRISPR spacer mhpR

<400> SEQUENCE: 19
ggaattaatc gaaatgttag cctcccgccc                                     30

<210> SEQ ID NO 20
<211> LENGTH: 30
<212> TYPE: DNA
<213> ORGANISM: Artificial
<220> FEATURE:
<223> OTHER INFORMATION: CRISPR spacer tsuB

<400> SEQUENCE: 20
taaggtcttc gttcagggca tagaccttaa                                     30

<210> SEQ ID NO 21
<211> LENGTH: 30
<212> TYPE: DNA
<213> ORGANISM: Artificial
<220> FEATURE:
<223> OTHER INFORMATION: CRISPR spacer wcaH

<400> SEQUENCE: 21
ttttctcgct gagaagcgta ccggagtacc                                     30

<210> SEQ ID NO 22
<211> LENGTH: 30

```
<212> TYPE: DNA
<213> ORGANISM: Artificial
<220> FEATURE:
<223> OTHER INFORMATION: CRISPR spacer irhA

<400> SEQUENCE: 22
attccgctgc gcagtaccag tgtgttggcg                                   30

<210> SEQ ID NO 23
<211> LENGTH: 30
<212> TYPE: DNA
<213> ORGANISM: Artificial
<220> FEATURE:
<223> OTHER INFORMATION: CRISPR spacer eamB

<400> SEQUENCE: 23
cagcggtaca cctttttgagt tgggcggggg                                  30

<210> SEQ ID NO 24
<211> LENGTH: 30
<212> TYPE: DNA
<213> ORGANISM: Artificial
<220> FEATURE:
<223> OTHER INFORMATION: CRISPR spacer speA

<400> SEQUENCE: 24
agcagaacgt ctgaatgtcg ttcctcgtct                                   30

<210> SEQ ID NO 25
<211> LENGTH: 30
<212> TYPE: DNA
<213> ORGANISM: Artificial
<220> FEATURE:
<223> OTHER INFORMATION: CRISPR spacer garD

<400> SEQUENCE: 25
cgtggtgggg ctgaatcatt tgtacggttg                                   30

<210> SEQ ID NO 26
<211> LENGTH: 30
<212> TYPE: DNA
<213> ORGANISM: Artificial
<220> FEATURE:
<223> OTHER INFORMATION: CRISPR spacer treF

<400> SEQUENCE: 26
gtaccgcgat ttacgcgcgg gggcggcctc                                   30

<210> SEQ ID NO 27
<211> LENGTH: 30
<212> TYPE: DNA
<213> ORGANISM: Artificial
<220> FEATURE:
<223> OTHER INFORMATION: CRISPR spacer yfaP

<400> SEQUENCE: 27
attcgtgcac gtttacggct ggttctctcg                                   30

<210> SEQ ID NO 28
<211> LENGTH: 30
<212> TYPE: DNA
<213> ORGANISM: Artificial
<220> FEATURE:
<223> OTHER INFORMATION: CRISPR spacer ada

<400> SEQUENCE: 28
```
ggtgcgttac gcgctggctg attgtgagct                                        30

<210> SEQ ID NO 29
<211> LENGTH: 33
<212> TYPE: DNA
<213> ORGANISM: Artificial
<220> FEATURE:
<223> OTHER INFORMATION: primer B299

<400> SEQUENCE: 29
catgaattca actcaacaag tctcagtgtg ctg                                    33

<210> SEQ ID NO 30
<211> LENGTH: 40
<212> TYPE: DNA
<213> ORGANISM: Artificial
<220> FEATURE:
<223> OTHER INFORMATION: primer LC34

<400> SEQUENCE: 30
tttaggcgct gccatcttaa gacgaaaggg cctcgtgata                             40

<210> SEQ ID NO 31
<211> LENGTH: 63
<212> TYPE: DNA
<213> ORGANISM: Artificial
<220> FEATURE:
<223> OTHER INFORMATION: primer LC35

<400> SEQUENCE: 31
ttcagcacac tgagacttgt tgagttgaat tcatgagtat taagtattgt tttatggctg       60
ata                                                                     63

<210> SEQ ID NO 32
<211> LENGTH: 40
<212> TYPE: DNA
<213> ORGANISM: Artificial
<220> FEATURE:
<223> OTHER INFORMATION: primer LC36

<400> SEQUENCE: 32
tatcacgagg ccctttcgtc ttaagatggc agcgcctaaa                             40

<210> SEQ ID NO 33
<211> LENGTH: 37
<212> TYPE: DNA
<213> ORGANISM: Artificial
<220> FEATURE:
<223> OTHER INFORMATION: primer LC41

<400> SEQUENCE: 33
tgcagcgcga tcgtaatcag gatcccatgg tacgcgt                                37

<210> SEQ ID NO 34
<211> LENGTH: 37
<212> TYPE: DNA
<213> ORGANISM: Artificial
<220> FEATURE:
<223> OTHER INFORMATION: primer LC42

<400> SEQUENCE: 34
acagaactta atgggcccga agacgaaagg gcctcgt                                37

<210> SEQ ID NO 35
<211> LENGTH: 40

```
<212> TYPE: DNA
<213> ORGANISM: Artificial
<220> FEATURE:
<223> OTHER INFORMATION: primer LC37

<400> SEQUENCE: 35
tccgccgttt gttcccacgt agaatccgac gggttgttac                              40

<210> SEQ ID NO 36
<211> LENGTH: 40
<212> TYPE: DNA
<213> ORGANISM: Artificial
<220> FEATURE:
<223> OTHER INFORMATION: primer LC38

<400> SEQUENCE: 36
gtaacaaccc gtcggattct acgtgggaac aaacggcgga                              40

<210> SEQ ID NO 37
<211> LENGTH: 37
<212> TYPE: DNA
<213> ORGANISM: Artificial
<220> FEATURE:
<223> OTHER INFORMATION: primer LC39

<400> SEQUENCE: 37
acgaggccct ttcgtcttcg ggcccattaa gttctgt                                 37

<210> SEQ ID NO 38
<211> LENGTH: 37
<212> TYPE: DNA
<213> ORGANISM: Artificial
<220> FEATURE:
<223> OTHER INFORMATION: primer LC40

<400> SEQUENCE: 38
acgcgtacca tgggatcctg attacgatcg cgctgca                                 37

<210> SEQ ID NO 39
<211> LENGTH: 19
<212> TYPE: DNA
<213> ORGANISM: Artificial
<220> FEATURE:
<223> OTHER INFORMATION: primer LC191

<400> SEQUENCE: 39
gtctagggcg gcggatttg                                                     19

<210> SEQ ID NO 40
<211> LENGTH: 22
<212> TYPE: DNA
<213> ORGANISM: Artificial
<220> FEATURE:
<223> OTHER INFORMATION: primer LC192

<400> SEQUENCE: 40
cgctctcctg agtaggacaa at                                                 22

<210> SEQ ID NO 41
<211> LENGTH: 36
<212> TYPE: DNA
<213> ORGANISM: Artificial
<220> FEATURE:
<223> OTHER INFORMATION: primer LC193

<400> SEQUENCE: 41
```
acaattgaat accgatcggc ctcgtgatac gcctat                                36

<210> SEQ ID NO 42
<211> LENGTH: 42
<212> TYPE: DNA
<213> ORGANISM: Artificial
<220> FEATURE:
<223> OTHER INFORMATION: primer LC194

<400> SEQUENCE: 42
ataggcgtat cacgaggccg atcggtattc aattgtgccc aa                         42

<210> SEQ ID NO 43
<211> LENGTH: 41
<212> TYPE: DNA
<213> ORGANISM: Artificial
<220> FEATURE:
<223> OTHER INFORMATION: primer LC195

<400> SEQUENCE: 43 cagggggctgg attgattatg agtaaaggag aagaactttt c                         41

<210> SEQ ID NO 44
<211> LENGTH: 38
<212> TYPE: DNA
<213> ORGANISM: Artificial
<220> FEATURE:
<223> OTHER INFORMATION: primer LC196

<400> SEQUENCE: 44
ttcttctcct ttactcataa tcaatccagc ccctgtga                              38

<210> SEQ ID NO 45
<211> LENGTH: 42
<212> TYPE: DNA
<213> ORGANISM: Artificial
<220> FEATURE:
<223> OTHER INFORMATION: primer LC95

<400> SEQUENCE: 45
ctccgacgcc gaacccatac aacctcctta gtacatcaag ca                         42

<210> SEQ ID NO 46
<211> LENGTH: 58
<212> TYPE: DNA
<213> ORGANISM: Artificial
<220> FEATURE:
<223> OTHER INFORMATION: primer LC96

<400> SEQUENCE: 46
gcaggacgcc cgccataaac tgccaggaat tggggatcgg ggggttccgc gcacattt        58

<210> SEQ ID NO 47
<211> LENGTH: 58
<212> TYPE: DNA
<213> ORGANISM: Artificial
<220> FEATURE:
<223> OTHER INFORMATION: primer LC94

<400> SEQUENCE: 47
gcaggacgcc cgccataaac tgccaggaat tggggatcgg ggggttccgc gcacattt        58

<210> SEQ ID NO 48
<211> LENGTH: 59
<212> TYPE: DNA
<213> ORGANISM: Artificial

```
<220> FEATURE:
<223> OTHER INFORMATION: primer LC98

<400> SEQUENCE: 48
agtttaggtt aggcgccatg catctcgagg catgcctgca tcattcgcgc accacctca      59

<210> SEQ ID NO 49
<211> LENGTH: 42
<212> TYPE: DNA
<213> ORGANISM: Artificial
<220> FEATURE:
<223> OTHER INFORMATION: primer LC93

<400> SEQUENCE: 49
cgtccaaatg gctcgcatac aacctcctta gtacatcaag ca                        42

<210> SEQ ID NO 50
<211> LENGTH: 42
<212> TYPE: DNA
<213> ORGANISM: Artificial
<220> FEATURE:
<223> OTHER INFORMATION: primer LC92

<400> SEQUENCE: 50
tgcttgatgt actaaggagg ttgtatgcga gccatttgga cg                        42

<210> SEQ ID NO 51
<211> LENGTH: 58
<212> TYPE: DNA
<213> ORGANISM: Artificial
<220> FEATURE:
<223> OTHER INFORMATION: primer LC97

<400> SEQUENCE: 51
agtttaggtt aggcgccatg catctcgagg catgcctgca tcacggaggc gttgggac       58

<210> SEQ ID NO 52
<211> LENGTH: 64
<212> TYPE: DNA
<213> ORGANISM: Artificial
<220> FEATURE:
<223> OTHER INFORMATION: primer LC100

<400> SEQUENCE: 52
gcaggacgcc cgccataaac tgccaggaat tggggatcgg ttaagaccca ctttcacatt     60
taag                                                                  64

<210> SEQ ID NO 53
<211> LENGTH: 59
<212> TYPE: DNA
<213> ORGANISM: Artificial
<220> FEATURE:
<223> OTHER INFORMATION: primer LC101

<400> SEQUENCE: 53
agtttaggtt aggcgccatg catctcgagg catgcctgca tataaacgca gaaaggccc      59

<210> SEQ ID NO 54
<211> LENGTH: 18
<212> TYPE: DNA
<213> ORGANISM: Artificial
<220> FEATURE:
<223> OTHER INFORMATION: primer LC33

<400> SEQUENCE: 54
```

-continued

```
gactggaaag cgggcagt                                                     18

<210> SEQ ID NO 55
<211> LENGTH: 20
<212> TYPE: DNA
<213> ORGANISM: Artificial
<220> FEATURE:
<223> OTHER INFORMATION: primer LC47

<400> SEQUENCE: 55
cgcacgatag agattcggga                                                   20

<210> SEQ ID NO 56
<211> LENGTH: 20
<212> TYPE: DNA
<213> ORGANISM: Artificial
<220> FEATURE:
<223> OTHER INFORMATION: primer LC80

<400> SEQUENCE: 56
tcaggcggga tgaagatgat                                                   20

<210> SEQ ID NO 57
<211> LENGTH: 21
<212> TYPE: DNA
<213> ORGANISM: Artificial
<220> FEATURE:
<223> OTHER INFORMATION: primer LC153

<400> SEQUENCE: 57
gctgggatac gctggtgttt a                                                 21

<210> SEQ ID NO 58
<211> LENGTH: 19
<212> TYPE: DNA
<213> ORGANISM: Artificial
<220> FEATURE:
<223> OTHER INFORMATION: primer LC154

<400> SEQUENCE: 58
cacagcgcaa ggacgttga                                                    19

<210> SEQ ID NO 59
<211> LENGTH: 18
<212> TYPE: DNA
<213> ORGANISM: Artificial
<220> FEATURE:
<223> OTHER INFORMATION: primer LC155

<400> SEQUENCE: 59
acacaacatg acgggctt                                                     18

<210> SEQ ID NO 60
<211> LENGTH: 9326
<212> TYPE: DNA
<213> ORGANISM: Artificial
<220> FEATURE:
<223> OTHER INFORMATION: pCas9 (pCas9-a)
<220> FEATURE:
<221> NAME/KEY: gene
<222> LOCATION: (219)..(8886)
<223> OTHER INFORMATION: gene cat - positions are given on the
      complementary strand : complement (8886..219)
<220> FEATURE:
<221> NAME/KEY: promoter
<222> LOCATION: (220)..(322)
<223> OTHER INFORMATION: cat promoter - positions are given on the
      complementary strand : complement (220..322)
```

```
<220> FEATURE:
<221> NAME/KEY: rep_origin
<222> LOCATION: (848)..(1393)
<223> OTHER INFORMATION: p15A ori - positions are given on the
      complementary strand : complement (848..1393)
<220> FEATURE:
<221> NAME/KEY: promoter
<222> LOCATION: (1505)..(1533)
<223> OTHER INFORMATION: tet promoter
<220> FEATURE:
<221> NAME/KEY: misc_feature
<222> LOCATION: (1844)..(2014)
<223> OTHER INFORMATION: tracrRNA sequence of S. p (Zhangfeng) -
      positions are given on the complementary strand : complement
      (1844..2014)
<220> FEATURE:
<221> NAME/KEY: misc_feature
<222> LOCATION: (1846)..(1932)
<223> OTHER INFORMATION: tracrRNA sequence of S. p (Zhangfeng)
<220> FEATURE:
<221> NAME/KEY: gene
<222> LOCATION: (2225)..(6331)
<223> OTHER INFORMATION: Cas9 (Csn1) endonuclease from the streptococcus
      pyogenes Type II CRISPR/Cas system
<220> FEATURE:
<221> NAME/KEY: misc_feature
<222> LOCATION: (6484)..(6519)
<223> OTHER INFORMATION: repeat
<220> FEATURE:
<221> NAME/KEY: misc_feature
<222> LOCATION: (6550)..(6585)
<223> OTHER INFORMATION: repeat

<400> SEQUENCE: 60
gaattccgga tgagcattca tcaggcgggc aagaatgtga ataaaggccg gataaaactt      60
gtgcttattt ttctttacgg tctttaaaaa ggccgtaata tccagctgaa cggtctggtt     120
ataggtacat tgagcaactg actgaaatgc ctcaaaatgt tctttacgat gccattggga     180
tatatcaacg gtggtatatc cagtgatttt tttctccatt ttagcttcct tagctcctga     240
aaatctcgat aactcaaaaa atacgcccgg tagtgatctt atttcattat ggtgaaagtt     300
ggaacctctt acgtgccgat caacgtctca ttttcgccaa aagttggccc agggcttccc     360
ggtatcaaca gggacaccag gatttattta ttctgcgaag tgatcttccg tcacaggtat     420
ttattcggcg caaagtgcgt cgggtgatgc tgccaactta ctgatttagt gtatgatggt     480
gtttttgagg tgctccagtg gcttctgttt ctatcagctg tccctcctgt tcagctactg     540
acggggtggt gcgtaacggc aaaagcaccg ccggacatca gcgctagcgg agtgtatact     600
ggcttactat gttggcactg atgagggtgt cagtgaagtg cttcatgtgg caggagaaaa     660
aaggctgcac cggtgcgtca gcagaatatg tgatacagga tatattccgc ttcctcgctc     720
actgactcgc tacgctcggt cgttcgactg cggcgagcgg aaatggctta cgaacggggc     780
ggagatttcc tggaagatgc caggaagata cttaacaggg aagtgagagg gccgcggcaa     840
agccgttttt ccataggctc cgcccccctg acaagcatca cgaaatctga cgctcaaatc     900
agtggtggcg aaacccgaca ggactataaa gataccaggc gtttccccct ggcggctccc     960
tcgtgcgctc tcctgttcct gcctttcggt ttaccggtgt cattccgctg ttatggccgc    1020
gtttgtctca ttccacgcct gacactcagt tccgggtagg cagttcgctc caagctggac    1080
tgtatgcacg aaccccccgt tcagtccgac cgctgcgcct tatccggtaa ctatcgtctt    1140
gagtccaacc cggaaagaca tgcaaaagca ccactggcag cagccactgg taattgattt    1200
agaggagtta gtcttgaagt catgcgccgg ttaaggctaa actgaaagga caagttttgg    1260
tgactgcgct cctccaagcc agttacctcg gttcaaagag ttggtagctc agagaacctt    1320
```

```
cgaaaaaccg ccctgcaagg cggttttttc gttttcagag caagagatta cgcgcagacc      1380
aaaacgatct caagaagatc atcttattaa tcagataaaa tatttctaga tttcagtgca      1440
atttatctct tcaaatgtag cacctgaagt cagccccata cgatataagt tgtaattctc      1500
atgtttgaca gcttatcatc gataagcttt aatgcggtag tttatcacag ttaaattgct      1560
aacgcagtca ggcaccgtgt atgaaatcta acaatgcgct catcgtcatc ctcggcaccg      1620
tcaccctgga tgctgtaggc ataggcttgg ttatgccggt actgccgggc ctcttgcggg      1680
attacgaaat catcctgtgg agcttagtag gtttagcaag atggcagcgc ctaaatgtag      1740
aatgataaaa ggattaagag attaatttcc ctaaaaatga taaacaagc gttttgaaag       1800 cgcttgtttt tttggtttgc agtcagagta gaatagaagt atcaaaaaaa gcaccgactc      1860
ggtgccactt tttcaagttg ataacggact agccttattt taacttgcta tgctgttttg      1920
aatggttcca acaagattat tttataactt ttataacaaa taatcaagga gaaattcaaa      1980
gaaatttatc agccataaaa caatacttaa tactatagaa tgataacaaa ataaactact      2040
ttttaaaaga attttgtgtt ataatctatt tattattaag tattgggtaa tatttttga      2100 agagatattt tgaaaagaa aaattaaagc atattaaact aatttcggag gtcattaaaa       2160
ctattattga aatcatcaaa ctcattatgg atttaattta aactttttat tttaggaggc      2220
aaaaatggat aagaaatact caataggctt agatatcggc acaaatagcg tcggatgggc      2280
ggtgatcact gatgaatata aggttccgtc taaaaagttc aaggttctgg aaatacaga      2340 ccgccacagt atcaaaaaaa atcttatagg ggctctttta tttgacagtg gagagacagc      2400
ggaagcgact cgtctcaaac ggacagctcg tagaaggtat acacgtcgga gaatcgtat       2460 ttgttatcta caggagattt tttcaaatga gatggcgaaa gtagatgata gtttctttca     2520
tcgacttgaa gagtcttttt tggtggaaga agacaagaag catgaacgtc atcctatttt     2580
tggaaatata gtagatgaag ttgcttatca tgagaaatat ccaactatct atcatctgcg     2640
aaaaaaattg gtagattcta ctgataaagc ggatttgcgc ttaatctatt tggccttagc     2700
gcatatgatt aagtttcgtg gtcatttttt gattgaggga gatttaaatc ctgataatag     2760
tgatgtggac aaactatttt ccagttggt acaaacctac aatcaattat ttgaagaaaa      2820
ccctattaac gcaagtggag tagatgctaa agcgattctt tctgcacgat tgagtaaatc     2880
aagacgatta gaaaatctca ttgctcagct ccccggtgag aagaaaaatg cttatttgg      2940 gaatctcatt gctttgtcat tgggtttgac ccctaatttt aaatcaaatt ttgatttggc     3000
agaagatgct aaattacagc tttcaaaaga tacttacgat gatgatttag ataatttatt     3060
ggcgcaaatt ggagatcaat atgctgattt gttttttggca gctaagaatt tatcagatgc     3120 tatttttactt tcagatatcc taagagtaaa tactgaaata actaaggctc ccctatcagc    3180
ttcaatgatt aaacgctacg atgaacatca tcaagacttg actcttttaa aagctttagt    3240
tcgacaacaa cttccagaaa agtataaaga aatctttttt gatcaatcaa aaaacggata    3300
tgcaggttat attgatgggg gagctagcca agaagaattt tataaattta tcaaaccaat    3360
tttagaaaaa atggatggta ctgaggaatt attggtgaaa ctaaatcgtg aagatttgct    3420
gcgcaagcaa cggacctttg acaacggctc tattccccat caaattcact tgggtgagct    3480
gcatgctatt ttgagaagac aagaagactt ttatccattt ttaaaagaca atcgtgagaa    3540
gattgaaaaa atcttgactt ttcgaattcc ttattatgtt ggtccattgg cgcgtggcaa    3600
tagtcgtttt gcatggatga ctcggaagtc tgaagaaaca attaccccat ggaatttga    3660 agaagttgtc gataaaggtg cttcagctca atcatttatt gaacgcatga caaactttga    3720
```

```
taaaaatctt ccaaatgaaa aagtactacc aaaacatagt ttgctttatg agtattttac    3780
ggtttataac gaattgacaa aggtcaaata tgttactgaa ggaatgcgaa aaccagcatt    3840
tctttcaggt gaacagaaga aagccattgt tgatttactc ttcaaaacaa atcgaaaagt    3900
aaccgttaag caattaaaag aagattattt caaaaaaata gaatgttttg atagtgttga    3960
aatttcagga gttgaagata gatttaatgc ttcattaggt acctaccatg atttgctaaa    4020
aattattaaa gataaagatt ttttggataa tgaagaaaat gaagatatct tagaggatat    4080
tgttttaaca ttgaccttat ttgaagatag ggagatgatt gaggaaagac ttaaaacata    4140
tgctcacctc tttgatgata aggtgatgaa acagcttaaa cgtcgccgtt atactggttg    4200
gggacgtttg tctcgaaaat tgattaatgg tattagggat aagcaatctg gcaaaacaat    4260
attagatttt ttgaaatcag atggttttgc caatcgcaat tttatgcagc tgatccatga    4320
tgatagtttg acatttaaag aagacattca aaaagcacaa gtgtctggac aaggcgatag    4380
tttacatgaa catattgcaa atttagctgg tagccctgct attaaaaaag gtattttaca    4440
gactgtaaaa gttgttgatg aattggtcaa agtaatgggg cggcataagc cagaaaatat    4500
cgttattgaa atggcacgtg aaaatcagac aactcaaaag ggccagaaaa attcgcgaga    4560
gcgtatgaaa cgaatcgaag aaggtatcaa agaattagga agtcagattc ttaaagagca    4620
tcctgttgaa aatactcaat tgcaaaatga aaagctctat ctctattatc tccaaaatgg    4680
aagagacatg tatgtggacc aagaattaga tattaatcgt ttaagtgatt atgatgtcga    4740
tcacattgtt ccacaaagtt tccttaaaga cgattcaata gacaataagg tcttaacgcg    4800
ttctgataaa aatcgtggta atcggataaa cgttccaagt gaagaagtag tcaaaaagat    4860
gaaaaactat tggagacaac ttctaaacgc caagttaatc actcaacgta agtttgataa    4920
tttaacgaaa gctgaacgtg gaggtttgag tgaacttgat aaagctggtt ttatcaaacg    4980
ccaattggtt gaaactcgcc aaatcactaa gcatgtggca caaattttgg atagtcgcat    5040
gaatactaaa tacgatgaaa atgataaact tattcgagag gttaaagtga ttaccttaaa    5100
atctaaatta gtttctgact tccgaaaaga tttccaattc tataaagtac gtgagattaa    5160
caattaccat catgcccatg atgcgtatct aaatgccgtc gttggaactg ctttgattaa    5220
gaaatatcca aaacttgaat cggagtttgt ctatggtgat tataaagttt atgatgttcg    5280
taaaatgatt gctaagtctg agcaagaaat aggcaaagca accgcaaaat atttctttta    5340
ctctaatatc atgaacttct tcaaaacaga aattacactt gcaaatggag agattcgcaa    5400
acgccctcta atcgaaacta atggggaaac tggagaaatt gtctgggata agggcgaga     5460 ttttgccaca gtgcgcaaag tattgtccat gccccaagtc aatattgtca agaaaacaga    5520
agtacagaca ggcggattct ccaaggagtc aattttacca aaaagaaatt cggacaagct    5580
tattgctcgt aaaaaagact gggatccaaa aaaatatggt ggttttgata gtccaacggt    5640
agcttattca gtcctagtgg ttgctaaggt ggaaaaaggg aaatcgaaga agttaaaatc    5700
cgttaaagag ttactaggga tcacaattat ggaaagaagt tcctttgaaa aaaatccgat    5760 tgactttta gaagctaaag gatataagga agttaaaaaa gacttaatca ttaaactacc    5820
taaatatagt cttttgagt tagaaaacgg tcgtaaacgg atgctggcta gtgccggaga    5880
attacaaaaa ggaaatgagc tggctctgcc aagcaaatat gtgaattttt tatatttagc    5940
tagtcattat gaaaagttga agggtagtcc agaagataac gaacaaaaac aattgtttgt    6000
ggagcagcat aagcattatt tagatgagat tattgagcaa atcagtgaat tttctaagcg    6060
```

```
tgttatttta gcagatgcca atttagataa agttcttagt gcatataaca aacatagaga   6120
caaaccaata cgtgaacaag cagaaaatat tattcattta tttacgttga cgaatcttgg   6180
agctcccgct gcttttaaat attttgatac aacaattgat cgtaaacgat atacgtctac   6240
aaaagaagtt ttagatgcca ctcttatcca tcaatccatc actggtcttt atgaaacacg   6300
cattgatttg agtcagctag gaggtgactg aagtatattt tagatgaaga ttatttctta   6360
ataactaaaa atatggtata atactcttaa taaatgcagt aatacagggg cttttcaaga   6420
ctgaagtcta gctgagacaa atagtgcgat tacgaaattt tttagacaaa aatagtctac   6480
gaggttttag agctatgctg ttttgaatgg tcccaaaact gagaccagtc tcggaagctc   6540
aaaggtctcg ttttagagct atgctgtttt gaatggtccc aaaacttcag cacactgaga   6600
cttgttgagt ccatgttttt agagctatgc tgttttgaat ggactccatt caacattgcc   6660
gatgataact tgagaaagag ggttaatacc agcagtcgga taccttccta ttctttctgt   6720
taaagcgttt tcatgttata ataggcaaaa gaagagtagt gtgatcgtcc attccgacag   6780
catcgccagt cactatggcg tgctgctagc gctatatgcg ttgatgcaat ttctatgcgc   6840
acccgttctc ggagcactgt ccgaccgctt tggccgccgc ccagtcctgc tcgcttcgct   6900
acttggagcc actatcgact acgcgatcat ggcgaccaca cccgtcctgt ggatcctcta   6960
cgccggacgc atcgtggccg gcatcaccgg cgccacaggt gcggttgctg gcgcctatat   7020
cgccgacatc accgatgggg aagatcgggc tcgccacttc gggctcatga gcgcttgttt   7080
cggcgtgggt atggtggcag gccccgtggc cggggactg ttgggcgcca ctcccttgca   7140
tgcaccattc cttgcggcgg cggtgctcaa cggcctcaac ctactactgg gctgcttcct   7200
aatgcaggag tcgcataagg gagagcgtcg accgatgccc ttgagagcct caacccagt   7260 cagctccttc cggtgggcgc ggggcatgac tatcgtcgcc gcacttatga ctgtcttctt   7320
tatcatgcaa ctcgtaggac aggtgccggc agcgctctgg gtcattttcg gcgaggaccg   7380
cttccgctgg agcgcgacga tgatcggcct gtcgcttgcg gtattcggaa tcttgcacgc   7440
cctcgctcaa gccttcgtca ctggtcccgc caccaaacgt ttcggcgaga gcaggccat   7500 tatcgccggc atggcggccg acgcgctggg ctacgtcttg ctggcgttcg cgacgcgagg   7560
ctggatggcc ttccccatta tgattcttct cgcttccggc ggcatcggga tgcccgcgtt   7620
gcaggccatg ctgtccaggc aggtagatga cgaccatcag gacagcttc aaggatcgct   7680 cgcggctctt accagcctaa cttcgatcat tggaccgctg atcgtcacgg cgatttatgc   7740
cgcctcggcg agcacatgga acgggttggc atggattgta ggcgccgccc ataccttgt   7800 ctgcctcccc gcgttgcgtc gcggtgcatg gagccgggcc acctcgacct gaatggaagc   7860
cggcggcacc tcgctaacgg attcaccact ccaagaattg gagccaatca attcttgcgg   7920
agaactgtga atgcgcaaac caaccccttgg cagaacatat ccatcgcgtc gccatctcc   7980 agcagccgca cgcggcgcat ctcgggcagc gttgggtcct ggccacgggt gcgcatgatc   8040
gtgctcctgt cgttgaggac ccggctaggc tggcggggtt gccttactgg ttagcagaat   8100
gaatcaccga tacgcgagcg aacgtgaagc gactgctgct gcaaaacgtc tgcgacctga   8160
gcaacaacat gaatggtctt cggtttccgt gtttcgtaaa gtctggaaac gcggaagtcc   8220
cctacgtgct gctgaagttg cccgcaacag agagtggaac caaccggtga taccacgata   8280
ctatgactga gagtcaacgc catgagcggc ctcatttctt attctgagtt acaacagtcc   8340
gcaccgctgt ccggtagctc cttccggtgg gcgcggggca tgactatcgt cgccgcactt   8400
atgactgtct tctttatcat gcaactcgta ggacaggtgc cggcagcgcc caacagtccc   8460
```

```
ccggccacgg ggcctgccac catacccacg ccgaaacaag cgccctgcac cattatgttc    8520
cggatctgca tcgcaggatg ctgctggcta ccctgtggaa cacctacatc tgtattaacg    8580
aagcgctaac cgtttttatc aggctctggg aggcagaata aatgatcata tcgtcaatta    8640
ttacctccac ggggagagcc tgagcaaact ggcctcaggc atttgagaag cacacggtca    8700
cactgcttcc ggtagtcaat aaaccggtaa accagcaata gacataagcg gctatttaac    8760
gaccctgccc tgaaccgacg accgggtcga atttgctttc gaatttctgc cattcatccg    8820
cttattatca cttattcagg cgtagcacca ggcgtttaag ggcaccaata actgccttaa    8880
aaaaattacg ccccgccctg ccactcatcg cagtactgtt gtaattcatt aagcattctg    8940
ccgacatgga agccatcaca gacggcatga tgaacctgaa tcgccagcgg catcagcacc    9000
ttgtcgcctt gcgtataata tttgcccatg gtgaaaacgg gggcgaagaa gttgtccata    9060
ttggccacgt ttaaatcaaa actggtgaaa ctcacccagg gattggctga cgaaaaac     9120 atattctcaa taaacccttt agggaaatag gccaggtttt caccgtaaca cgccacatct    9180
tgcgaatata tgtgtagaaa ctgccggaaa tcgtcgtggt attcactcca gagcgatgaa    9240
aacgtttcag tttgctcatg gaaaacggtg taacaagggt gaacactatc ccatatcacc    9300
agctcaccgt ctttcattgc catacg                                         9326

<210> SEQ ID NO 61
<211> LENGTH: 9326
<212> TYPE: DNA
<213> ORGANISM: Artificial
<220> FEATURE:
<223> OTHER INFORMATION: pCas9_LacZ2
<220> FEATURE:
<221> NAME/KEY: gene
<222> LOCATION: (2225)..(6331)
<223> OTHER INFORMATION: product
<220> FEATURE:
<221> NAME/KEY: misc_feature
<222> LOCATION: (6484)..(6519)
<223> OTHER INFORMATION: repeat
<220> FEATURE:
<221> NAME/KEY: misc_feature
<222> LOCATION: (6520)..(6549)
<223> OTHER INFORMATION: CRSIPR target ELZ2
<220> FEATURE:
<221> NAME/KEY: misc_feature
<222> LOCATION: (6550)..(6585)
<223> OTHER INFORMATION: repeat

<400> SEQUENCE: 61
gaattccgga tgagcattca tcaggcgggc aagaatgtga ataaaggccg gataaaactt      60
gtgcttattt ttctttacgg tctttaaaaa ggccgtaata tccagctgaa cggtctggtt     120
ataggtacat tgagcaactg actgaaatgc ctcaaaatgt tctttacgat gccattggga     180
tatatcaacg gtggtatatc cagtgatttt tttctccatt ttagcttcct tagctcctga    240
aaatctcgat aactcaaaaa atacgcccgg tagtgatctt atttcattat ggtgaaagtt    300
ggaacctctt acgtgccgat caacgtctca ttttcgccaa agttggccc agggcttccc    360 ggtatcaaca gggacaccag gatttattta ttctgcgaag tgatcttccg tcacaggtat    420
ttattcggcg caaagtgcgt cgggtgatgc tgccaactta ctgatttagt gtatgatggt    480
gtttttgagg tgctccagtg gcttctgttt ctatcagctg tccctcctgt tcagctactg    540
acggggtggt gcgtaacggc aaaagcaccg ccggacatca gcgctagcgg agtgtatact    600
ggcttactat gttggcactg atgagggtgt cagtgaagtg cttcatgtgg caggagaaaa    660
```

```
aaggctgcac cggtgcgtca gcagaatatg tgatacagga tatattccgc ttcctcgctc    720
actgactcgc tacgctcggt cgttcgactg cggcgagcgg aaatggctta cgaacggggc    780
ggagatttcc tggaagatgc caggaagata cttaacaggg aagtgagagg gccgcggcaa    840
agccgttttt ccataggctc cgcccccctg acaagcatca cgaaatctga cgctcaaatc    900
agtggtggcg aaacccgaca ggactataaa gataccaggc gtttccccct ggcggctccc    960
tcgtgcgctc tcctgttcct gcctttcggt ttaccggtgt cattccgctg ttatggccgc   1020
gtttgtctca ttccacgcct gacactcagt tccgggtagg cagttcgctc caagctggac   1080
tgtatgcacg aaccccccgt tcagtccgac cgctgcgcct tatccggtaa ctatcgtctt   1140
gagtccaacc cggaaagaca tgcaaaagca ccactggcag cagccactgg taattgattt   1200
agaggagtta gtcttgaagt catgcgccgg ttaaggctaa actgaaagga caagttttgg   1260
tgactgcgct cctccaagcc agttacctcg gttcaaagag ttggtagctc agagaacctt   1320 cgaaaaccg ccctgcaagg cggttttttc gttttcagag caagagatta cgcgcagacc   1380
aaaacgatct caagaagatc atcttattaa tcagataaaa tatttctaga tttcagtgca   1440
atttatctct tcaaatgtag cacctgaagt cagccccata cgatataagt tgtaattctc   1500
atgtttgaca gcttatcatc gataagcttt aatgcggtag tttatcacag ttaaattgct   1560
aacgcagtca ggcaccgtgt atgaaatcta acaatgcgct catcgtcatc ctcggcaccg   1620
tcaccctgga tgctgtaggc ataggcttgg ttatgccggt actgccgggc ctcttgcggg   1680
attacgaaat catcctgtgg agcttagtag gtttagcaag atggcagcgc ctaaatgtag   1740
aatgataaaa ggattaagag attaatttcc ctaaaaatga taaaacaagc gttttgaaag   1800
cgcttgtttt tttggtttgc agtcagagta gaatagaagt atcaaaaaaa gcaccgactc   1860
ggtgccactt tttcaagttg ataacggact agccttattt taacttgcta tgctgttttg   1920
aatggttcca acaagattat tttataactt ttataacaaa taatcaagga gaaattcaaa   1980
gaaatttatc agccataaaa caatacttaa tactatagaa tgataacaaa ataaactact   2040
ttttaaaaga attttgtgtt ataatctatt tattattaag tattgggtaa tattttttga   2100
agagatattt tgaaaagaa aaattaaagc atattaaact aatttcggag gtcattaaaa   2160
ctattattga aatcatcaaa ctcattatgg atttaattta aacttttat tttaggaggc   2220 aaaaatggat aagaaatact caataggctt agatatcggc acaaatagcg tcggatgggc   2280
ggtgatcact gatgaatata aggttccgtc taaaaagttc aaggttctgg aaatacaga   2340 ccgccacagt atcaaaaaa atcttatagg ggctctttta tttgacagtg agagacagc   2400 ggaagcgact cgtctcaaac ggacagctcg tagaaggtat acacgtcgga agaatcgtat   2460
ttgttatcta caggagattt tttcaaatga gatggcgaaa gtagatgata gtttctttca   2520
tcgacttgaa gagtcttttt tggtggaaga agacaagaag catgaacgtc atcctatttt   2580
tggaaatata gtagatgaag ttgcttatca tgagaaatat ccaactatct atcatctgcg   2640
aaaaaaattg gtagattcta ctgataaagc ggatttgcgc ttaatctatt tggccttagc   2700
gcatatgatt aagtttcgtg gtcatttttt gattgaggga gatttaaatc ctgataatag   2760
tgatgtggac aaactatttta tccagttggt acaaacctac aatcaattat ttgaagaaaa   2820
ccctattaac gcaagtggag tagatgctaa agcgattctt tctgcacgat tgagtaaatc   2880
aagacgatta gaaaatctca ttgctcagct ccccggtgag aagaaaatg gcttatttgg   2940 gaatctcatt gctttgtcat tgggtttgac ccctaatttt aaatcaaatt ttgatttggc   3000
agaagatgct aaattacagc tttcaaaaga tacttacgat gatgatttag ataatttatt   3060
```

```
ggcgcaaatt ggagatcaat atgctgattt gttttttggca gctaagaatt tatcagatgc    3120
tattttactt tcagatatcc taagagtaaa tactgaaata actaaggctc ccctatcagc    3180
ttcaatgatt aaacgctacg atgaacatca tcaagacttg actcttttaa aagctttagt    3240
tcgacaacaa cttccagaaa agtataaaga aatctttttt gatcaatcaa aaaacggata    3300
tgcaggttat attgatgggg gagctagcca agaagaattt tataaattta tcaaaccaat    3360
tttagaaaaa atggatggta ctgaggaatt attggtgaaa ctaaatcgtg aagatttgct    3420
gcgcaagcaa cggacctttg caacggctc tattccccat caaattcact gggtgagct    3480 gcatgctatt ttgagaagac aagaagactt ttatccattt ttaaaagaca atcgtgagaa    3540
gattgaaaaa atcttgactt ttcgaattcc ttattatgtt ggtccattgg cgcgtggcaa    3600
tagtcgtttt gcatggatga ctcggaagtc tgaagaaaca attacccat ggaattttga    3660 agaagttgtc gataaaggtg cttcagctca atcatttatt gaacgcatga caaactttga    3720
taaaaatctt ccaaatgaaa aagtactacc aaaacatagt ttgctttatg agtattttac    3780
ggtttataac gaattgacaa aggtcaaata tgttactgaa ggaatgcgaa accagcatt    3840 tctttcaggt gaacagaaga aagccattgt tgatttactc ttcaaaacaa atcgaaaagt    3900
aaccgttaag caattaaaag aagattattt caaaaaaata gaatgttttg atagtgttga    3960
aatttcagga gttgaagata gatttaatgc ttcattaggt acctaccatg atttgctaaa    4020
aattattaaa gataaagatt ttttggataa tgaagaaaat gaagatatct tagaggatat    4080
tgttttaaca ttgaccttat ttgaagatag ggagatgatt gaggaaagac ttaaaacata    4140
tgctcacctc tttgatgata aggtgatgaa acagcttaaa cgtcgccgtt atactggttg    4200
gggacgtttg tctcgaaaat tgattaatgg tattagggat aagcaatctg gcaaaacaat    4260
attagatttt ttgaaatcag atggttttgc caatcgcaat tttatgcagc tgatccatga    4320
tgatagtttg acatttaaag aagacattca aaaagcacaa gtgtctggac aaggcgatag    4380
tttacatgaa catattgcaa atttagctgg tagccctgct attaaaaaag gtattttaca    4440
gactgtaaaa gttgttgatg aattggtcaa agtaatgggg cggcataagc cagaaaatat    4500
cgttattgaa atggcacgtg aaaatcagac aactcaaaag ggccagaaaa attcgcgaga    4560
gcgtatgaaa cgaatcgaag aaggtatcaa agaattagga agtcagattc ttaaagagca    4620
tcctgttgaa aatactcaat tgcaaaatga aaagctctat ctctattatc tccaaaatgg    4680
aagagacatg tatgtggacc aagaattaga tattaatcgt ttaagtgatt atgatgtcga    4740
tcacattgtt ccacaaagtt tccttaaaga cgattcaata gacaataagg tcttaacgcg    4800
ttctgataaa aatcgtggta atcggataa cgttccaagt gaagaagtag tcaaaaagat    4860
gaaaaactat tggagacaac ttctaaacgc caagttaatc actcaacgta agtttgataa    4920
tttaacgaaa gctgaacgtg gaggtttgag tgaacttgat aaagctggtt ttatcaaacg    4980
ccaattggtt gaaactcgcc aaatcactaa gcatgtggca caaattttgg atagtcgcat    5040
gaatactaaa tacgatgaaa atgataaact tattcgagag gttaaagtga ttaccttaaa    5100
atctaaatta gtttctgact tccgaaaaga tttccaattc tataaagtac gtgagattaa    5160
caattaccat catgccccatg atgcgtatct aaatgccgtc gttggaactg ctttgattaa    5220
gaaatatcca aaacttgaat cggagtttgt ctatggtgat tataaagttt atgatgttcg    5280
taaaatgatt gctaagtctg agcaagaaat aggcaaagca accgcaaaat atttcttta    5340 ctctaatatc atgaacttct tcaaaacaga aattacactt gcaaatggag agattcgcaa    5400
```

```
acgccctcta atcgaaacta atggggaaac tggagaaatt gtctgggata aagggcgaga      5460
ttttgccaca gtgcgcaaag tattgtccat gccccaagtc aatattgtca agaaaacaga      5520
agtacagaca ggcggattct ccaaggagtc aattttacca aaaagaaatt cggacaagct      5580
tattgctcgt aaaaaagact gggatccaaa aaaatatggt ggttttgata gtccaacggt      5640
agcttattca gtcctagtgg ttgctaaggt ggaaaaaggg aaatcgaaga agttaaaatc      5700
cgttaaagag ttactaggga tcacaattat ggaaagaagt tcctttgaaa aaaatccgat      5760 tgactttta gaagctaaag gatataagga agttaaaaaa gacttaatca ttaaactacc       5820
taaatatagt cttttgagt tagaaaacgg tcgtaaacgg atgctggcta gtgccggaga       5880
attacaaaaa ggaaatgagc tggctctgcc aagcaaatat gtgaattttt tatatttagc      5940
tagtcattat gaaagttga agggtagtcc agaagataac gaacaaaaac aattgtttgt       6000
ggagcagcat aagcattatt tagatgagat tattgagcaa atcagtgaat tttctaagcg      6060
tgttatttta gcagatgcca atttagataa agttcttagt gcataaacaa acatagaga      6120 caaaccaata cgtgaacaag cagaaaatat tattcattta tttacgttga cgaatcttgg      6180
agctcccgct gcttttaaat attttgatac aacaattgat cgtaaacgat atacgtctac      6240
aaaagaagtt ttagatgcca ctcttatcca tcaatccatc actggtcttt atgaaacacg      6300
cattgatttg agtcagctag gaggtgactg aagtatattt tagatgaaga ttatttctta      6360
ataactaaaa atatggtata atactcttaa taaatgcagt aatacagggg cttttcaaga      6420
ctgaagtcta gctgagacaa atagtgcgat tacgaaattt tttagacaaa aatagtctac      6480
gaggttttag agctatgctg ttttgaatgg tcccaaaacc cattacggtc aatccgccgt      6540
ttgttcccag ttttagagct atgctgtttt gaatggtccc aaaacttcag cacactgaga      6600
cttgttgagt tccatgtttt agagctatgc tgttttgaat ggactccatt caacattgcc      6660
gatgataact tgagaaagag ggttaatacc agcagtcgga taccttccta ttctttctgt      6720
taaagcgttt tcatgttata ataggcaaaa gaagagtagt gtgatcgtcc attccgacag      6780
catcgccagt cactatggcg tgctgctagc gctatatgcg ttgatgcaat tctatgcgc       6840 acccgttctc ggagcactgt ccgaccgctt ggccgccgc ccagtcctgc tcgcttcgct       6900
acttggagcc actatcgact acgcgatcat ggcgaccaca cccgtcctgt ggatcctcta      6960
cgccggacga tcgtggccg gcatcaccgg cgccacaggt gcggttgctg gcgcctatat       7020
cgccgacatc accgatgggg aagatcgggc tcgccacttc gggctcatga gcgcttgttt      7080
cggcgtgggt atggtggcag gccccgtggc cgggggactg ttgggcgcca tctccttgca      7140
tgcaccattc cttgcggcgg cggtgctcaa cggcctcaac ctactactgg gctgcttcct      7200
aatgcaggag tcgcataagg gagagcgtcg accgatgccc ttgagagcct tcaacccagt      7260
cagctccttc cggtgggcgc ggggcatgac tatcgtcgcc gcacttatga ctgtcttctt      7320
tatcatgcaa ctcgtaggac aggtgccggc agcgctctgg gtcattttcg gcgaggaccg      7380
ctttcgctgg agcgcgacga tgatcggcct gtcgcttgcg gtattcggaa tcttgcacgc      7440
cctcgctcaa gccttcgtca ctggtcccgc caccaaacgt ttcggcgaga agcaggccat      7500
tatcgccggc atggcggccg acgcgctggg ctacgtcttg ctggcgttcg cgacgcgagg      7560
ctggatggcc ttccccatta tgattcttct cgcttccggc ggcatcggga tgcccgcgtt      7620
gcaggccatg ctgtccaggc aggtagatga cgaccatcag gacagcttc aaggatcgct       7680 cgcggctctt accagcctaa cttcgatcat tggaccgctg atcgtcacgg cgatttatgc      7740
cgcctcggcg agcacatgga acgggttggc atggattgta ggcgccgccc tataccttgt      7800
```

```
ctgcctcccc gcgttgcgtc gcggtgcatg gagccgggcc acctcgacct gaatggaagc    7860
cggcggcacc tcgctaacgg attcaccact ccaagaattg gagccaatca attcttgcgg    7920
agaactgtga atgcgcaaac caaccettgg cagaacatat ccatcgcgtc cgccatctcc    7980
agcagccgca cgcggcgcat ctcgggcagc gttgggtcct ggccacgggt gcgcatgatc    8040
gtgctcctgt cgttgaggac ccggctaggc tggcggggtt gccttactgg ttagcagaat    8100
gaatcaccga tacgcgagcg aacgtgaagc gactgctgct gcaaaacgtc tgcgacctga    8160
gcaacaacat gaatggtctt cggtttccgt gtttcgtaaa gtctggaaac gcggaagtcc    8220
cctacgtgct gctgaagttg cccgcaacag agagtggaac caaccggtga taccacgata    8280
ctatgactga gagtcaacgc catgagcggc ctcatttctt attctgagtt acaacagtcc    8340
gcaccgctgt ccgtagctc cttccggtgg gcgcggggca tgactatcgt cgccgcactt    8400
atgactgtct tctttatcat gcaactcgta ggacaggtgc cggcagcgcc caacagtccc    8460
ccggccacgg ggcctgccac catacccacg ccgaaacaag cgccctgcac cattatgttc    8520
cggatctgca tcgcaggatg ctgctggcta ccctgtggaa cacctacatc tgtattaacg    8580
aagcgctaac cgtttttatc aggctctggg aggcagaata aatgatcata tcgtcaatta    8640
ttacctccac ggggagagcc tgagcaaact ggcctcaggc atttgagaag cacacggtca    8700
cactgcttcc ggtagtcaat aaaccggtaa accagcaata gacataagcg gctatttaac    8760
gaccctgccc tgaaccgacg accgggtcga atttgctttc gaatttctgc cattcatccg    8820
cttattatca cttattcagg cgtagcacca ggcgtttaag ggcaccaata actgccttaa    8880
aaaaattacg ccccgccctg ccactcatcg cagtactgtt gtaattcatt aagcattctg    8940
ccgacatgga agccatcaca gacggcatga tgaacctgaa tcgccagcgg catcagcacc    9000
ttgtcgcctt gcgtataata tttgcccatg gtgaaaacgg gggcgaagaa gttgtccata    9060
ttggccacgt ttaaatcaaa actggtgaaa ctcacccagg gattggctga cgaaaaaac    9120 atattctcaa taaacccttt agggaaatag gccaggtttt caccgtaaca cgccacatct    9180
tgcgaatata tgtgtagaaa ctgccggaaa tcgtcgtggt attcactcca gagcgatgaa    9240
aacgtttcag tttgctcatg gaaaacggtg taacaagggt gaacactatc ccatatcacc    9300
agctcaccgt ctttcattgc catacg                                         9326
```

<210> SEQ ID NO 62
<211> LENGTH: 2349
<212> TYPE: DNA
<213> ORGANISM: Artificial
<220> FEATURE:
<223> OTHER INFORMATION: psgRNAc BsaI
<220> FEATURE:
<221> NAME/KEY: gene
<222> LOCATION: (219)..(1909)
<223> OTHER INFORMATION: cat CmR chloramphenicol acetyltransferase -
     positions are given on the complementary strand : complement
     (1909-219)
<220> FEATURE:
<221> NAME/KEY: promoter
<222> LOCATION: (220)..(322)
<223> OTHER INFORMATION: cat promoter -  positions are given on the
     complementary strand : complement (220..322)
<220> FEATURE:
<221> NAME/KEY: rep_origin
<222> LOCATION: (848)..(1393)
<223> OTHER INFORMATION: p15A ori  - positions are given on the
     complementary strand : complement (848..1393)
<220> FEATURE:
<221> NAME/KEY: promoter
<222> LOCATION: (1510)..(1538)

```
<223> OTHER INFORMATION: Promoter (BBa_J23119)
<220> FEATURE:
<221> NAME/KEY: misc_feature
<222> LOCATION: (1545)..(1564)
<223> OTHER INFORMATION: Control spacer with 2 BsaI
<220> FEATURE:
<221> NAME/KEY: misc_RNA
<222> LOCATION: (1565)..(1640)
<223> OTHER INFORMATION: gRNA scaffold
<220> FEATURE:
<221> NAME/KEY: misc_feature
<222> LOCATION: (1642)..(1647)
<223> OTHER INFORMATION: part of the tracrRNA
<220> FEATURE:
<221> NAME/KEY: gene
<222> LOCATION: (1648)..(1652)
<223> OTHER INFORMATION: lacI

<400> SEQUENCE: 62
gaattccgga tgagcattca tcaggcgggc aagaatgtga ataaaggccg gataaaactt      60
gtgcttattt ttctttacgg tctttaaaaa ggccgtaata tccagctgaa cggtctggtt     120
ataggtacat tgagcaactg actgaaatgc ctcaaaatgt tctttacgat gccattggga     180
tatatcaacg gtggtatatc cagtgatttt tttctccatt ttagcttcct tagctcctga     240
aaatctcgat aactcaaaaa atacgcccgg tagtgatctt atttcattat ggtgaaagtt     300
ggaacctctt acgtgccgat caacgtctca ttttcgccaa agttggccc agggcttccc     360
ggtatcaaca gggacaccag gatttattta ttctgcgaag tgatcttccg tcacaggtat     420
ttattcggcg caaagtgcgt cgggtgatgc tgccaactta ctgatttagt gtatgatggt     480
gtttttgagg tgctccagtg gcttctgttt ctatcagctg tccctcctgt tcagctactg     540
acggggtggt gcgtaacggc aaaagcaccg ccggacatca gcgctagcgg agtgtatact     600
ggcttactat gttggcactg atgagggtgt cagtgaagtg cttcatgtgg caggagaaaa     660
aaggctgcac cggtgcgtca gcagaatatg tgatacagga tatattccgc ttcctcgctc     720
actgactcgc tacgctcggt cgttcgactg cggcgagcgg aaatggctta cgaacggggc     780
ggagatttcc tggaagatgc caggaagata cttaacaggg aagtgagagg gccgcggcaa     840
agccgttttt ccataggctc cgcccccctg acaagcatca cgaaatctga cgctcaaatc     900
agtggtggcg aaacccgaca ggactataaa gataccaggc gtttccccct ggcggctccc     960
tcgtgcgctc tcctgttcct gcctttcggt ttaccggtgt cattccgctg ttatggccgc    1020
gtttgtctca ttccacgcct gacactcagt tccgggtagg cagttcgctc caagctggac    1080
tgtatgcacg aaccccccgt tcagtccgac cgctgcgcct tatccggtaa ctatcgtctt    1140
gagtccaacc cggaaagaca tgcaaaagca ccactggcag cagccactgg taattgattt    1200
agaggagtta gtcttgaagt catgcgccgg ttaaggctaa actgaaagga caagtttggg    1260
tgactgcgct cctccaagcc agttacctcg gttcaaagag ttggtagctc agagaacctt    1320
cgaaaaaccg ccctgcaagg cggttttttc gttttcagag caagagatta cgcgcagacc    1380
aaaacgatct caagaagatc atcttattaa tcagataaaa tatttctaga tttcagtgca    1440
atttatctct tcaaatgtag cacctggcta ggaggtgact gaagtatatt ttaggaattc    1500
taaagatctt tgacagctag ctcagtccta ggtataatac tagttgagac cagtctaggt    1560
ctcggtttta gagctagaaa tagcaagtta aaataaggct agtccgttat caacttgaaa    1620
aagtggcacc gagtcggtgc ttttttggt agtgcagcgc gatcgtaatc aggggggaga    1680
gcctgagcaa actggcctca ggcatttgag aagcacacgg tcacactgct tccggtagtc    1740
aataaaccgg taaaccagca atagacataa gcggctattt aacgaccctg ccctgaaccg    1800
```

| acgaccgggt cgaatttgct ttcgaatttc tgccattcat ccgcttatta tcacttattc | 1860 |
| aggcgtagca ccaggcgttt aagggcacca ataactgcct taaaaaaatt acgccccgcc | 1920 |
| ctgccactca tcgcagtact gttgtaattc attaagcatt ctgccgacat ggaagccatc | 1980 |
| acagacggca tgatgaacct gaatcgccag cggcatcagc accttgtcgc cttgcgtata | 2040 |
| atatttgccc atggtgaaaa cggggggcgaa gaagttgtcc atattggcca cgtttaaatc | 2100 |
| aaaactggtg aaactcaccc agggattggc tgagacgaaa aacatattct caataaaccc | 2160 |
| tttagggaaa taggccaggt tttcaccgta acacgccaca tcttgcgaat atatgtgtag | 2220 |
| aaactgccgg aaatcgtcgt ggtattcact ccagagcgat gaaaacgttt cagtttgctc | 2280 |
| atggaaaacg gtgtaacaag ggtgaacact atcccatatc accagctcac cgtctttcat | 2340 |
| tgccatacg | 2349 |

<210> SEQ ID NO 63
<211> LENGTH: 9326
<212> TYPE: DNA
<213> ORGANISM: Artificial
<220> FEATURE:
<223> OTHER INFORMATION: pCas9

<400> SEQUENCE: 63

| gaattccgga tgagcattca tcaggcgggc aagaatgtga ataaaggccg gataaaactt | 60 |
| gtgcttattt ttctttacgg tctttaaaaa ggccgtaata tccagctgaa cggtctggtt | 120 |
| ataggtacat tgagcaactg actgaaatgc ctcaaaatgt tctttacgat gccattggga | 180 |
| tatatcaacg gtggtatatc cagtgatttt tttctccatt ttagcttcct tagctcctga | 240 |
| aaatctcgat aactcaaaaa atacgcccgg tagtgatctt atttcattat ggtgaaagtt | 300 |
| ggaacctctt acgtgccgat caacgtctca ttttcgccaa aagttggccc agggcttccc | 360 |
| ggtatcaaca gggacaccag gatttattta ttctgcgaag tgatcttccg tcacaggtat | 420 |
| ttattcggcg caaagtgcgt cgggtgatgc tgccaactta ctgatttagt gtatgatggt | 480 |
| gtttttgagg tgctccagtg gcttctgttt ctatcagctg tccctcctgt tcagctactg | 540 |
| acggggtggt gcgtaacggc aaaagcaccg ccggacatca gcgctagcgg agtgtatact | 600 |
| ggcttactat gttggcactg atgagggtgt cagtgaagtg cttcatgtgg caggagaaaa | 660 |
| aaggctgcac cggtgcgtca gcagaatatg tgatacagga tatattccgc ttcctcgctc | 720 |
| actgactcgc tacgctcggt cgttcgactg cggcgagcgg aaatggctta cgaacggggc | 780 |
| ggagatttcc tggaagatgc caggaagata cttaacaggg aagtgagagg ccgcggcaa | 840 |
| agccgttttt ccataggctc cgcccccctg acaagcatca cgaaatctga cgctcaaatc | 900 |
| agtggtggcg aaacccgaca ggactataaa gataccaggc gtttccccct ggcggctccc | 960 |
| tcgtgcgctc tcctgttcct gcctttcggt ttaccggtgt cattccgctg ttatggccgc | 1020 |
| gtttgtctca ttccacgcct gacactcagt tccgggtagg cagttcgctc caagctggac | 1080 |
| tgtatgcacg aaccccccgt tcagtccgac cgctgcgcct tatccggtaa ctatcgtctt | 1140 |
| gagtccaacc cggaaagaca tgcaaaagca ccactggcag cagccactgg taattgattt | 1200 |
| agaggagtta gtcttgaagt catgcgccgg ttaaggctaa actgaaagga caagttttgg | 1260 |
| tgactgcgct cctccaagcc agttacctcg gttcaaagag ttggtagctc agagaacctt | 1320 |
| cgaaaaaccg ccctgcaagg cggttttttc gttttcagag caagagatta gcgcagacc | 1380 |
| aaaacgatct caagaagatc atcttattaa tcagataaaa tatttctaga tttcagtgca | 1440 |

```
atttatctct tcaaatgtag cacctgaagt cagccccata cgatataagt tgtaattctc    1500
atgtttgaca gcttatcatc gataagcttt aatgcggtag tttatcacag ttaaattgct    1560
aacgcagtca ggcaccgtgt atgaaatcta acaatgcgct catcgtcatc ctcggcaccg    1620
tcaccctgga tgctgtaggc ataggcttgg ttatgccggt actgccgggc ctcttgcggg    1680
attacgaaat catcctgtgg agcttagtag gtttagcaag atggcagcgc ctaaatgtag    1740
aatgataaaa ggattaagag attaatttcc ctaaaaatga taaacaagc gttttgaaag     1800 cgcttgtttt tttggtttgc agtcagagta gaatagaagt atcaaaaaaa gcaccgactc    1860
ggtgccactt tttcaagttg ataacggact agccttattt taacttgcta tgctgttttg    1920
aatggttcca acaagattat tttataactt ttataacaaa taatcaagga gaaattcaaa    1980
gaaatttatc agccataaaa caatacttaa tactatagaa tgataacaaa ataaactact    2040
ttttaaaaga attttgtgtt ataatctatt tattattaag tattgggtaa tattttttga    2100
agagatattt tgaaaagaa aaattaaagc atattaaact aatttcggag gtcattaaaa     2160
ctattattga aatcatcaaa ctcattatgg atttaattta aacttttat tttaggaggc      2220 aaaaatggat aagaaatact caataggctt agatatcggc acaaatagcg tcggatgggc    2280
ggtgatcact gatgaatata aggttccgtc taaaaagttc aaggttctgg aaatacaga     2340 ccgccacagt atcaaaaaaa atcttatagg ggctctttta tttgacagtg gagagacagc    2400
ggaagcgact cgtctcaaac ggacagctcg tagaaggtat acacgtcgga gaatcgtat    2460 ttgttatcta caggagattt tttcaaatga gatggcgaaa gtagatgata gtttctttca    2520
tcgacttgaa gagtcttttt tggtggaaga agacaagaag catgaacgtc atcctatttt    2580
tggaaatata gtagatgaag ttgcttatca tgagaaatat ccaactatct atcatctgcg    2640
aaaaaaattg gtagattcta ctgataaagc ggatttgcgc ttaatctatt tggccttagc    2700
gcatatgatt aagtttcgtg gtcatttttt gattgaggga gatttaaatc ctgataatag    2760
tgatgtggac aaactattta tccagttggt acaaacctac aatcaattat ttgaagaaaa    2820
ccctattaac gcaagtggag tagatgctaa agcgattctt tctgcacgat tgagtaaatc    2880
aagacgatta gaaaatctca ttgctcagct ccccggtgag aagaaaaatg cttatttgg     2940 gaatctcatt gctttgtcat tgggtttgac ccctaatttt aaatcaaatt ttgatttggc    3000
agaagatgct aaattacagc tttcaaaaga tacttacgat gatgatttag ataaatttatt   3060 ggcgcaaatt ggagatcaat atgctgattt gttttttggca gctaagaatt tatcagatgc   3120 tatttttactt tcagatatcc taagagtaaa tactgaaata actaaggctc ccctatcagc   3180
ttcaatgatt aaacgctacg atgaacatca tcaagacttg actcttttaa aagctttagt    3240
tcgacaacaa cttccagaaa agtataaaga aatcttttt gatcaatcaa aaaacggata     3300
tgcaggttat attgatgggg agctagcca agaagaattt tataaattta tcaaaccaat    3360 tttagaaaaaa atgatggta ctgaggaatt attggtgaaa ctaaatcgtg aagatttgct   3420
gcgcaagcaa cggaccttg acaacggctc tattccccat caaattcact gggtgagct     3480 gcatgctatt ttgagaagac aagaagactt ttatccattt ttaaaagaca atcgtgagaa    3540
gattgaaaaa atcttgactt ttcgaattcc ttattatgtt ggtccattgg cgcgtggcaa    3600
tagtcgtttt gcatggatga ctcggaagtc tgaagaaaca attaccccat ggaattttga    3660
agaagttgtc gataaaggtg cttcagctca atcatttatt gaacgcatga caaactttga    3720
taaaaatctt ccaaatgaaa aagtactacc aaaacatagt ttgctttatg agtattttac    3780
ggtttataac gaattgacaa aggtcaaata tgttactgaa ggaatgcgaa aaccagcatt    3840
```

```
tctttcaggt gaacagaaga aagccattgt tgatttactc ttcaaaacaa atcgaaaagt    3900
aaccgttaag caattaaaag aagattattt caaaaaaata gaatgttttg atagtgttga    3960
aatttcagga gttgaagata gatttaatgc ttcattaggt acctaccatg atttgctaaa    4020
aattattaaa gataaagatt ttttggataa tgaagaaaat gaagatatct tagaggatat    4080
tgttttaaca ttgaccttat ttgaagatag ggagatgatt gaggaaagac ttaaaacata    4140
tgctcacctc tttgatgata aggtgatgaa acagcttaaa cgtcgccgtt atactggttg    4200
gggacgtttg tctcgaaaat tgattaatgg tattagggat aagcaatctg gcaaaacaat    4260
attagatttt ttgaaatcag atggttttgc caatcgcaat tttatgcagc tgatccatga    4320
tgatagtttg acatttaaag aagacattca aaaagcacaa gtgtctggac aaggcgatag    4380
tttacatgaa catattgcaa atttagctgg tagccctgct attaaaaaag gtattttaca    4440
gactgtaaaa gttgttgatg aattggtcaa agtaatgggg cggcataagc cagaaaatat    4500
cgttattgaa atggcacgtg aaaatcagac aactcaaaag ggccagaaaa attcgcgaga    4560
gcgtatgaaa cgaatcgaag aaggtatcaa agaattagga agtcagattc ttaaagagca    4620
tcctgttgaa aatactcaat tgcaaaatga aaagctctat ctctattatc tccaaaatgg    4680
aagagacatg tatgtggacc aagaattaga tattaatcgt ttaagtgatt atgatgtcga    4740
tcacattgtt ccacaaagtt tccttaaaga cgattcaata gacaataagg tcttaacgcg    4800
ttctgataaa atcgtggta atcggataa cgttccaagt gaagaagtag tcaaaaagat    4860
gaaaaactat tggagacaac ttctaaacgc caagttaatc actcaacgta agtttgataa    4920
tttaacgaaa gctgaacgtg gaggtttgag tgaacttgat aaagctggtt ttatcaaacg    4980
ccaattggtt gaaactcgcc aaatcactaa gcatgtggca caattttggg atagtcgcat    5040
gaatactaaa tacgatgaaa atgataaact tattcgagag gttaaagtga ttaccttaaa    5100
atctaaatta gtttctgact tccgaaaaga tttccaattc tataaagtac gtgagattaa    5160
caattaccat catgcccatg atgcgtatct aaatgccgtc gttggaactg ctttgattaa    5220
gaaatatcca aaacttgaat cggagtttgt ctatggtgat tataaagttt atgatgttcg    5280
taaaatgatt gctaagtctg agcaagaaat aggcaaagca accgcaaaat atttctttta    5340
ctctaatatc atgaacttct tcaaaacaga aattacactt gcaaatggag agattcgcaa    5400
acgccctcta atcgaaacta atggggaaac tggagaaatt gtctgggata agggcgaga    5460 ttttgccaca gtgcgcaaag tattgtccat gccccaagtc aatattgtca agaaaacaga    5520
agtacagaca ggcggattct ccaaggagtc aattttacca aaaagaaatt cggacaagct    5580
tattgctcgt aaaaaagact gggatccaaa aaaatatggt ggttttgata gtccaacggt    5640
agcttattca gtcctagtgg ttgctaaggt ggaaaaaggg aaatcgaaga gttaaaatc    5700 cgttaaagag ttactaggga tcacaattat ggaaagaagt tccttgaaa aaaatccgat    5760 tgacttttta gaagctaaag gatataagga agttaaaaaa gacttaatca ttaaactacc    5820
taaatatagt cttttgagt tagaaaacgg tcgtaaacgg atgctggcta gtgccggaga    5880
attacaaaaa ggaaatgagc tggctctgcc aagcaaatat gtgaattttt tatatttagc    5940
tagtcattat gaaaagttga agggtagtcc agaagataac gaacaaaaac aattgtttgt    6000
ggagcagcat aagcattatt tagatgagat tattgagcaa atcagtgaat tttctaagcg    6060
tgttatttta gcagatgcca atttagataa agttcttagt gcatataaca acatagaga    6120 caaaccaata cgtgaacaag cagaaaatat tattcattta tttacgttga cgaatcttgg    6180
```

```
agctcccgct gcttttaaat attttgatac aacaattgat cgtaaacgat atacgtctac    6240
aaaagaagtt ttagatgcca ctcttatcca tcaatccatc actggtcttt atgaaacacg    6300
cattgatttg agtcagctag gaggtgactg aagtatattt tagatgaaga ttatttctta    6360
ataactaaaa atatggtata atactcttaa taaatgcagt aatacagggg cttttcaaga    6420
ctgaagtcta gctgagacaa atagtgcgat tacgaaattt tttagacaaa aatagtctac    6480
gaggttttag agctatgctg ttttgaatgg tcccaaaact gagaccagtc tcggaagctc    6540
aaaggtctcg ttttagagct atgctgtttt gaatggtccc aaaacttcag cacactgaga    6600
cttgttgagt tccatgtttt agagctatgc tgttttgaat ggactccatt caacattgcc    6660
gatgataact tgagaaagag ggttaatacc agcagtcgga taccttccta ttctttctgt    6720
taaagcgttt tcatgttata ataggcaaaa gaagagtagt gtgatcgtcc attccgacag    6780
catcgccagt cactatggcg tgctgctagc gctatatgcg ttgatgcaat ttctatgcgc    6840
acccgttctc ggagcactgt ccgaccgctt tggccgccgc ccagtcctgc tcgcttcgct    6900
acttggagcc actatcgact acgcgatcat ggcgaccaca cccgtcctgt ggatcctcta    6960
cgccggacgc atcgtggccg gcatcaccgg cgccacaggt gcggttgctg gcgcctatat    7020
cgccgacatc accgatgggg aagatcgggc tcgccacttc gggctcatga gcgcttgttt    7080
cggcgtgggt atggtggcag gccccgtggc cgggggactg ttgggcgcca tctccttgca    7140
tgcaccattc cttgcggcgg cggtgctcaa cggcctcaac ctactactgg gctgcttcct    7200
aatgcaggag tcgcataagg gagagcgtcg accgatgccc ttgagagcct tcaacccagt    7260
cagctccttc cggtgggcgc ggggcatgac tatcgtcgcc gcacttatga ctgtcttctt    7320
tatcatgcaa ctcgtaggac aggtgccggc agcgctctgg gtcattttcg gcgaggaccg    7380
cttccgctgg agcgcgacga tgatcggcct gtcgcttgcg gtattcggaa tcttgcacgc    7440
cctcgctcaa gccttcgtca ctggtcccgc caccaaacgt ttcggcgaga agcaggccat    7500
tatcgccggc atggcggccg acgcgctggg ctacgtcttg ctggcgttcg cgacgcgagg    7560
ctggatggcc ttccccatta tgattcttct cgcttccggc ggcatcggga tgcccgcgtt    7620
gcaggccatg ctgtccaggc aggtagatga cgaccatcag ggacagcttc aaggatcgct    7680
cgcggctctt accagcctaa cttcgatcat tggaccgctg atcgtcacgg cgatttatgc    7740
cgcctcggcg agcacatgga acgggttggc atggattgta ggcgccgccc tataccttgt    7800
ctgcctcccc gcgttgcgtc gcggtgcatg gagccgggcc acctcgacct gaatggaagc    7860
cggcggcacc tcgctaacgg attcaccact ccaagaattg gagccaatca attcttgcgg    7920
agaactgtga atgcgcaaac caacccttgg cagaacatat ccatcgcgtc cgccatctcc    7980
agcagccgca cgcggcgcat ctcgggcagc gttgggtcct ggccacgggt gcgcatgatc    8040
gtgctcctgt cgttgaggac ccggctaggc tggcggggtt gccttactgg ttagcagaat    8100
gaatcaccga tacgcgagcg aacgtgaagc gactgctgct gcaaaacgtc tgcgacctga    8160
gcaacaacat gaatggtctt cggtttccgt gtttcgtaaa gtctggaaac gcggaagtcc    8220
cctacgtgct gctgaagttg cccgcaacag agagtggaac caaccggtga taccacgata    8280
ctatgactga gagtcaacgc catgagcggc ctcatttctt attctgagtt acaacagtcc    8340
gcaccgctgt ccggtagctc cttccggtgg gcgcggggca tgactatcgt cgccgcactt    8400
atgactgtct tctttatcat gcaactcgta ggacaggtgc cggcagcgcc caacagtccc    8460
ccggccacgg ggcctgccac catacccacg ccgaaacaag cgccctgcac cattatgttc    8520
cggatctgca tcgcaggatg ctgctggcta ccctgtggaa cacctacatc tgtattaacg    8580
```

```
aagcgctaac cgtttttatc aggctctggg aggcagaata aatgatcata tcgtcaatta     8640
ttacctccac ggggagagcc tgagcaaact ggcctcaggc atttgagaag cacacggtca     8700
cactgcttcc ggtagtcaat aaaccggtaa accagcaata gacataagcg gctatttaac     8760 gacccctgccc tgaaccgacg accgggtcga atttgctttc gaatttctgc cattcatccg    8820
cttattatca cttattcagg cgtagcacca ggcgtttaag ggcaccaata actgccttaa     8880
aaaaattacg ccccgccctg ccactcatcg cagtactgtt gtaattcatt aagcattctg     8940
ccgacatgga agccatcaca gacggcatga tgaacctgaa tcgccagcgg catcagcacc     9000
ttgtcgcctt gcgtataata tttgcccatg gtgaaaacgg gggcgaagaa gttgtccata     9060
ttggccacgt ttaaatcaaa actggtgaaa ctcacccagg gattggctga gacgaaaaac     9120
atattctcaa taaaccettt agggaaatag gccaggtttt caccgtaaca cgccacatct     9180
tgcgaatata tgtgtagaaa ctgccggaaa tcgtcgtggt attcactcca gagcgatgaa     9240
aacgtttcag tttgctcatg gaaaacggtg taacaagggt gaacactatc ccatatcacc     9300
agctcaccgt ctttcattgc catacg                                          9326
```

<210> SEQ ID NO 64
<211> LENGTH: 2433
<212> TYPE: DNA
<213> ORGANISM: Artificial
<220> FEATURE:
<223> OTHER INFORMATION: pCRISPR

<400> SEQUENCE: 64

```
ctcgagtccc tatcagtgat agagattgac atccctatca gtgatagaga tactgagcac       60
atcagcagga cgcactgacc gaattcaact caacaagtct cagtgtgctg aagttttggg      120
accattcaaa acagcatagc tctaaaacga gacctttgag cttccgagac tggtctcagt      180
tttgggacca ttcaaaacag catagctcta aaacctcgta gactatttt gtctaaaaaa      240 tttcgtaatc gcactatttg tctcagctag acttcagtct tgaaaagccc ctgtattact      300
gcatttatta agagtattat accatatttt tagttattaa gaaataggat cccatggtac      360
gcgtgctaga ggcatcaaat aaaacgaaag gctcagtcga agactgggc cttcgttt       420 atctgttgtt tgtcggtgaa cgctctcctg agtaggacaa atccgccgcc ctagacctag     480
ggcgttcggc tgcggcgagc ggtatcagct cactcaaagg cggtaatacg gttatccaca     540
gaatcagggg ataacgcagg aaagaacatg tgagcaaaag gccagcaaaa ggccaggaac     600
cgtaaaaagg ccgcgttgct ggcgtttttc cataggctcc gcccccctga cgagcatcac     660
aaaaatcgac gctcaagtca gaggtggcga aacccgacag gactataaag ataccaggcg     720 tttcccctg gaagctccct cgtgcgctct cctgttccga ccctgccgct taccggatac     780
ctgtccgcct ttctcccttc gggaagcgtg gcgctttctc aatgctcacg ctgtaggtat     840
ctcagttcgg tgtaggtcgt tcgctccaag ctgggctgtg tgcacgaacc cccgttcag     900 cccgaccgct gcgccttatc cggtaactat cgtcttgagt ccaacccggt aagacacgac    960
ttatcgccac tggcagcagc cactggtaac aggattagca gagcgaggta tgtaggcggt    1020
gctacagagt tcttgaagtg gtggcctaac tacggctaca ctagaaggac agtatttggt    1080
atctgcgctc tgctgaagcc agttaccttc ggaaaaagag ttggtagctc ttgatccggc    1140
aaacaaacca ccgctggtag cggtggtttt tttgtttgca agcagcagat tacgcgcaga    1200
aaaaaaggat ctcaagaaga tcctttgatc ttttctacgg ggtctgacgc tcagtggaac    1260
```

| | |
|---|---|
| gaaaactcac gttaagggat tttggtcatg actagtgctt ggattctcac caataaaaaa | 1320 |
| cgcccggcgg caaccgagcg ttctgaacaa atccagatgg agttctgagg tcattactgg | 1380 |
| atctatcaac aggagtccaa gcgagctctc gaaccccaga gtcccgctca aagaactcg | 1440 |
| tcaagaaggc gatagaaggc gatgcgctgc gaatcgggag cggcgatacc gtaaagcacg | 1500 |
| aggaagcggt cagcccattc gccgccaagc tcttcagcaa tatcacgggt agccaacgct | 1560 |
| atgtcctgat agcggtccgc cacacccagc cggccacagt cgatgaatcc agaaaagcgg | 1620 |
| ccattttcca ccatgatatt cggcaagcag gcatcgccat gggtcacgac gagatcctcg | 1680 |
| ccgtcgggca tgcgcgcctt gagcctggcg aacagttcgg ctggcgcgag ccctgatgc | 1740 |
| tcttcgtcca gatcatcctg atcgacaaga ccggcttcca tccgagtacg tgctcgctcg | 1800 |
| atgcgatgtt tcgcttggtg gtcgaatggg caggtagccg gatcaagcgt atgcagccgc | 1860 |
| cgcattgcat cagccatgat ggatactttc tcggcaggag caaggtgaga tgacaggaga | 1920 |
| tcctgccccg gcacttcgcc caatagcagc cagtcccttc ccgcttcagt gacaacgtcg | 1980 |
| agcacagctg cgcaaggaac gcccgtcgtg gccagccacg atagccgcgc tgcctcgtcc | 2040 |
| tgcagttcat tcagggcacc ggacaggtcg gtcttgacaa aaagaaccgg gcgcccctgc | 2100 |
| gctgacagcc ggaacacggc ggcatcagag cagccgattg tctgttgtgc ccagtcatag | 2160 |
| ccgaatagcc tctccaccca gcggccggga gaacctgcgt gcaatccatc ttgttcaatc | 2220 |
| atgcgaaacg atcctcatcc tgtctcttga tcagatcttg atccctgcg ccatcagatc | 2280 |
| cttggcggca agaaagccat ccagtttact ttgcagggct tcccaacctt accagagggc | 2340 |
| gccccagctg gcaattccga cgtctaagaa accattatta tcatgacatt aacctataaa | 2400 |
| aataggcgta tcacgaggcc ctttcgtctt cac | 2433 |

<210> SEQ ID NO 65
<211> LENGTH: 2650
<212> TYPE: DNA
<213> ORGANISM: Artificial
<220> FEATURE:
<223> OTHER INFORMATION: pCRRNA

<400> SEQUENCE: 65

| | |
|---|---|
| aagatggcag cgcctaaatg tagaatgata aaaggattaa gagattaatt tccctaaaaa | 60 |
| tgataaaaca agcgttttga aagcgcttgt ttttttggtt tgcagtcaga gtagaataga | 120 |
| agtatcaaaa aaagcaccga ctcggtgcca cttttcaag ttgataacgg actagcctta | 180 |
| ttttaacttg ctatgctgtt ttgaatggtt ccaacaagat tatttataa cttttataac | 240 |
| aaataatcaa ggagaaattc aaagaaattt atcagccata aaacaatact taatactcat | 300 |
| gaattcaact caacaagtct cagtgtgctg aagttttggg accattcaaa acagcatagc | 360 |
| tctaaaacga gacctttgag cttccgagac tggtctcagt tttgggacca ttcaaaacag | 420 |
| catagctcta aaacctcgta gactattttt gtctaaaaaa tttcgtaatc gcactatttg | 480 |
| tctcagctag acttcagtct tgaaaagccc ctgtattact gcatttatta agagtattat | 540 |
| accatatttt tagttattaa gaaataggat cccatggtac gcgtgctaga ggcatcaaat | 600 |
| aaaacgaaag gctcagtcga agactgggc tttcgttttt atctgttgtt tgtcggtgaa | 660 |
| cgctctcctg agtaggacaa atccgccgcc ctagacctag ggcgttcggc tgcggcgagc | 720 |
| ggtatcagct cactcaaagg cggtaatacg gttatccaca gaatcagggg ataacgcagg | 780 |
| aaagaacatg tgagcaaaag gccagcaaaa ggccaggaac cgtaaaaagg ccgcgttgct | 840 |
| ggcgtttttc cataggctcc gcccccctga cgagcatcac aaaaatcgac gctcaagtca | 900 |

```
gaggtggcga aacccgacag gactataaag ataccaggcg tttccccctg gaagctccct    960
cgtgcgctct cctgttccga ccctgccgct taccggatac ctgtccgcct ttctcccttc   1020
gggaagcgtg gcgctttctc aatgctcacg ctgtaggtat ctcagttcgg tgtaggtcgt   1080
tcgctccaag ctgggctgtg tgcacgaacc ccccgttcag cccgaccgct gcgccttatc   1140
cggtaactat cgtcttgagt ccaacccggt aagacacgac ttatcgccac tggcagcagc   1200
cactggtaac aggattagca gagcgaggta tgtaggcgt gctacagagt tcttgaagtg    1260
gtggcctaac tacggctaca ctagaaggac agtatttggt atctgcgctc tgctgaagcc   1320
agttaccttc ggaaaaagag ttggtagctc ttgatccggc aaacaaacca ccgctggtag   1380
cggtggtttt tttgtttgca agcagcagat tacgcgcaga aaaaaaggat ctcaagaaga   1440
tcctttgatc ttttctacgg ggtctgacgc tcagtggaac gaaaactcac gttaagggat   1500
tttggtcatg actagtgctt ggattctcac caataaaaaa cgcccggcgg caaccgagcg   1560
ttctgaacaa atccagatgg agttctgagg tcattactgg atctatcaac aggagtccaa   1620
gcgagctctc gaaccccaga gtcccgctca gaagaactcg tcaagaaggc gatagaaggc   1680
gatgcgctgc gaatcgggag cggcgatacc gtaaagcacg aggaagcggt cagcccattc   1740
gccgccaagc tcttcagcaa tatcacgggt agccaacgct atgtcctgat agcggtccgc   1800
cacacccagc cggccacagt cgatgaatcc agaaaagcgg ccattttcca ccatgatatt   1860
cggcaagcag gcatcgccat gggtcacgac gagatcctcg ccgtcgggca tgcgcgcctt   1920
gagcctggcg aacagttcgg ctggcgcgag cccctgatgc tcttcgtcca gatcatcctg   1980
atcgacaaga ccggcttcca tccgagtacg tgctcgctcg atgcgatgtt tcgcttggtg   2040
gtcgaatggg caggtagccg gatcaagcgt atgcagccgc cgcattgcat cagccatgat   2100
ggatactttc tcggcaggag caaggtgaga tgacaggaga tcctgccccg gcacttcgcc   2160
caatagcagc cagtcccttc ccgcttcagt gacaacgtcg agcacagctg cgcaaggaac   2220
gcccgtcgtg gccagccacg atagccgcgc tgcctcgtcc tgcagttcat tcagggcacc   2280
ggacaggtcg gtcttgacaa aaagaaccgg gcgcccctgc gctgacagcc ggaacacggc   2340
ggcatcagag cagccgattg tctgttgtgc ccagtcatag ccgaatagcc ctccaccca   2400
agcggccgga gaacctgcgt gcaatccatc ttgttcaatc atgcgaaacg atcctcatcc   2460
tgtctcttga tcagatcttg atcccctgcg ccatcagatc cttggcggca agaaagccat   2520
ccagtttact ttgcagggct tcccaacctt accagagggc gccccagctg gcaattccga   2580
cgtctaagaa accattatta tcatgacatt aacctataaa aataggcgta tcacgaggcc   2640
ctttcgtctt                                                          2650
```

<210> SEQ ID NO 66  
<211> LENGTH: 4085  
<212> TYPE: DNA  
<213> ORGANISM: Artificial  
<220> FEATURE:  
<223> OTHER INFORMATION: pLCX

<400> SEQUENCE: 66

```
taaaaatagg cgtatcacga ggcccttttcg tcttcgggcc cattaagttc tgtctcggcg     60
cgtctgcgtc tggctggctg gcataaatat ctcactcgca atcaaattca gccgatagcg    120
gaacgggaag gcgactggag tgccatgtcc ggttttcaac aaaccatgca aatgctgaat    180
gagggcatcg ttcccactgc gatgctggtt gccaacgatc agatggcgct gggcgcaatg    240
```

```
cgcgccatta ccgagtccgg gctgcgcgtt ggtgcggata tctcggtagt gggatacgac    300
gataccgaag acagctcatg ttatatcccg ccgttaacca ccatcaaaca ggattttcgc    360
ctgctggggc aaaccagcgt ggaccgcttg ctgcaactct ctcagggcca ggcggtgaag    420
ggcaatcagc tgttgcccgt ctcactggtg aaaagaaaaa ccaccctggc gcccaatacg    480
caaaccgcct ctccccgcgc gttggccgat tcattaatgc agctggcacg acaggtttcc    540
cgactggaaa gcgggcagtg agcgcaacgc aattaatgtg agttagctca ctcattaggc    600
accccaggct ttacacttta tgcttccggc tcgtatgttg tgtggaattg tgagcggata    660
acaatttcac acaggaaaca gctatgacca tgattacgga ttcactggcc gtcgttttac    720
aacgtcgtga ctgggaaaac cctggcgtta cccaacttaa tcgccttgca gcacatcccc    780
ctttcgccag ctggcgtaat agcgaagagg cccgcaccga tcgcccttcc caacagttgc    840
gcagcctgaa tggcgaatgg cgctttgcct ggtttccggc accagaagcg gtgccggaaa    900
gctggctgga gtgcgatctt cctgaggccg atactgtcgt cgtcccctca aactggcaga    960
tgcacggtta cgatgcgccc atctacacca acgtgaccta tcccattacg gtcaatccgc   1020
cgtttgttcc cacgtagaat ccgacgggtt gttactcgct cacatttaat gttgatgaaa   1080
gctggctaca ggaaggccag acgcgaatta tttttgatgg cgttaactcg gcgtttcatc   1140
tgtggtgcaa cgggcgctgg gtcggttacg gccaggacag tcgtttgccg tctgaatttg   1200
acctgagcgc attttttacgc gccggagaaa accgcctcgc ggtgatggtg ctgcgctgga   1260
gtgacggcag ttatctggaa gatcaggata tgtggcggat gagcggcatt ttccgtgacg   1320
tctcgttgct gcataaaccg actacacaaa tcagcgattt ccatgttgcc actcgcttta   1380
atgatgattt cagccgcgct gtactggagg ctgaagttca gatgtgcggc gagttgcgtg   1440
actacctacg ggtaacagtt tctttatggc agggtgaaac gcaggtcgcc agcggcaccg   1500
cgcctttcgg cggtgaaatt atcgatgagc gtggtggtta tgccgatcgc gtcacactac   1560
gtctgaacgt cgaaaacccg aaactgtgga gcgccgaaat cccgaatctc tatcgtgcgg   1620
tggttgaact gcacaccgcc gacggcacgc tgattgaagc agaagcctgc gatgtcggtt   1680
tccgcgaggt gcggattgaa aatggtctgc tgctgctgaa cggcaagccg ttgctgattc   1740
gaggcgttaa ccgtcacgag catcatcctc tgcatggtca ggtcatggat gagcagacga   1800
tggtgcagga tatcctgctg atgaagcaga acaactttaa cgccgtgcgc tgttcgcatt   1860
atccgaacca tccgctgtgg tacacgctgt gcgaccgcta cggcctgtat gtggtggatg   1920
aagccaatat tgaaacccac ggcatggtgc aatgaatcg tctgaccgat gatccgcgct   1980
ggctaccggc gatgagcgaa cgcgtaacgc gaatggtgca gcgcgatcgt aatcaggatc   2040
ccatggtacg cgtgctagag gcatcaaata aaacgaaagg ctcagtcgaa agactgggcc   2100
tttcgtttta tctgttgttt gtcggtgaac gctctcctga gtaggacaaa tccgccgccc   2160
tagacctagg gcgttcggct gcggcgagcg gtatcagctc actcaaaggc ggtaatacgg   2220
ttatccacag aatcagggga taacgcagga agaacatgt gagcaaaagg ccagcaaaag   2280
gccaggaacc gtaaaaaggc cgcgttgctg gcgttttcc ataggctccg ccccctgac   2340 gagcatcaca aaaatcgacg ctcaagtcag aggtggcgaa acccgacagg actataaaga   2400
taccaggcgt ttccccctgg aagctccctc gtgcgctctc ctgttccgac cctgccgctt   2460
accggatacc tgtccgcctt tctcccttcg ggaagcgtgg cgctttctca atgctcacgc   2520
tgtaggtatc tcagttcggt gtaggtcgtt cgctccaagc tgggctgtgt gcacgaaccc   2580
cccgttcagc ccgaccgctg cgccttatcc ggtaactatc gtcttgagtc aacccggta   2640
```

```
agacacgact tatcgccact ggcagcagcc actggtaaca ggattagcag agcgaggtat    2700
gtaggcggtg ctacagagtt cttgaagtgg tggcctaact acggctacac tagaaggaca    2760
gtatttggta tctgcgctct gctgaagcca gttaccttcg gaaaagagt tggtagctct     2820
tgatccggca aacaaaccac cgctggtagc ggtggttttt ttgtttgcaa gcagcagatt    2880
acgcgcagaa aaaaggatc tcaagaagat cctttgatct tttctacggg gtctgacgct    2940
cagtggaacg aaaactcacg ttaagggatt ttggtcatga ctagtgcttg gattctcacc    3000
aataaaaaac gcccggcggc aaccgagcgt tctgaacaaa tccagatgga gttctgaggt    3060
cattactgga tctatcaaca ggagtccaag cgagctctcg aacccagag tcccgctcag     3120
aagaactcgt caagaaggcg atagaaggcg atgcgctgcg aatcgggagc ggcgataccg    3180
taaagcacga ggaagcggtc agcccattcg ccgccaagct cttcagcaat atcacgggta    3240
gccaacgcta tgtcctgata gcggtccgcc acacccagcc ggccacagtc gatgaatcca    3300
gaaaagcggc catttccac catgatattc ggcaagcagg catcgccatg ggtcacgacg     3360
agatcctcgc cgtcgggcat gcgcgccttg agcctggcga acagttcggc tggcgcgagc    3420
ccctgatgct cttcgtccag atcatcctga tcgacaagac cggcttccat ccgagtacgt    3480
gctcgctcga tgcgatgttt cgcttggtgg tcgaatgggc aggtagccgg atcaagcgta    3540
tgcagccgcc gcattgcatc agccatgatg gatactttct cggcaggagc aaggtgagat    3600
gacaggagat cctgccccgg cacttcgccc aatagcagcc agtcccttcc cgcttcagtg    3660
acaacgtcga gcacagctgc gcaaggaacg cccgtcgtgg ccagccacga tagccgcgct    3720
gcctcgtcct gcagttcatt cagggcaccg gacaggtcgg tcttgacaaa aagaaccggg    3780
cgcccctgcg ctgacagccg gaacacggcg gcatcagagc agccgattgt ctgttgtgcc    3840
cagtcatagc cgaatagcct ctccacccaa gcggccggag aacctgcgtg caatccatct    3900
tgttcaatca tgcgaaacga tcctcatcct gtctcttgat cagatcttga tccctgcgc     3960
catcagatcc ttggcggcaa gaaagccatc cagtttactt tgcagggctt cccaacctta    4020
ccagagggcg ccccagctgg caattccgac gtctaagaaa ccattattat catgacatta    4080
accta                                                                4085
```

<210> SEQ ID NO 67
<211> LENGTH: 2349
<212> TYPE: DNA
<213> ORGANISM: Artificial
<220> FEATURE:
<223> OTHER INFORMATION: psgRNAc

<400> SEQUENCE: 67

```
gaattccgga tgagcattca tcaggcgggc aagaatgtga ataaaggccg gataaaactt     60
gtgcttattt ttctttacgg tctttaaaaa ggccgtaata tccagctgaa cggtctggtt    120
ataggtacat tgagcaactg actgaaatgc ctcaaaatgt tctttacgat gccattggga    180
tatatcaacg gtggtatatc cagtgatttt tttctccatt ttagcttcct tagctcctga    240
aaatctcgat aactcaaaaa atacgcccgg tagtgatctt atttcattat ggtgaaagtt    300
ggaacctctt acgtgccgat caacgtctca ttttcgccaa aagttggccc agggcttccc    360
ggtatcaaca gggacaccag gatttattta ttctgcgaag tgatcttccg tcacaggtat    420
ttattcggcg caaagtgcgt cgggtgatgc tgccaactta ctgatttagt gtatgatggt    480
gttttgagg tgctccagtg cttctgtttt ctatcagctg tccctcctgt tcagctactg    540
```

| | |
|---|---|
| acggggtggt gcgtaacggc aaaagcaccg ccggacatca gcgctagcgg agtgtatact | 600 |
| ggcttactat gttggcactg atgagggtgt cagtgaagtg cttcatgtgg caggagaaaa | 660 |
| aaggctgcac cggtgcgtca gcagaatatg tgatacagga tatattccgc ttcctcgctc | 720 |
| actgactcgc tacgctcggt cgttcgactg cggcgagcgg aaatggctta cgaacggggc | 780 |
| ggagatttcc tggaagatgc caggaagata cttaacaggg aagtgagagg gccgcggcaa | 840 |
| agccgttttt ccataggctc cgccccctg acaagcatca cgaaatctga cgctcaaatc | 900 |
| agtggtggcg aaacccgaca ggactataaa gataccaggc gtttccccct ggcggctccc | 960 |
| tcgtgcgctc tcctgttcct gcctttcggt ttaccggtgt cattccgctg ttatggccgc | 1020 |
| gtttgtctca ttccacgcct gacactcagt tccgggtagg cagttcgctc caagctggac | 1080 |
| tgtatgcacg aaccccccgt tcagtccgac cgctgcgcct tatccggtaa ctatcgtctt | 1140 |
| gagtccaacc cggaaagaca tgcaaaagca ccactggcag cagccactgg taattgattt | 1200 |
| agaggagtta gtcttgaagt catgcgccgg ttaaggctaa actgaaagga caagttttgg | 1260 |
| tgactgcgct cctccaagcc agttacctcg gttcaaagag ttggtagctc agagaaacctt | 1320 |
| cgaaaaaccg ccctgcaagg cggttttttc gttttcagag caagagatta gcgcagacc | 1380 |
| aaaacgatct caagaagatc atcttattaa tcagataaaa tatttctaga tttcagtgca | 1440 |
| atttatctct tcaaatgtag cacctggcta ggaggtgact gaagtatatt ttaggaattc | 1500 |
| taaagatctt tgacagctag ctcagtccta ggtataatac tagttgagac cagtctaggt | 1560 |
| ctcggtttta gagctagaaa tagcaagtta aaataaggct agtccgttat caacttgaaa | 1620 |
| aagtggcacc gagtcggtgc ttttttggt agtgcagcgc gatcgtaatc agggggaga | 1680 |
| gcctgagcaa actggcctca ggcatttgag aagcacacgg tcacactgct tccggtagtc | 1740 |
| aataaaccgg taaccagca atagacataa gcggctattt aacgaccctg ccctgaaccg | 1800 |
| acgaccgggt cgaatttgct ttcgaatttc tgccattcat ccgcttatta tcacttattc | 1860 |
| aggcgtagca ccaggcgttt aagggcacca ataactgcct taaaaaaatt acgccccgcc | 1920 |
| ctgccactca tcgcagtact gttgtaattc attaagcatt ctgccgacat ggaagccatc | 1980 |
| acagacggca tgatgaacct gaatcgccag cggcatcagc accttgtcgc cttgcgtata | 2040 |
| atatttgccc atggtgaaaa cggggggcgaa gaagttgtcc atattggcca cgtttaaatc | 2100 |
| aaaactggtg aaactcaccc agggattggc tgagacgaaa aacatattct caataaaccc | 2160 |
| tttagggaaa taggccaggt tttcaccgta acacgccaca tcttgcgaat atatgtgtag | 2220 |
| aaactgccgg aaatcgtcgt ggtattcact ccagagcgat gaaaacgttt cagtttgctc | 2280 |
| atggaaaacg gtgtaacaag ggtgaacact atcccatatc accagctcac cgtctttcat | 2340 |
| tgccatacg | 2349 |

<210> SEQ ID NO 68
<211> LENGTH: 8701
<212> TYPE: DNA
<213> ORGANISM: Artificial
<220> FEATURE:
<223> OTHER INFORMATION: pPh1F-Cas9

<400> SEQUENCE: 68

| | |
|---|---|
| tcagatcctt ccgtatttag ccagtatgtt ctctagtgtg gttcgttgtt tttgcgtgag | 60 |
| ccatgagaac gaaccattga gatcatactt actttgcatg tcactcaaaa attttgcctc | 120 |
| aaaactggtg agctgaattt ttgcagttaa agcatcgtgt agtgtttttc ttagtccgtt | 180 |
| acgtaggtag gaatctgatg taatggttgt tggtattttg tcaccattca tttttatctg | 240 |

```
gttgttctca agttcggtta cgagatccat ttgtctatct agttcaactt ggaaaatcaa      300
cgtatcagtc gggcggcctc gcttatcaac caccaatttc atattgctgt aagtgtttaa      360
atctttactt attggtttca aaacccattg gttaagcctt ttaaactcat ggtagttatt      420
ttcaagcatt aacatgaact taaattcatc aaggctaatc tctatatttg ccttgtgagt      480
tttcttttgt gttagttctt ttaataacca ctcataaatc ctcatagagt atttgttttc      540
aaaagactta acatgttcca gattatattt tatgaatttt tttaactgga aaagataagg      600
caatatctct tcactaaaaa ctaattctaa ttttttcgctt gagaacttgg catagtttgt      660
ccactggaaa atctcaaagc ctttaaccaa aggattcctg atttccacag ttctcgtcat      720
cagctctctg gttgctttag ctaatacacc ataagcattt tccctactga tgttcatcat      780
ctgagcgtat tggttataag tgaacgatac cgtccgttct ttccttgtag ggttttcaat      840
cgtggggttg agtagtgcca cacagcataa aattagcttg gtttcatgct ccgttaagtc      900
atagcgacta atcgctagtt catttgcttt gaaaacaact aattcagaca tacatctcaa      960
ttggtctagg tgattttaat cactatacca attgagatgg gctagtcaat gataattact     1020
agtccttttc ctttgagttg tgggtatctg taaattctgc tagacctttg ctggaaaact     1080
tgtaaattct gctagaccct ctgtaaattc cgctagacct ttgtgtgttt ttttttgttta    1140 tattcaagtg gttataattt atagaataaa gaaagaataa aaaagataaa aagaatagaa     1200
tcccagccct gtgtataact cactacttta gtcagttccg cagtattaca aaaggatgtc     1260
gcaaacgctg tttgctcctc tacaaaacag accttaaaac cctaaaggct taagtagcac     1320
cctcgcaagc tcggttgcgg ccgcaatcgg gcaaatcgct gaatattcct tttgtctccg     1380
accatcaggc acctgagtcg ctgtctttt cgtgacattc agttcgctgc gctcacggct      1440
ctggcagtga atgggggtaa atggcactac aggcgccttt tatggattca tgcaaggaaa     1500
ctacccataa tacaagaaaa gcccgtcacg ggcttctcag ggcgttttat ggcgggtctg     1560
ctatgtggtg ctatctgact ttttgctgtt cagcagttcc tgccctctga ttttccagtc     1620
tgaccacttc ggattatccc gtgacaggtc attcagactg gctaatgcac ccagtaaggc     1680
agcggtatca tcaacggggt ctgacgctca gtggaacgaa aactcacgtt aagggatttt     1740
ggtcatgaga ttatcaaaaa ggatcttcac ctagatcctt ttaaattaaa aatgaagttt     1800
taaatcaatc taaagtatat atgagtaaac ttggtctgac agttacgttt ccacaaccaa     1860
ttaaccaatt ctgatttaga aaaactcatc gagcatcaaa tgaaactgca atttattcat     1920
atcaggatta tcaataccat attttttgaaa agccgtttc tgtaatgaag gagaaaactc      1980
accgaggcag ttccatagga tggcaagatc ctggtatcgg tctgcgattc cgactcgtcc     2040
aacatcaata caacctatta atttcccctc gtcaaaaata aggttatcaa gtgagaaatc     2100
accatgagtg acgactgaat ccggtgagaa tggcaaaagc ttatgcattt cttttccagac    2160 ttgttcaaca ggccagccat tacgctcgtc atcaaaatca ctcgcatcaa ccaaaccgtt     2220
attcattcgt gattgcgcct gagcgagacg aaatacgcga tcgctgttaa aaggacaatt     2280
acaaacagga atcgaatgca accggcgcag gaacactgcc agcgcatcaa caatatttc      2340 acctgaatca ggatattctt ctaatacctg gaatgctgtt ttcccgggga tcgcagtggt     2400
gagtaaccat gcatcatcag gagtacggat aaaatgcttg atggtcggaa gaggcataaa     2460
ttccgtcagc cagtttagtc tgaccatctc atctgtaaca tcattggcaa cgctaccttt     2520
gccatgtttc agaaacaact ctggcgcatc gggcttccca tacaatcgat agattgtcgc     2580
```

```
acctgattgc ccgacattat cgcgagccca tttatacccca tataaatcag catccatgtt    2640
ggaatttaat cgcggcctcg agcaagacgt ttcccgttga atatggctca taacacccct    2700
tgtattactg tttatgtaag cagacagttt tattgttcat gatgatatat ttttatcttg    2760
tgcaatgtaa catcagagat tttgagacac aacgtggctt tccctgcagg atttcggagg    2820
cctgcgttat cccctgattc tgtggataac cgtattaccg cctttgagtg agctgatacc    2880
gctcgccgca gccgaacgcc caaaaagcc tcgctttcag cacctgtcgt ttcctttctt    2940
ttcagagggt attttaaata aaacattaa gttatgacga agaagaacgg aaacgcctta    3000
aaccggaaaa ttttcataaa tagcgaaaac ccgcgaggtc gccgcccgt aacctgtcgg    3060
atcaccggaa aggacccgta aagtgataat gattatcatc tacatatcac aacgtgcgtg    3120
gagggactag tggattttac ggctagctca gtcctaggta caatgctagc gaattcatta    3180
aagaggagaa aggtacccat ggcacgtacc ccgagccgta gcagcattgg tagcctgcgt    3240
agtccgcata cccataaagc aattctgacc agcaccattg aaatcctgaa agaatgtggt    3300
tatagcggtc tgagcattga aagcgttgca cgtcgtgccg gtgcaagcaa accgaccatt    3360
tatcgttggt ggaccaataa agcagcactg attgccgaag tgtatgaaaa tgaaagcgaa    3420
caggtgcgta aatttccgga tctgggtagc tttaaagccg atctggattt tctgctgcgt    3480
aatctgtgga aagtttggcg tgaaaccatt tgtggtgaag catttcgttg tgttattgca    3540
gaagcacagc tggaccctgc aaccctgacc agctgaaag atcagtttat ggaacgtcgt    3600
cgtgagatgc cgaaaaaact ggttgaaaat gccattagca atggtgaact gccgaaagat    3660
accaatcgtg aactgctgct ggatatgatt tttggttttt gttggtatcg cctgctgacc    3720
gaacagctga ccgttgaaca ggatattgaa gaatttacct tcctgctgat taatggtgtt    3780
tgtccgggta cacagcgtta actagggccc atacccccaa ttattgaagg ccgctaacgc    3840
ggcctttttt tgtttctggt ctgcccgacg tacggtgaat ctgattcgtt accaattgac    3900
atgatacgaa acgtaccgta tcgttaaggt tactagagat taaagaggag aaatactaga    3960
tggataagaa atactcaata ggcttagata tcggcacaaa tagcgtcgga tgggcggtga    4020
tcactgatga atataaggtt ccgtctaaaa agttcaaggt tctgggaaat acagaccgcc    4080
acagtatcaa aaaaaatctt atagggctc ttttatttga cagtggagag acagcggaag    4140
cgactcgtct caaacggaca gctcgtagaa ggtatacacg tcggaagaat cgtatttgtt    4200
atctacagga gattttttca aatgagatgg cgaaagtaga tgatagtttc tttcatcgac    4260
ttgaagagtc ttttttggtg gaagaagaca agaagcatga acgtcatcct atttttggaa    4320
atatagtaga tgaagttgct tatcatgaga atatccaac tatctatcat ctgcgaaaaa    4380
aattggtaga ttctactgat aaagcggatt tgcgcttaat ctatttggcc ttagcgcata    4440
tgattaagtt tcgtggtcat tttttgattg agggagattt aaatcctgat aatagtgatg    4500
tggacaaact atttatccag ttggtacaaa cctacaatca attatttgaa gaaaacccta    4560
ttaacgcaag tggagtagat gctaaagcga ttctttctgc acgattgagt aaatcaagac    4620
gattagaaaa tctcattgct cagctccccg gtgagaagaa aaatggctta tttgggaatc    4680
tcattgcttt gtcattgggt ttgacccta attttaaatc aaattttgat ttggcagaag    4740
atgctaaatt acagctttca aaagatactt acgatgatga tttagataat ttattggcgc    4800
aaattggaga tcaatatgct gatttgtttt tggcagctaa gaatttatca gatgctattt    4860
tactttcaga tatcctaaga gtaaatactg aaataactaa ggctcccta tcagcttcaa    4920
tgattaaacg ctacgatgaa catcatcaag acttgactct tttaaaagct ttagttcgac    4980
```

```
aacaacttcc agaaaagtat aaagaaatct tttttgatca atcaaaaaac ggatatgcag   5040
gttatattga tgggggagct agccaagaag aattttataa atttatcaaa ccaattttag   5100
aaaaaatgga tggtactgag gaattattgg tgaaactaaa tcgtgaagat ttgctgcgca   5160
agcaacggac ctttgacaac ggctctattc cccatcaaat tcacttgggt gagctgcatg   5220
ctattttgag aagacaagaa gacttttatc cattttaaaa agacaatcgt gagaagattg   5280
aaaaaatctt gacttttcga attccttatt atgttggtcc attggcgcgt ggcaatagtc   5340
gttttgcatg gatgactcgg aagtctgaag aaacaattac cccatggaat tttgaagaag   5400
ttgtcgataa aggtgcttca gctcaatcat ttattgaacg catgacaaac tttgataaaa   5460
atcttccaaa tgaaaagta ctaccaaaac atagtttgct ttatgagtat tttacggttt   5520
ataacgaatt gacaaaggtc aaatatgtta ctgaaggaat gcgaaaacca gcatttcttt   5580
caggtgaaca gaagaaagcc attgttgatt tactcttcaa aacaaatcga aaagtaaccg   5640
ttaagcaatt aaaagaagat tatttcaaaa aaatagaatg ttttgatagt gttgaaattt   5700
caggagttga agatagattt aatgcttcat taggtaccta ccatgatttg ctaaaaatta   5760
ttaaagataa agattttttg gataatgaag aaaatgaaga tatcttagag gatattgttt   5820
taacattgac cttatttgaa gatagggaga tgattgagga aagacttaaa acatatgctc   5880
acctctttga tgataaggtg atgaaacagc ttaaacgtcg ccgttatact ggttggggac   5940
gtttgtctcg aaaattgatt aatggtatta gggataagca atctggcaaa acaatattag   6000 atttttgaa atcagatggt tttgccaatc gcaattttat gcagctgatc catgatgata   6060
gtttgacatt taagaagac attcaaaaag cacaagtgtc tggacaaggc gatagtttac   6120
atgaacatat tgcaaattta gctggtagcc ctgctattaa aaaaggtatt ttacagactg   6180
taaaagttgt tgatgaattg gtcaaagtaa tggggcggca taagccagaa aatatcgtta   6240
ttgaaatggc acgtgaaaat cagacaactc aaaagggcca gaaaaattcg cgagagcgta   6300
tgaaacgaat cgaagaaggt atcaaagaat taggaagtca gattcttaaa gagcatcctg   6360
ttgaaaatac tcaattgcaa aatgaaaagc tctatctcta ttatctccaa aatggaagag   6420
acatgtatgt ggaccaagaa ttagatatta atcgtttaag tgattatgat gtcgatcaca   6480
ttgttccaca aagtttcctt aaagacgatt caatagacaa taaggtctta acgcgttctg   6540
ataaaaatcg tggtaaatcg gataacgttc caagtgaaga agtagtcaaa aagatgaaaa   6600
actattggag acaacttcta aacgccaagt taatcactca acgtaagttt gataatttaa   6660
cgaaagctga acgtggaggt ttgagtgaac ttgataaagc tggttttatc aaacgccaat   6720
tggttgaaac tcgccaaatc actaagcatg tggcacaaat tttggatagt cgcatgaata   6780
ctaaatacga tgaaaatgat aaacttattc gagaggttaa agtgattacc ttaaaatcta   6840
aattagtttc tgacttccga aaagattttc aattctataa agtacgtgag attaacaatt   6900
accatcatgc ccatgatgcg tatctaaatg ccgtcgttgg aactgctttg attaagaaat   6960
atccaaaact tgaatcggag tttgtctatg gtgattataa agtttatgat gttcgtaaaa   7020
tgattgctaa gtctgagcaa gaaataggca aagcaaccgc aaaatatttc ttttactcta   7080
atatcatgaa cttcttcaaa acagaaatta cacttgcaaa tggagagatt cgcaaacgcc   7140
ctctaatcga aactaatggg gaaactggag aaattgtctg ggataaaggg cgagattttg   7200
ccacagtgcg caaagtattg tccatgcccc aagtcaatat tgtcaagaaa acagaagtac   7260
agacaggcgg attctccaag gagtcaattt taccaaaaag aaattcggac aagcttattg   7320
```

```
ctcgtaaaaa agactgggat ccaaaaaaat atggtggttt tgatagtcca acggtagctt    7380
attcagtcct agtggttgct aaggtggaaa aagggaaatc gaagaagtta aaatccgtta    7440
aagagttact agggatcaca attatggaaa gaagttcctt tgaaaaaaat ccgattgact    7500
ttttagaagc taaaggatat aaggaagtta aaaaagactt aatcattaaa ctacctaaat    7560
atagtctttt tgagttagaa aacggtcgta aacggatgct ggctagtgcc ggagaattac    7620
aaaaaggaaa tgagctggct ctgccaagca aatatgtgaa ttttttatat ttagctagtc    7680
attatgaaaa gttgaagggt agtccagaag ataacgaaca aaaacaattg tttgtggagc    7740
agcataagca ttatttagat gagattattg agcaaatcag tgaattttct aagcgtgtta    7800
ttttagcaga tgccaattta gataaagttc ttagtgcata taacaaacat agagacaaac    7860
caatacgtga acaagcagaa aatattattc atttatttac gttgacgaat cttggagctc    7920
ccgctgcttt taaatatttt gatacaacaa ttgatcgtaa acgatatacg tctacaaaag    7980
aagttttaga tgccactctt atccatcaat ccatcactgg tctttatgaa acacgcattg    8040
atttgagtca gctaggaggt gactaactcg agtaaggatc tccaggcatt gcaggcatgc    8100
ctcgagatgc atggcgccta acctaaactg atgacgcatc ctcacgataa tatccgggta    8160
ggcgcaatca ctttcgtcta ctccgttaca aagcgaggct gggtatttcc cggccttttct   8220 gttatccgaa atccactgaa agcacagcgg ctggctgagg agataaataa taaacgaggg    8280
gctgtatgca caaagcatct tctgttgagt taagaacgag tatcgagatg gcacatagcc    8340
ttgctcaaat tggaatcagg tttgtgccaa taccagtaga acagacgaa gaatccatgg    8400 gtatggacag atctcaaaaa aagcaccgac tcggtgccac tttttcaagt tgataacgga    8460
ctagccttat tttaacttgc tatttctagc tctaaaacgg ttttcccag tcacgacgtg    8520 ctagcattat acctaggact gagctagctg tcagccattc gatggtgtca acgtaaatgc    8580
atgccgctcg ccttccatgg gtatggacag ttttccctt gatatgtaac ggtgaacagt    8640
tgttctactt tgtttgtta gtcttgatgc ttcactgata gatacaagag ccataagaac    8700
c                                                                    8701
```

<210> SEQ ID NO 69
<211> LENGTH: 4083
<212> TYPE: DNA
<213> ORGANISM: Artificial Sequence
<220> FEATURE:
<223> OTHER INFORMATION: pBAD-MuGam
<220> FEATURE:
<221> NAME/KEY: misc_feature
<222> LOCATION: (2566)..(2595)
<223> OTHER INFORMATION: n is a, c, g, or t

<400> SEQUENCE: 69

```
aaaatctcga taactcaaaa aatacgcccg gtagtgatct tatttcatta tggtgaaagt     60
tggaacctct tacgtgccga tcaacgtctc attttcgcca aaagttggcc cagggcttcc    120
cggtatcaac agggacacca ggatttattt attctgcgaa gtgatcttcc gtcacaggta    180
tttattcggc gcaaagtgcg tcgggtgatg ctgccaactt actgatttag tgtatgatgg    240
tgtttttgag gtgctccagt ggcttctgtt tctatcagct gtccctcctg ttcagctact    300
gacggggtgg tgcgtaacgg caaaagcacc gccggacatc agcgctagcg gagtgtatac    360
tggcttacta gttggcact gatgagggtg tcagtgaagt gcttcatgtg gcaggagaaa    420
aaaggctgca ccggtgcgtc agcagaatat gtgatacagg atatattccg cttcctcgct    480
cactgactcg ctacgctcgg tcgttcgact gcggcgagcg gaaatggctt acgaacgggg    540
```

-continued

```
cggagatttc ctggaagatg ccaggaagat acttaacagg gaagtgagag ggccgcggca    600
aagccgtttt tccataggct ccgcccccct gacaagcatc acgaaatctg acgctcaaat    660
cagtggtggc gaaacccgac aggactataa agataccagg cgtttccccc tggcggctcc    720
ctcgtgcgct ctcctgttcc tgcctttcgg tttaccggtg tcattccgct gttatggccg    780
cgtttgtctc attccacgcc tgacactcag ttccgggtag gcagttcgct ccaagctgga    840
ctgtatgcac gaaccccccg ttcagtccga ccgctgcgcc ttatccggta actatcgtct    900
tgagtccaac ccggaaagac atgcaaaagc accactggca gcagccactg gtaattgatt    960
tagaggagtt agtcttgaag tcatgcgccg gttaaggcta aactgaaagg acaagttttg   1020
gtgactgcgc tcctccaagc cagttacctc ggttcaaaga gttggtagct cagagaacct   1080
tcgaaaaacc gccctgcaag gcggtttttt cgttttcaga gcaagagatt acgcgcagac   1140
caaaacgatc tcaagaagat catcttatta atcagataaa atatttctag atttcagtgc   1200
aatttatctc ttcaaatgta gcacctgaag tcagccccat acgatataag ttgtatcgat   1260
gcataatgtg cctgtcaaat ggacgaagca gggattctgc aaaccctatg ctactccgtc   1320
aagccgtcaa ttgtctgatt cgttaccaat tatgacaact tgacggctac atcattcact   1380
ttttcttcac aaccggcacg gaactcgctc gggctggccc cggtgcattt tttaaatacc   1440
cgcgagaaat agagttgatc gtcaaaacca acattgcgac cgacggtggc gataggcatc   1500
cgggtggtgc tcaaaagcag cttcgcctgg ctgatacgtt ggtcctcgcg ccagcttaag   1560
acgctaatcc ctaactgctg gcggaaaaga tgtgacagac gcgacggcga caagcaaaca   1620
tgctgtgcga cgctggcgat atcaaaattg ctgtctgcca ggtgatcgct gatgtactga   1680
caagcctcgc gtacccgatt atccatcggt ggatggagcg actcgttaat cgcttccatg   1740
cgccgcagta acaattgctc aagcagattt atcgccagca gctccgaata gcgcccttcc   1800
ccttgcccgg cgttaatgat ttgcccaaac aggtcgctga aatgcggctg gtgcgcttca   1860
tccgggcgaa agaaccccgt attggcaaat attgacggcc agttaagcca ttcatgccag   1920
taggcgcgcg gacgaaagta aacccactgg tgataccatt cgcgagcctc cggatgacga   1980
ccgtagtgat gaatctctcc tggcgggaac agcaaaatat cacccggtcg gcaaacaaat   2040
tctcgtccct gatttttcac caccccctga ccgcgaatgg tgagattgag aatataacct   2100

ttcattccca gcggtcggtc gataaaaaaa tcgagataac cgttggcctc aatcggcgtt   2160
aaacccgcca ccagatgggc attaaacgag tatcccggca gcaggggatc attttgcgct   2220
tcagccatac ttttcatact cccgccattc agagaagaaa ccaattgtcc atattgcatc   2280
agacattgcc gtcactgcgt cttttactgg ctcttctcgc taaccaaacc ggtaaccccg   2340
cttattaaaa gcattctgta acaaagcggg accaaagcca tgacaaaaac gcgtaacaaa   2400
agtgtctata atcacggcag aaaagtccac attgattatt tgcacggcgt cacactttgc   2460
tatgccatag catttttatc cataagatta gcggatccta cctgacgctt tttatcgcaa   2520
ctctctactg tttctccata cccgtttttt tgggctagcg aattcnnnnn nnnnnnnnnn   2580
nnnnnnnnnn nnnnnatggc taaaccagca aaacgtatca agagtgccgc agcggcttat   2640
gtgccacaaa accgcgatgc ggtgattacc gatattaaac gcatcgggga tttacagcgc   2700
gaagcatcac gtctggaaac ggaaatgaat gatgccatcg cggaaattac ggagaaattt   2760
gcggcccgga ttgcaccgat taaaaccgat attgaaaccc tttcaaaagg cgttcaggga   2820
tggtgtgaag cgaaccgcga cgaactgacg aacggcggca aagtgaagac ggcgaatctt   2880
```

```
gtcaccggtg atgtatcgtg gcgggtccgt ccaccatcag taagtattcg tggtatggat    2940
gcagtgatgg aaacgctgga gcgtcttggc ctgcaacgct ttattcgcac gaagcaggaa    3000
atcaacaagg aagcgatttt actggaaccg aaagcggtcg caggcgttgc cggaattaca    3060
gttaaatcag gcattgagga ttttctatt attccatttg aacaggaagc cggtatttaa    3120
taatttccc gccctcaaaa aagcaataaa gcggctcaat agccgcttta ttcacatcag    3180
caaaaattat atcgggtagc accagaagca cacggtcaca ctgcttccgg tagtcaataa    3240
accggtaaac cagcaataga cataagcggc tatttaacga ccctgccctg aaccgacgac    3300
cgggtcgaat ttgctttcga atttctgcca ttcatccgct tattatcact tattcaggcg    3360
tagcaccagg cgtttaaggg caccaataac tgccttaaaa aaattacgcc ccgccctgcc    3420
actcatcgca gtactgttgt aattcattaa gcattctgcc gacatggaag ccatcacaga    3480
cggcatgatg aacctgaatc gccagcggca tcagcacctt gtcgccttgc gtataatatt    3540
tgcccatggt gaaacggggg cgaagaagt tgtccatatt ggccacgttt aaatcaaaac    3600
tggtgaaact cacccaggga ttggctgaga cgaaaaacat attctcaata aacccttag    3660
ggaaataggc caggttttca ccgtaacacg ccacatcttg cgaatatatg tgtagaaact    3720
gccgaaaatc gtcgtggtat tcactccaga gcgatgaaaa cgtttcagtt tgctcatgga    3780
aaacggtgta acaagggtga acactatccc atatccaccag ctcaccgtct ttcattgcca    3840
tacgaattc cggatgagca ttcatcaggc gggcaagaat gtgaataaag gccggataaa    3900
acttgtgctt attttctt acggtcttta aaaggccgt aatatccagc tgaacggtct    3960
ggttataggt acattgagca actgactgaa atgcctcaaa atgttcttta cgatgccatt    4020
gggatatatc aacggtggta tatccagtga ttttttctc cattttagct tccttagctc    4080
ctg                                                                  4083

<210> SEQ ID NO 70
<211> LENGTH: 3979
<212> TYPE: DNA
<213> ORGANISM: artificial
<220> FEATURE:
<223> OTHER INFORMATION: pBAD-LambdaGam
<220> FEATURE:
<221> NAME/KEY: misc_feature
<222> LOCATION: (2570)..(2599)
<223> OTHER INFORMATION: n is a, c, g, or t

<400> SEQUENCE: 70
aaaatctcga taactcaaaa aatacgcccg gtagtgatct tatttcatta tggtgaaagt      60
tggaacctct tacgtgccga tcaacgtctc attttcgcca aaagttggcc cagggcttcc    120
cggtatcaac agggacacca ggatttattt attctgcgaa gtgatcttcc gtcacaggta    180
tttattcggc gcaaagtgcg tcgggtgatg ctgccaactt actgatttag tgtatgatgg    240
tgtttttgag gtgctccagt ggcttctgtt tctatcagct gtccctcctg ttcagctact    300
gacggggtgg tgcgtaacgg caaaagcacc gccggacatc agcgctagcg gagtgtatac    360
tggcttacta tgttggcact gatgagggtg tcagtgaagt gcttcatgtg gcaggagaaa    420
aaaggctgca ccggtgcgtc agcagaatat gtgatacagg atatattccg cttcctcgct    480
cactgactcg ctacgctcgg tcgttcgact gcggcgagcg gaaatggctt acgaacgggg    540
cggagatttc ctggaagatg ccaggaagat acttaacagg gaagtgagag gccgcggca    600
aagccgtttt tccataggct ccgcccccct gacaagcatc acgaaatctg acgctcaaat    660
cagtggtggc gaaacccgac aggactataa agataccagg cgtttccccc tggcggctcc    720
```

```
ctcgtgcgct ctcctgttcc tgcctttcgg tttaccggtg tcattccgct gttatggccg      780
cgtttgtctc attccacgcc tgacactcag ttccgggtag gcagttcgct ccaagctgga      840
ctgtatgcac gaaccccccg ttcagtccga ccgctgcgcc ttatccggta actatcgtct      900
tgagtccaac ccggaaagac atgcaaaagc accactggca gcagccactg gtaattgatt      960
tagaggagtt agtcttgaag tcatgcgccg gttaaggcta aactgaaagg acaagttttg     1020
gtgactgcgc tcctccaagc cagttacctc ggttcaaaga gttggtagct cagagaacct     1080
tcgaaaaacc gccctgcaag gcggttttt cgttttcaga gcaagagatt acgcgcagac     1140
caaaacgatc tcaagaagat catcttatta atcagataaa atatttctag atttcagtgc     1200
aatttatctc ttcaaatgta gcacctgaag tcagccccat acgatataag ttgtatcgat     1260
gcataatgtg cctgtcaaat ggacgaagca gggattctgc aaaccctatg ctactccgtc     1320
aagccgtcaa ttgtctgatt cgttaccaat tatgacaact tgacggctac atcattcact     1380 tttcttcac aaccggcacg gaactcgctc gggctggccc cggtgcattt tttaaatacc     1440
cgcgagaaat agagttgatc gtcaaaacca acattgcgac cgacggtggc gataggcatc     1500
cgggtggtgc tcaaaagcag cttcgcctgg ctgatacgtt ggtcctcgcg ccagcttaag     1560
acgctaatcc ctaactgctg gcggaaaaga tgtgacagac gcgacggcga caagcaaaca     1620
tgctgtgcga cgctggcgat atcaaaattg ctgtctgcca ggtgatcgct gatgtactga     1680
caagcctcgc gtacccgatt atccatcggt ggatggagcg actcgttaat cgcttccatg     1740
cgccgcagta acaattgctc aagcagattt atcgccagca gctccgaata gcgcccttcc     1800
ccttgcccgg cgttaatgat tgcccaaac aggtcgctga atgcggctg gtgcgcttca     1860 tccgggcgaa agaaccccgt attggcaaat attgacggcc agttaagcca ttcatgccag     1920
taggcgcgcg gacgaaagta aacccactgg tgataccatt cgcgagcctc cggatgacga     1980
ccgtagtgat gaatctctcc tggcgggaac agcaaaatat cacccggtcg gcaaacaaat     2040
tctcgtccct gattttcac caccccctga ccgcgaatgg tgagattgag aatataaccct    2100 ttcattccca gcggtcggtc gataaaaaaa tcgagataac cgttggcctc aatcggcgtt     2160
aaacccgcca ccagatgggc attaaacgag tatcccggca gcaggggatc attttgcgct     2220
tcagccatac tttcatact cccgccattc agagaagaaa ccaattgtcc atattgcatc     2280
agacattgcc gtcactgcgt cttttactgg ctcttctcgc taaccaaacc ggtaaccccg     2340
cttattaaaa gcattctgta acaaagcggg accaaagcca tgacaaaaac gcgtaacaaa     2400
agtgtctata atcacggcag aaaagtccac attgattatt gcacggcgt cacactttgc     2460 tatgccatag catttttatc cataagatta gcggatccta cctgacgctt tttatcgcaa     2520
ctctctactg tttctccata cccgtttttt tgggctagcg aattcgagcn nnnnnnnnn     2580 nnnnnnnnn nnnnnnnnna tggatattaa tactgaaact gagatcaagc aaaagcattc     2640
actaaccccc tttcctgttt tcctaatcag cccggcattt cgcgggcgat atttcacag     2700 ctatttcagg agttcagcca tgaacgctta ttacattcag gatcgtcttg aggctcagag     2760
ctgggcgcgt cactaccagc agctcgcccg tgaagagaaa gaggcagaac tggcagacga     2820 catgaaaaa ggcctgcccc agcacctgtt tgaatcgcta tgcatcgatc atttgcaacg     2880
ccacggggcc agcaaaaaat ccattacccg tgcgtttgat gacgatgttg agtttcagga     2940
gcgcatggca gaacacatcc ggtacatggt tgaaaccatt gctcaccacc aggttgatat     3000
tgattcagag gtataataat tttcccgccc tcaaaaaagc aataaagcgg ctcaatagcc     3060
```

```
gctttattca catcagcaaa aattatatcg ggtagcacca gaagcacacg gtcacactgc      3120
ttccggtagt caataaaccg gtaaaccagc aatagacata agcggctatt taacgaccct      3180
gccctgaacc gacgaccggg tcgaatttgc tttcgaattt ctgccattca tccgcttatt      3240
atcacttatt caggcgtagc accaggcgtt taagggcacc aataactgcc ttaaaaaaat      3300
tacgccccgc cctgccactc atcgcagtac tgttgtaatt cattaagcat tctgccgaca      3360
tggaagccat cacagacggc atgatgaacc tgaatcgcca gcggcatcag caccttgtcg      3420
ccttgcgtat aatatttgcc catggtgaaa acggggcga agaagttgtc catattggcc       3480
acgtttaaat caaaactggt gaaactcacc cagggattgg ctgagacgaa aaacatattc      3540
tcaataaacc ctttagggaa ataggccagg ttttcaccgt aacacgccac atcttgcgaa      3600
tatatgtgta gaaactgccg gaaatcgtcg tggtattcac tccagagcga tgaaaacgtt      3660
tcagtttgct catggaaaac ggtgtaacaa gggtgaacac tatcccatat caccagctca      3720
ccgtctttca ttgccatacg gaattccgga tgagcattca tcaggcgggc aagaatgtga      3780
ataaaggccg gataaaactt gtgcttattt ttctttacgg tctttaaaaa ggccgtaata      3840
tccagctgaa cggtctggtt ataggtacat tgagcaactg actgaaatgc ctcaaaatgt      3900
tctttacgat gccattggga tatatcaacg gtggtatatc cagtgatttt tttctccatt      3960
ttagcttcct tagctcctg                                                   3979

<210> SEQ ID NO 71
<211> LENGTH: 10701
<212> TYPE: DNA
<213> ORGANISM: Artificial
<220> FEATURE:
<223> OTHER INFORMATION: pCas9-MuGam
<220> FEATURE:
<221> NAME/KEY: misc_feature
<222> LOCATION: (9946)..(9976)
<223> OTHER INFORMATION: n is a, c, g, or t

<400> SEQUENCE: 71
tcagatcctt ccgtatttag ccagtatgtt ctctagtgtg gttcgttgtt tttgcgtgag        60
ccatgagaac gaaccattga gatcatactt actttgcatg tcactcaaaa attttgcctc       120
aaaactggtg agctgaattt ttgcagttaa agcatcgtgt agtgttttc ttagtccgtt        180 acgtaggtag gaatctgatg taatggttgt tggtattttg tcaccattca ttttttatctg     240 gttgttctca agttcggtta cgagatccat ttgtctatct agttcaactt ggaaaatcaa      300
cgtatcagtc gggcggcctc gcttatcaac caccaatttc atattgctgt aagtgtttaa      360
atctttactt attggtttca aaacccattg gttaagcctt ttaaactcat ggtagttatt     420
ttcaagcatt aacatgaact taaattcatc aaggctaatc tctatatttg ccttgtgagt     480 tttctttgt gttagttctt ttaataacca ctcataaatc ctcatagagt atttgttttc      540
aaaagactta acatgttcca gattatattt tatgaatttt tttaactgga aaagataagg     600
caatatctct tcactaaaaa ctaattctaa ttttttcgctt gagaacttgg catagtttgt    660
ccactggaaa atctcaaagc ctttaaccaa aggattcctg atttccacag ttctcgtcat     720
cagctctctg gttgctttag ctaatacacc ataagcattt tccctactga tgttcatcat     780
ctgagcgtat tggttataag tgaacgatac cgtccgttct ttccttgtag ggttttcaat    840 cgtgggggttg agtagtgcca cacagcataa aattagcttg gtttcatgct ccgttaagtc    900
atagcgacta atcgctagtt catttgcttt gaaaacaact aattcagaca tacatctcaa     960
ttggtctagg tgattttaat cactatacca attgagatgg gctagtcaat gataattact    1020
```

```
agtcctttc   ctttgagttg   tgggtatctg   taaattctgc   tagacctttg   ctggaaaact   1080
tgtaaattct   gctagaccct   ctgtaaattc   cgctagacct   ttgtgtgttt   tttttgttta   1140
tattcaagtg   gttataattt   atagaataaa   gaaagaataa   aaaagataa    aaagaataga   1200
tcccagccct   gtgtataact   cactacttta   gtcagttccg   cagtattaca   aaaggatgtc   1260
gcaaacgctg   tttgctcctc   tacaaaacag   accttaaaac   cctaaaggct   taagtagcac   1320
cctcgcaagc   tcggttgcgg   ccgcaatcgg   gcaaatcgct   gaatattcct   tttgtctccg   1380
accatcaggc   acctgagtcg   ctgtcttttt   cgtgacattc   agttcgctgc   gctcacggct   1440
ctggcagtga   atgggggtaa   atggcactac   aggcgccttt   tatggattca   tgcaaggaaa   1500
ctacccataa   tacaagaaaa   gcccgtcacg   ggcttctcag   ggcgtttat    ggcgggtctg   1560
ctatgtggtg   ctatctgact   ttttgctgtt   cagcagttcc   tgccctctga   ttttccagtc   1620
tgaccacttc   ggattatccc   gtgacaggtc   attcagactg   gctaatgcac   ccagtaaggc   1680
agcggtatca   tcaacggggt   ctgacgctca   gtggaacgaa   aactcacgtt   aagggatttt   1740
ggtcatgaga   ttatcaaaaa   ggatcttcac   ctagatcctt   ttaaattaaa   aatgaagttt   1800
taaatcaatc   taaagtatat   atgagtaaac   ttggtctgac   agttacgttt   ccacaaccaa   1860
ttaaccaatt   ctgatttaga   aaactcatc    gagcatcaaa   tgaaactgca   atttattcat   1920
atcaggatta   tcaataccat   attttttgaaa   aagccgtttc   tgtaatgaag   gagaaaactc   1980
accgaggcag   ttccatagga   tggcaagatc   ctggtatcgg   tctgcgattc   cgactcgtcc   2040
aacatcaata   caacctatta   atttcccctc   gtcaaaaata   aggttatcaa   gtgagaaatc   2100
accatgagtg   acgactgaat   ccggtgagaa   tggcaaaagc   ttatgcattt   ctttccagac   2160
ttgttcaaca   ggccagccat   tacgctcgtc   atcaaaatca   ctcgcatcaa   ccaaaccgtt   2220
attcattcgt   gattgcgcct   gagcgagacg   aaatacgcga   tcgctgttaa   aaggacaatt   2280
acaaacagga   atcgaatgca   accggcgcag   gaacactgcc   agcgcatcaa   caatattttc   2340
acctgaatca   ggatattctt   ctaataccctg   gaatgctgtt   ttcccgggga   tcgcagtggt   2400
gagtaaccat   gcatcatcag   gagtacggat   aaaatgcttg   atggtcggaa   gaggcataaa   2460
ttccgtcagc   cagtttagtc   tgaccatctc   atctgtaaca   tcattggcaa   cgctaccttt   2520
gccatgtttc   agaaacaact   ctggcgcatc   gggcttccca   tacaatcgat   agattgtcgc   2580
acctgattgc   ccgacattat   cgcgagccca   tttatatccca   tataaatcag   catccatgtt   2640
ggaatttaat   cgcggcctcg   agcaagacgt   ttcccgttga   atatggctca   taacaccccct   2700
tgtattactg   tttatgtaag   cagacagttt   tattgttcat   gatgatatat   ttttatcttg   2760
tgcaatgtaa   catcagagat   tttgagacac   aacgtggctt   tccctgcagg   atttcggagg   2820
cctgcgttat   ccctgattc    tgtggataac   cgtattaccg   cctttgagtg   agctgatacc   2880
gctcgccgca   gccgaacgcc   ccaaaaagcc   tcgctttcag   cacctgtcgt   tcctttctt    2940
ttcagagggt   atttttaaata   aaacattaa    gttatgacga   agaagaacgg   aaacgcctta   3000
aaccggaaaa   ttttcataaa   tagcgaaaac   ccgcgaggtc   gccgcccgt    aacctgtcgg   3060
atcaccggaa   aggacccgta   aagtgataat   gattatcatc   tacatatcac   aacgtgcgtg   3120
gagggactag   tggattttac   ggctagctca   gtcctaggta   caatgctagc   gaattcatta   3180
aagaggagaa   aggtacccat   ggcacgtacc   ccgagccgta   gcagcattgg   tagcctgcgt   3240
agtccgcata   cccataaagc   aattctgacc   agcaccattg   aaatcctgaa   agaatgtggt   3300
tatagcggtc   tgagcattga   aagcgttgca   cgtcgtgccg   gtgcaagcaa   accgaccatt   3360
```

-continued

```
tatcgttggt ggaccaataa agcagcactg attgccgaag tgtatgaaaa tgaaagcgaa    3420
caggtgcgta aatttccgga tctgggtagc tttaaagccg atctggattt tctgctgcgt    3480
aatctgtgga aagtttggcg tgaaaccatt tgtggtgaag catttcgttg tgttattgca    3540
gaagcacagc tggaccctgc aaccctgacc cagctgaaag atcagtttat ggaacgtcgt    3600
cgtgagatgc cgaaaaaact ggttgaaaat gccattagca atggtgaact gccgaaagat    3660
accaatcgtg aactgctgct ggatatgatt tttggttttt gttggtatcg cctgctgacc    3720
gaacagctga ccgttgaaca ggatattgaa gaatttacct tcctgctgat taatggtgtt    3780
tgtccgggta cacagcgtta actagggccc atacccccaa ttattgaagg ccgctaacgc    3840
ggcctttttt tgtttctggt ctgcccgacg tacggtgaat ctgattcgtt accaattgac    3900
atgatacgaa acgtaccgta tcgttaaggt tactagagat aaagaggag aaatactaga    3960 tggataagaa atactcaata ggcttagata tcggcacaaa tagcgtcgga tgggcggtga    4020
tcactgatga atataaggtt ccgtctaaaa agttcaaggt tctgggaaat acagaccgcc    4080
acagtatcaa aaaaaatctt atagggctc ttttatttga cagtggagag acagcggaag    4140
cgactcgtct caaacggaca gctcgtagaa ggtatacacg tcggaagaat cgtatttgtt    4200
atctacagga gattttttca aatgagatgg cgaaagtaga tgatagtttc tttcatcgac    4260
ttgaagagtc ttttttggtg gaagaagaca agaagcatga acgtcatcct attttttggaa    4320 atatagtaga tgaagttgct tatcatgaga aatatccaac tatctatcat ctgcgaaaaa    4380
aattggtaga ttctactgat aaagcggatt tgcgcttaat ctatttggcc ttagcgcata    4440
tgattaagtt tcgtggtcat tttttgattg agggagattt aaatcctgat aatagtgatg    4500 tggacaaaact atttatccag ttggtacaaa cctacaatca attatttgaa gaaaacccta    4560
ttaacgcaag tggagtagat gctaaagcga ttctttctgc acgattgagt aaatcaagac    4620
gattagaaaa tctcattgct cagctccccg gtgagaagaa aaatggctta tttgggaatc    4680
tcattgcttt gtcattgggt ttgaccccta attttaaatc aaattttgat ttggcagaag    4740
atgctaaatt acagctttca aaagatactt acgatgatga tttagataat ttattggcgc    4800
aaattggaga tcaatatgct gatttgtttt tggcagctaa gaatttatca gatgctattt    4860
tactttcaga tatcctaaga gtaaatactg aaataactaa ggctcccta tcagcttcaa    4920 tgattaaacg ctacgatgaa catcatcaag acttgactct tttaaaagct ttagttcgac    4980
aacaacttcc agaaaagtat aaagaaatct tttttgatca atcaaaaaac ggatatgcag    5040
gttatattga tggggagct agccaagaag aattttataa atttatcaaa ccaatttttag    5100 aaaaaatgga tggtactgag gaattattgg tgaaactaaa tcgtgaagat ttgctgcgca    5160
agcaacggac ctttgacaac ggctctattc cccatcaaat tcacttgggt gagctgcatg    5220
ctatttttga gaagacaagaa gacttttatc catttttaaaa agacaatcgt gagaagattg    5280
aaaaaatctt gacttttcga attccttatt atgttggtcc attggcgcgt ggcaatagtc    5340
gttttgcatg gatgactcgg aagtctgaag aaacaattac cccatggaat ttgaagaag    5400 ttgtcgataa aggtgcttca gctcaatcat ttattgaacg catgacaaac tttgataaaa    5460
atcttccaaa tgaaaagta ctaccaaaac atagttgct ttatgagtat tttacggttt    5520
ataacgaatt gacaaaggtc aaatatgtta ctgaaggaat gcgaaaacca gcatttctt    5580 caggtgaaca agaaagcc attgttgatt tactcttcaa acaaatcga aaagtaaccg    5640 ttaagcaatt aaaagaagat tatttcaaaa aatagaatg ttttgatagt gttgaaattt    5700
caggagttga agatagattt aatgcttcat taggtaccta ccatgattg ctaaaaatta    5760
```

```
ttaaagataa agattttttg gataatgaag aaaatgaaga tatcttagag gatattgttt    5820
taacattgac cttatttgaa gatagggaga tgattgagga aagacttaaa acatatgctc    5880
acctctttga tgataaggtg atgaaacagc ttaaacgtcg ccgttatact ggttggggac    5940
gtttgtctcg aaaattgatt aatggtatta gggataagca atctggcaaa acaatattag    6000
attttttgaa atcagatggt tttgccaatc gcaattttat gcagctgatc catgatgata    6060
gtttgacatt taaagaagac attcaaaaag cacaagtgtc tggacaaggc gatagtttac    6120
atgaacatat tgcaaattta gctggtagcc ctgctattaa aaaggtatt ttacagactg     6180
taaaagttgt tgatgaattg gtcaaagtaa tggggcggca taagccagaa aatatcgtta    6240
ttgaaatggc acgtgaaaat cagacaactc aaaagggcca gaaaaattcg cgagagcgta    6300
tgaaacgaat cgaagaaggt atcaaagaat taggaagtca gattcttaaa gagcatcctg    6360
ttgaaaatac tcaattgcaa aatgaaaagc tctatctcta ttatctccaa aatggaagag    6420
acatgtatgt ggaccaagaa ttagatatta atcgtttaag tgattatgat gtcgatcaca    6480
ttgttccaca aagtttcctt aaagacgatt caatagacaa taaggtctta acgcgttctg    6540
ataaaaatcg tggtaaatcg gataacgttc caagtgaaga agtagtcaaa agatgaaaa    6600
actattggag acaacttcta aacgccaagt taatcactca acgtaagttt gataatttaa    6660
cgaaagctga acgtggaggt ttgagtgaac ttgataaagc tggttttatc aaacgccaat    6720
tggttgaaac tcgccaaatc actaagcatg tggcacaaat tttggatagt cgcatgaata    6780
ctaaatacga tgaaaatgat aaacttattc gagaggttaa agtgattacc ttaaaatcta    6840
aattagtttc tgacttccga aaagatttcc aattctataa agtacgtgag attaacaatt    6900
accatcatgc ccatgatgcg tatctaaatg ccgtcgttgg aactgctttg attaagaaat    6960
atccaaaact tgaatcggag tttgtctatg gtgattataa agtttatgat gttcgtaaaa    7020
tgattgctaa gtctgagcaa gaaataggca aagcaaccgc aaaatatttc ttttactcta    7080
atatcatgaa cttcttcaaa acagaaatta cacttgcaaa tggagagatt cgcaaacgcc    7140
ctctaatcga aactaatggg gaaactggag aaattgtctg ggataaaggg cgagattttg    7200
ccacagtgcg caaagtattg tccatgcccc aagtcaatat tgtcaagaaa acagaagtac    7260
agacaggcgg attctccaag gagtcaattt taccaaaaag aaattcggac aagcttattg    7320
ctcgtaaaaa agactgggat ccaaaaaaat atggtggttt tgatagtcca acggtagctt    7380
attcagtcct agtggttgct aaggtggaaa aagggaaatc gaagaagtta aaatccgtta    7440
aagagttact agggatcaca attatggaaa gaagttcctt tgaaaaaaat ccgattgact    7500
ttttagaagc taaaggatat aaggaagtta aaaagacttt aatcattaaa ctacctaaat    7560
atagtctttt tgagttagaa aacggtcgta acggatgct ggctagtgcc ggagaattac      7620
aaaaaggaaa tgagctggct ctgccaagca aatatgtgaa tttttatat ttagctagtc      7680
attatgaaaa gttgaagggt agtccagaag ataacgaaca aaaacaattg tttgtgggagc    7740
agcataagca ttatttagat gagattattg agcaaatcag tgaattttct aagcgtgtta    7800
ttttagcaga tgccaattta gataaagttc ttagtgcata taacaaacat agagacaaac    7860
caatacgtga acaagcagaa aatattattc atttatttac gttgacgaat cttggagctc    7920
ccgctgcttt taaatatttt gatacaacaa ttgatcgtaa acgatatacg tctacaaaag    7980
aagttttaga tgccactctt atccatcaat ccatcactgg tctttatgaa acacgcattg    8040
atttgagtca gctaggaggt gactaactcg agtaaggatc tccaggcatt gcaggcatgc    8100
```

```
ctcgagatgc atggcgccta acctaaactg atgacgcatc ctcacgataa tatccgggta    8160
ggcgcaatca ctttcgtcta ctccgttaca aagcgaggct gggtatttcc cggcctttct    8220
gttatccgaa atccactgaa agcacagcgg ctggctgagg agataaataa taaacgaggg    8280
gctgtatgca caaagcatct tctgttgagt taagaacgag tatcgagatg gcacatagcc    8340
ttgctcaaat tggaatcagg tttgtgccaa taccagtaga aacagacgaa gaatccatgg    8400
gtatggacag atctcaaaaa aagcaccgac tcggtgccac ttttcaagt tgataacgga     8460
ctagccttat tttaacttgc tatttctagc tctaaaacgg ttttcccag tcacgacgtg      8520
ctagcattat acctaggact gagctagctg tcagccattc gatggtgtca acgtaaatgc    8580
atgccgcttc gcctcgtccg gcgtagagga tctgctcatg tttgacagct tatcatcgat    8640
gcataatgtg cctgtcaaat ggacgaagca gggattctgc aaaccctatg ctactccgtc    8700
aagccgtcaa ttgtctgatt cgttaccaat tatgacaact tgacggctac atcattcact    8760
ttttcttcac aaccggcacg gaactcgctc gggctggccc cggtgcattt tttaaatacc    8820
cgcgagaaat agagttgatc gtcaaaacca acattgcgac cgacggtggc gataggcatc    8880
cgggtggtgc tcaaaagcag cttcgcctgg ctgatacgtt ggtcctcgcg ccagcttaag    8940
acgctaatcc ctaactgctg gcggaaaaga tgtgacagac gcgacggcga caagcaaaca    9000
tgctgtgcga cgctggcgat atcaaaattg ctgtctgcca ggtgatcgct gatgtactga    9060
caagcctcgc gtacccgatt atccatcggt ggatggagcg actcgttaat cgcttccatg    9120
cgccgcagta acaattgctc aagcagattt atcgccagca gctccgaata gcgcccttcc    9180
ccttgccccgg cgttaatgat tgcccaaac aggtcgctga aatgcggctg gtgcgcttca    9240
tccgggcgaa agaaccccgt attggcaaat attgacggcc agttaagcca ttcatgccag    9300
taggcgcgcg gacgaaagta aacccactgg tgataccatt cgcgagcctc cggatgacga    9360
ccgtagtgat gaatctctcc tggcgggaac agcaaaatat cacccggtcg gcaaacaaat    9420
tctcgtccct gatttttcac cacccccctga ccgcgaatgg tgagattgag aatataacct    9480
ttcattccca gcggtcggtc gataaaaaaa tcgagataac cgttggcctc aatcggcgtt    9540
aaacccgcca ccagatgggc attaaacgag tatcccggca gcagggggatc attttgcgct    9600
tcagccatac ttttcatact cccgccattc agagaagaaa ccaattgtcc atattgcatc    9660
agacattgcc gtcactgcgt cttttactgg ctcttctcgc taaccaaacc ggtaaccccg    9720
cttattaaaa gcattctgta acaaagcggg accaaagcca tgacaaaaac gcgtaacaaa    9780
agtgtctata atcacggcag aaaagtccac attgattatt tgcacggcgt cacactttgc    9840
tatgccatag catttttatc cataagatta gcggatccta cctgacgctt tttatcgcaa    9900
ctctctactg tttctccata cccgtttttt tgggctagcg aattcnnnnn nnnnnnnnnn    9960
nnnnnnnnnn nnnnnatgg ctaaaccagc aaaacgtatc aagagtgccg cagcggctta    10020
tgtgccacaa aaccgcgatg cggtgattac cgatattaaa cgcatcgggg atttacagcg    10080
cgaagcatca cgtctggaaa cggaaatgaa tgatgccatc gcggaaatta cggagaaatt    10140
tgcggcccgg attgcaccga ttaaaaccga tattgaaacc cttttcaaaag gcgttcaggg    10200
atggtgtgaa gcgaaccgcg acgaactgac gaacggcggc aaagtgaaga cggcgaatct    10260
tgtcaccggt gatgtatcgt ggcgggtccg tccaccatca gtaagtattc gtggtatgga    10320
tgcagtgatg gaaacgctgg agcgtcttgg cctgcaacgc tttattcgca cgaagcagga    10380
aatcaacaag gaagcgattt tactggaacc gaaagcggtc gcaggcgttg ccggaattac    10440
agttaaatca ggcattgagg atttttctat tattccattt gaacaggaag ccggtatttta    10500
```

```
attggctgtt ttggcggatg agagaagatt ttcagcggaa acacagaaaa aagcccgcac    10560
ctgacagtgc gggctttttt tttcgaccaa aggtccatgg gtatggacag ttttcccttt    10620
gatatgtaac ggtgaacagt tgttctactt ttgtttgtta gtcttgatgc ttcactgata    10680
gatacaagag ccataagaac c                                              10701
```

<210> SEQ ID NO 72
<211> LENGTH: 10593
<212> TYPE: DNA
<213> ORGANISM: Artificial
<220> FEATURE:
<223> OTHER INFORMATION: pCas9-LambdaGam
<220> FEATURE:
<221> NAME/KEY: misc_feature
<222> LOCATION: (9946)..(9976)
<223> OTHER INFORMATION: n is a, c, g, or t

<400> SEQUENCE: 72

```
tcagatcctt ccgtatttag ccagtatgtt ctctagtgtg gttcgttgtt tttgcgtgag      60
ccatgagaac gaaccattga gatcatactt actttgcatg tcactcaaaa attttgcctc     120
aaaactggtg agctgaattt ttgcagttaa agcatcgtgt agtgttttc ttagtccgtt      180 acgtaggtag gaatctgatg taatggttgt tggtattttg tcaccattca tttttatctg     240
gttgttctca agttcggtta cgagatccat tgtctatct agttcaactt ggaaaatcaa      300
cgtatcagtc gggcggcctc gcttatcaac caccaatttc atattgctgt aagtgtttaa     360
atctttactt attggtttca aacccattg gttaagcctt ttaaactcat ggtagttatt      420
ttcaagcatt aacatgaact taaattcatc aaggctaatc tctatatttg ccttgtgagt     480
tttcttttgt gttagttctt ttaataacca ctcataaatc ctcatagagt atttgttttc     540
aaaagactta acatgttcca gattatattt tatgaatttt tttaactgga aaagataagg     600
caatatctct tcactaaaaa ctaattctaa tttttcgctt gagaacttgg catagtttgt     660
ccactggaaa atctcaaagc ctttaaccaa aggattcctg atttccacag ttctcgtcat     720
cagctctctg gttgctttag ctaatacacc ataagcattt tccctactga tgttcatcat     780
ctgagcgtat tggttataag tgaacgatac cgtccgttct ttccttgtag ggttttcaat     840
cgtggggttg agtagtgcca cacagcataa aattagcttg gtttcatgct ccgttaagtc     900
atagcgacta atcgctagtt catttgcttt gaaacaact aattcagaca tacatctcaa      960
ttggtctagg tgattttaat cactatacca attgagatgg gctagtcaat gataattact    1020
agtccttttc ctttgagttg tgggtatctg taaattctgc tagaccttg ctggaaaact     1080 tgtaaattct gctagaccct ctgtaaattc cgctagacct ttgtgtgttt ttttgttta     1140 tattcaagtg gttataattt atagaataaa gaaagaataa aaaaagataa aagaataga    1200 tcccagccct gtgtataact cactacttta gtcagttccg cagtattaca aaggatgtc    1260 gcaaacgctg tttgctcctc tacaaaacag accttaaaac cctaaaggct taagtagcac    1320
cctcgcaagc tcggttgcgg ccgcaatcgg gcaaatcgct gaatattcct tttgtctccg    1380
accatcaggc acctgagtcg ctgtcttttt cgtgacattc agttcgctgc gctcacggct    1440
ctggcagtga atgggggtaa atggcactac aggcgccttt tatggattca tgcaaggaaa    1500
ctacccataa tacaagaaaa gcccgtcacg ggcttctcag ggcgttttat ggcgggtctg    1560
ctatgtggtg ctatctgact ttttgctgtt cagcagttcc tgccctctga ttttccagtc    1620
tgaccacttc ggattatccc gtgacaggtc attcagactg gctaatgcac ccagtaaggc    1680
```

-continued

```
agcggtatca tcaacggggt ctgacgctca gtggaacgaa aactcacgtt aagggatttt       1740
ggtcatgaga ttatcaaaaa ggatcttcac ctagatcctt ttaaattaaa aatgaagttt       1800
taaatcaatc taaagtatat atgagtaaac ttggtctgac agttacgttt ccacaaccaa       1860
ttaaccaatt ctgatttaga aaaactcatc gagcatcaaa tgaaactgca atttattcat       1920
atcaggatta tcaataccat attttgaaa aagccgtttc tgtaatgaag gagaaaactc        1980
accgaggcag ttccatagga tggcaagatc ctggtatcgg tctgcgattc cgactcgtcc       2040
aacatcaata caacctatta atttcccctc gtcaaaaata aggttatcaa gtgagaaatc       2100
accatgagtg acgactgaat ccggtgagaa tggcaaaagc ttatgcattt ctttccagac       2160
ttgttcaaca ggccagccat tacgctcgtc atcaaaatca ctcgcatcaa ccaaaccgtt       2220
attcattcgt gattgcgcct gagcgagacg aaatacgcga tcgctgttaa aaggacaatt       2280
acaaacagga atcgaatgca accggcgcag gaacactgcc agcgcatcaa caatatttc        2340 acctgaatca ggatattctt ctaatacctg gaatgctgtt ttcccgggga tcgcagtggt       2400
gagtaaccat gcatcatcag gagtacggat aaaatgcttg atggtcggaa gaggcataaa      2460
ttccgtcagc cagtttagtc tgaccatctc atctgtaaca tcattggcaa cgctaccttt       2520
gccatgtttc agaaacaact ctggcgcatc gggcttccca tacaatcgat agattgtcgc       2580
acctgattgc ccgacattat cgcgagccca tttatcccca tataaatcag catccatgtt      2640
ggaatttaat cgcggcctcg agcaagacgt ttcccgttga atatggctca taacacccct       2700
tgtattactg tttatgtaag cagacagttt tattgttcat gatgatatat ttttatcttg       2760
tgcaatgtaa catcagagat tttgagacac aacgtggctt tccctgcagg atttcggagg       2820
cctgcgttat cccctgattc tgtggataac cgtattaccg cctttgagtg agctgatacc      2880
gctcgccgca gccgaacgcc ccaaaaagcc tcgctttcag cacctgtcgt ttcctttctt       2940
ttcagagggt attttaaata aaaacattaa gttatgacga agaagaacgg aaacgcctta       3000
aaccggaaaa ttttcataaa tagcgaaaac ccgcgaggtc gccgcccgt aacctgtcgg        3060 atcaccggaa aggacccgta aagtgataat gattatcatc tacatatcac aacgtgcgtg      3120
gagggactag tggattttac ggctagctca gtcctaggta caatgctagc gaattcatta      3180
aagaggagaa aggtacccat ggcacgtacc ccgagccgta gcagcattgg tagcctgcgt      3240
agtccgcata cccataaagc aattctgacc agcaccattg aaatcctgaa gaatgtggt      3300 tatagcggtc tgagcattga aagcgttgca cgtcgtgccg gtgcaagcaa accgaccatt      3360
tatcgttggt ggaccaataa agcagcactg attgccgaag tgtatgaaaa tgaaagcgaa      3420
caggtgcgta aatttccgga tctgggtagc tttaaagccg atctggattt tctgctgcgt      3480
aatctgtgga agtttggcg tgaaaccatt tgtggtgaag catttcgttg tgttattgca       3540
gaagcacagc tggaccctgc aaccctgacc cagctgaaag atcagtttat ggaacgtcgt      3600
cgtgagatgc cgaaaaaact ggttgaaaat gccattagca atggtgaact gccgaaagat      3660
accaatcgtg aactgctgct ggatatgatt tttggttttt gttggtatcg cctgctgacc      3720
gaacagctga ccgttgaaca ggatattgaa gaatttaccc tcctgctgat taatggtgtt      3780
tgtccgggta cacagcgtta actagggccc ataccccccaa ttattgaagg ccgctaacgc      3840 ggccttttt tgtttctggt ctgcccgacg tacggtgaat ctgattcgtt accaattgac       3900
atgatacgaa acgtaccgta tcgttaaggt tactagagat taaagaggag aaatactaga      3960
tggataagaa atactcaata ggcttagata tcggcacaaa tagcgtcgga tgggcggtga      4020
tcactgatga atataaggtt ccgtctaaaa agttcaaggt tctgggaaat acagaccgcc      4080
```

```
acagtatcaa aaaaaatctt atagggctc ttttatttga cagtggagag acagcggaag   4140
cgactcgtct caaacggaca gctcgtagaa ggtatacacg tcggaagaat cgtatttgtt   4200
atctacagga gattttttca aatgagatgg cgaaagtaga tgatagtttc tttcatcgac   4260
ttgaagagtc ttttttggtg gaagaagaca agaagcatga acgtcatcct attttttggaa  4320 atatagtaga tgaagttgct tatcatgaga aatatccaac tatctatcat ctgcgaaaaa   4380
aattggtaga ttctactgat aaagcggatt tgcgcttaat ctatttggcc ttagcgcata   4440
tgattaagtt tcgtggtcat tttttgattg agggagattt aaatcctgat aatagtgatg   4500
tggacaaact atttatccag ttggtacaaa cctacaatca attatttgaa gaaaacccta   4560
ttaacgcaag tggagtagat gctaaagcga ttctttctgc acgattgagt aaatcaagac   4620
gattagaaaa tctcattgct cagctccccg gtgagaagaa aaatggctta tttgggaatc   4680
tcattgcttt gtcattgggt ttgacccta attttaaatc aaattttgat ttggcagaag    4740
atgctaaatt acagctttca aaagatactt acgatgatga tttagataat ttattggcgc   4800
aaattggaga tcaatatgct gatttgtttt tggcagctaa gaatttatca gatgctatt    4860 tactttcaga tatcctaaga gtaaatactg aaataactaa ggctcccta tcagcttcaa    4920 tgattaaacg ctacgatgaa catcatcaag acttgactct tttaaaagct ttagttcgac   4980
aacaacttcc agaaaagtat aaagaaatct tttttgatca atcaaaaaac ggatatgcag   5040
gttatattga tgggggagct agccaagaag aattttataa atttatcaaa ccaattttag   5100
aaaaaatgga tggtactgag gaattattgg tgaaactaaa tcgtgaagat ttgctgcgca   5160
agcaacggac ctttgacaac ggctctattc cccatcaaat tcacttgggt gagctgcatg   5220
ctattttgag aagacaagaa gactttttatc cattttttaaa agacaatcgt gagaagattg   5280
aaaaaatctt gacttttcga attccttatt atgttggtcc attggcgcgt ggcaatagtc   5340
gttttgcatg gatgactcgg aagtctgaag aaacaattac cccatggaat tttgaagaag   5400
ttgtcgataa aggtgcttca gctcaatcat ttattgaacg catgacaaac tttgataaaa   5460
atcttccaaa tgaaaagta ctaccaaaac atagtttgct ttatgagtat tttacggttt    5520
ataacgaatt gacaaaggtc aaatatgtta ctgaaggaat gcgaaaacca gcatttcttt   5580
caggtgaaca gaagaaagcc attgttgatt tactcttcaa aacaaatcga aaagtaaccg   5640
ttaagcaatt aaaagaagat tatttcaaaa aaatagaatg ttttgatagt gttgaaattt   5700
caggagttga agatagattt aatgcttcat taggtaccta ccatgatttg ctaaaaatta   5760
ttaaagataa agattttttg gataatgaag aaaatgaaga tatcttagag gatattgttt   5820
taacattgac cttatttgaa gatagggaga tgattgagga aagacttaaa acatatgctc   5880
acctctttga tgataaggtg atgaaacagc ttaaacgtcg ccgttatact ggttggggac   5940
gtttgtctcg aaaattgatt aatggtatta gggataagca atctggcaaa acaatattag   6000 atttttttgaa atcagatggt tttgccaatc gcaatttttat gcagctgatc catgatgata   6060
gtttgacatt taaagaagac attcaaaaag cacaagtgtc tggacaaggc gatagtttac   6120
atgaacatat tgcaaattta gctggtagcc ctgctattaa aaaaggtatt ttacagactg   6180
taaaagttgt tgatgaattg gtcaaagtaa tggggcggca aagccagaa aatatcgtta    6240 ttgaaatggc acgtgaaaat cagacaactc aaaagggcca gaaaaattcg cgagagcgta   6300
tgaaacgaat cgaagaaggt atcaaagaat taggaagtca gattcttaaa gagcatcctg   6360
ttgaaaatac tcaattgcaa aatgaaaagc tctatctcta ttatctccaa aatggaagag   6420
```

```
acatgtatgt ggaccaagaa ttagatatta atcgtttaag tgattatgat gtcgatcaca    6480
ttgttccaca aagtttcctt aaagacgatt caatagacaa taaggtctta acgcgttctg    6540
ataaaaatcg tggtaaatcg gataacgttc caagtgaaga agtagtcaaa aagatgaaaa    6600
actattggag acaacttcta aacgccaagt taatcactca acgtaagttt gataatttaa    6660
cgaaagctga acgtggaggt ttgagtgaac ttgataaagc tggttttatc aaacgccaat    6720
tggttgaaac tcgccaaatc actaagcatg tggcacaaat tttggatagt cgcatgaata    6780
ctaaatacga tgaaaatgat aaacttattc gagaggttaa agtgattacc ttaaaatcta    6840
aattagtttc tgacttccga aaagatttcc aattctataa agtacgtgag attaacaatt    6900
accatcatgc ccatgatgcg tatctaaatg ccgtcgttgg aactgctttg attaagaaat    6960
atccaaaact gaatcggag tttgtctatg gtgattataa agtttatgat gttcgtaaaa    7020
tgattgctaa gtctgagcaa gaaataggca aagcaaccgc aaaatatttc ttttactcta    7080
atatcatgaa cttcttcaaa acagaaatta cacttgcaaa tggagagatt cgcaaacgcc    7140
ctctaatcga aactaatggg gaaactggag aaattgtctg ggataaaggg cgagattttg    7200
ccacagtgcg caaagtattg tccatgcccc aagtcaatat tgtcaagaaa acagaagtac    7260
agacaggcgg attctccaag gagtcaattt taccaaaaag aaattcggac aagcttattg    7320
ctcgtaaaaa agactgggat ccaaaaaaat atggtggttt tgatagtcca acggtagctt    7380
attcagtcct agtggttgct aaggtggaaa agggaaatc gaagaagtta aaatccgtta    7440
aagagttact agggatcaca attatggaaa gaagttcctt tgaaaaaaat ccgattgact    7500
ttttagaagc taaaggatat aaggaagtta aaaagactt aatcattaaa ctacctaaat    7560
atagtctttt tgagttagaa acggtcgta acggatgct ggctagtgcc ggagaattac    7620
aaaaaggaaa tgagctggct ctgccaagca aatatgtgaa tttttatat ttagctagtc    7680 attatgaaaa gttgaagggt agtccagaag ataacgaaca aaaacaattg tttgtggagc    7740
agcataagca ttatttagat gagattattg agcaaatcag tgaattttct aagcgtgtta    7800
ttttagcaga tgccaattta gataaagttc ttagtgcata taacaaacat agagacaaac    7860
caatacgtga acaagcagaa aatattattc atttatttac gttgacgaat cttggagctc    7920
ccgctgcttt taaatatttt gatacaacaa ttgatcgtaa acgatatacg tctacaaaag    7980 aagtttttaga tgccactctt atccatcaat ccatcactgg tctttatgaa acacgcattg    8040
atttgagtca gctaggaggt gactaactcg agtaaggatc tccaggcatt gcaggcatgc    8100
ctcgagatgc atggcgccta acctaaactg atgacgcatc ctcacgataa tatccgggta    8160
ggcgcaatca ctttcgtcta ctccgttaca aagcgaggct gggtatttcc cggcctttct    8220
gttatccgaa atccactgaa agcacagcgg ctggctgagg agataaataa taaacgaggg    8280
gctgtatgca caaagcatct tctgttgagt taagaacgag tatcgagatg gcacatagcc    8340
ttgctcaaat tggaatcagg tttgtgccaa taccagtaga aacagacgaa gaatccatgg    8400
gtatggacag atctcaaaaa aagcaccgac tcggtgccac ttttttcaagt tgataacgga    8460 ctagccttat tttaacttgc tatttctagc tctaaaacgg ttttcccag tcgacgtg    8520 ctagcattat acctaggact gagctagctg tcagccattc gatggtgtca acgtaaatgc    8580
atgccgcttc gcctcgtccg gcgtagagga tctgctcatg tttgacagct tatcatcgat    8640
gcataatgtg cctgtcaaat ggacgaagca gggattctgc aaaccctatg ctactccgtc    8700
aagccgtcaa ttgtctgatt cgttaccaat tatgacaact tgacggctac atcattcact    8760 tttctcttcac aaccggcacg gaactcgctc gggctggccc cggtgcattt tttaaatacc    8820
```

-continued

```
cgcgagaaat agagttgatc gtcaaaacca acattgcgac cgacggtggc gataggcatc    8880
cgggtggtgc tcaaaagcag cttcgcctgg ctgatacgtt ggtcctcgcg ccagcttaag    8940
acgctaatcc ctaactgctg gcggaaaaga tgtgacagac gcgacggcga caagcaaaca    9000
tgctgtgcga cgctggcgat atcaaaattg ctgtctgcca ggtgatcgct gatgtactga    9060
caagcctcgc gtacccgatt atccatcggt ggatggagcg actcgttaat cgcttccatg    9120
cgccgcagta acaattgctc aagcagattt atcgccagca gctccgaata gcgcccttcc    9180
ccttgcccgg cgttaatgat ttgcccaaac aggtcgctga aatgcggctg gtgcgcttca    9240
tccgggcgaa agaacccgt attggcaaat attgacggcc agttaagcca ttcatgccag     9300
taggcgcgcg gacgaaagta aacccactgg tgataccatt cgcgagcctc cggatgacga    9360
ccgtagtgat gaatctctcc tggcgggaac agcaaaatat cacccggtcg gcaaacaaat    9420
tctcgtccct gattttcac cacccctga ccgcgaatgg tgagattgag aatataacct      9480
ttcattccca gcggtcggtc gataaaaaaa tcgagataac cgttggcctc aatcggcgtt    9540
aaacccgcca ccagatgggc attaaacgag tatcccggca gcagggatc attttgcgct     9600
tcagccatac tttttcatact cccgccattc agagaagaaa ccaattgtcc atattgcatc   9660
agacattgcc gtcactgcgt cttttactgg ctcttctcgc taaccaaacc ggtaaccccg    9720
cttattaaaa gcattctgta acaaagcggg accaaagcca tgacaaaaac gcgtaacaaa    9780
agtgtctata atcacggcag aaaagtccac attgattatt tgcacggcgt cacactttgc   9840
tatgccatag catttttatc cataagatta gcggatccta cctgacgctt tttatcgcaa    9900
ctctctactg tttctccata cccgttttt tgggctagcg aattcnnnnn nnnnnnnnn      9960
nnnnnnnnnn nnnnnnatgg atattaatac tgaaactgag atcaagcaaa agcattcact   10020
aacccccttt cctgttttcc taatcagccc ggcatttcgc gggcgatatt ttcacagcta   10080
tttcaggagt tcagccatga acgcttatta cattcaggat cgtcttgagg ctcagagctg   10140
ggcgcgtcac taccagcagc tcgcccgtga agagaaagag gcagaactgg cagacgacat   10200
ggaaaaaggc ctgccccagc acctgtttga atcgctatgc atcgatcatt tgcaacgcca   10260
cggggccagc aaaaaatcca ttacccgtgc gtttgatgac gatgttgagt ttcaggagcg   10320
catggcagaa cacatccggt acatggttga aaccattgct caccaccagg ttgatattga   10380
ttcagaggta taattggctg tttttggcgga tgagagaaga ttttcagcgg aaacacagaa   10440
aaaagcccgc acctgacagt gcgggctttt tttttcgacc aaaggtccat gggtatggac   10500
agttttccct ttgatatgta acggtgaaca gttgttctac ttttgtttgt tagtcttgat   10560
gcttcactga tagatacaag agccataaga acc                                10593
```

SEQUENCE-SPECIFIC ANTIMICROBIALS BY BLOCKING DNA REPAIR

SEQUENCE LISTING

The instant application contains a Sequence Listing which has been submitted electronically in ASCII format and is hereby incorporated by reference in its entirety. Said ASCII copy, created on Nov. 1, 2019, is named 15744039.txt and is 126,074 bytes in size.

FIELD OF THE INVENTION

The invention relates to endonuclease-based antimicrobials that generate double-strand break(s) (DSB(s)) in prokaryotic cells. In this respect, the invention especially concerns a method involving blocking DNA repair after a nucleic acid has been submitted to DSB. The invention also relates to a vector encoding such endonuclease and a protein blocking DNA repair, a pharmaceutical composition and a product comprising said vector for use in the treatment of diseases dues to a bacterium infection

BACKGROUND OF THE INVENTION

Cas proteins such as Cas9, of CRISPR-Cas systems, are members of the programmable nucleases, that have emerged as popular tools to introduce mutations in eukaryotic genomes as also are Zinc Finger Nucleases (ZFN) or Transcription Activator-Like Effector Nucleases (TALEN). Double strand breaks introduced in genomes by these nucleases can be repaired either through Homology Directed Repair (HDR) or through Non-Homologous End Joining (NHEJ). Most bacterial species lack a Non-Homologous End Joining (NHEJ) system. When a double strand beak is introduced at a given position in all copies of the chromosome simultaneously, the bacterium will die without DNA repair. When a double strand beak is introduced at a given position in all copies of an antibiotic resistance plasmid simultaneously, the bacterium will be susceptible to the antibiotic without DNA repair.

In bacteria, double strand breaks are generally repaired through homologous recombination with an intact sister chromosome. The first step of repair involves loading of the RecBCD or AddAB complex on the double strand ends. The ends are then resected through a helicase and exonuclease activity until a specific sequence motif known as the chi site is found. In *E. coli* the sequence of the chi site is GCTGGTGG. Once a chi site is found, the RecBCD/AddAB complex keeps degrading one of the strands white the other strand is loaded with the recA protein. The nucleoprotein filament can then invade the sister chromosome and initiate replication dependent repair. RecBCD/AddAB resects double stranded ends present in the cell at the very high speed of ~1 kb/sec. If no homologous sequence is present in the cell the DNA molecule is completely destroyed. Upon infection, phages thus need to protect their double strand ends from RecBCD/AddAB. For these purpose they have evolved different strategies to either block the access of the double strand end (e.g. the Mu Gam protein) d'Adda di Fagagna et al., EMBO reports, 4(1):47-52 (2003), or directly block the activity of RecBCD/AddAB through direct binding (e.g. the lambda Gam protein). Murphy et al., J. Bacteriology 173 (18): 5808-5821 (1991).

It was shown in the prior art that nuclease cleavage can kill the cells when all chromosomal copies are cut simultaneously and no intact template is available for homology directed repair. However, not all targets are equal and some positions are being targeted more efficiently than others. Inefficient nuclease interference can be tolerated through continuous repair by the homologous recombination pathway. Accordingly, in several bacteria a DNA repair occurs after nuclease cleavage. Thereof, the use of the nucleases only is not sufficient to kill bacteria.

Consequently, there is a need to novel method allowing efficiently killing of bacteria and thus being used in antimicrobial treatments.

SUMMARY OF THE INVENTION

Surprisingly, the inventors of the present invention found that combining the action of an endonuclease with the action of some proteins involved in bacteriophage DNA protection enhance the ability of endonuclease to kill bacteria cells since these proteins do not allow DNA repair.

According to a first aspect, the invention thus relates to a method for killing a bacterium comprising contacting the bacterium with an endonuclease, preferably encoded by at least one recombinant phagemid(s) or plasmid(s), that creates a double-stranded break in the chromosomal DNA of the bacterium and an exogenous molecule that inhibits double-stranded break repair, preferably a protein that binds to the ends of the double-stranded break.

Using the method of the present application, it is possible to select specific DNA sites for the cleavage. Such site may be the part of the DNA sequences responsible for the antibiotic resistance of bacterium.

According to another aspect, the method of the invention is used for making a bacterium more susceptible to an antibiotic, said method comprising contacting the bacterium with an endonuclease, preferably encoded by at least recombinant phagemid(s) or plasmid(s), and the antibiotic, wherein the endonuclease creates a double-stranded break in an antibiotic resistance gene encoded by the bacterium, and an exogenous molecule that inhibits double-stranded break repair, preferably a protein that binds to the ends of the double-stranded break. In one embodiment, the recombinant phagemid or plasmid encodes a Cas9 nuclease, a guide RNA, and an exogenous Gam protein.

In order to implement the method of the invention, it is necessary to provide a vector, particularly a phagemid vector encoding a nuclease susceptible to cleave DNA double strand of bacterium and a protein that binds to the ends of the double-stranded break and inhibit DSB repair.

According to one aspect, the invention thus relates to a phagemid vector encoding a nuclease, and optionally, an exogenous protein that binds to the ends of the double-stranded break and inhibit DSB repair.

In various embodiments, the invention relates to a phagemid vector encoding a nuclease, preferably Cas9 nuclease, a guide RNA, and an exogenous protein that binds to the ends of the double-stranded break and inhibit DSB repair, particularly Gam protein. In another embodiment, the guide RNA targets an antibiotic resistance plasmid or a plasmid carrying virulence genes. In various embodiments, the guide RNA targets the bacterial chromosome. In various embodiments, the phagemid vector is a P1 bacteriophage. In various embodiments, the phagemid vector is a λ bacteriophage.

According to another aspect, the invention also relates to a host cell comprising the phagemid or plasmid vector of the invention and a phagemid or plasmid vector encoding the protein inhibiting DSB repair.

According to a further aspect, the invention also relates to a pharmaceutical composition comprising the phagemid or plasmid vector of the invention and a vector encoding the protein inhibiting DSB repair or the protein inhibiting DSB repair and a pharmaceutical acceptable vehicle for use in the treatment of diseases due to a bacterium infection.

The present application also relates to a product comprising
- at least one phagemid or plasmid vector or pharmaceutical composition of the invention, and
- at least another therapeutic agent, in particular an antibiotic as a combination product for simultaneous, separate or sequential use for the treatment of at least one disease due to a bacterium infection, particularly infection due to at least one of bacteria selected from the group comprising of *Enterobacter*, Streptococci, Staphylococci, Enterococci, *Salmonella, Pseudomonas, Mycobacterium*.

BRIEF DESCRIPTION OF THE DRAWINGS

FIGS. 1A to 1D. Weak self-targeting CRISPR-Cas9 systems can be tolerated through homology directed repair. (A) Position of the targets on the *E. coli* chromosome. Targets on the inside of the circle are on the non-template strand, targets on the outside are on the template strand. (B) The pCRRNA carrying different spacers was transformed in cells expressing Cas9 constitutively. Average CFU numbers are reported for transformation in wild-type cells (black bars) and recA− cells (white bars), showing that some spacers can be tolerated in the presence of recA but not in the recA− strain (mean±s.d., n≥3). Transformation events yielding small colonies are marked with a star. (C) Schematics of the transformation assay performed to demonstrate homology directed repair. The pCas9 (also designated pCas9-a carrying a control spacer that can be easily replaced through restriction-ligation cloning) plasmid SEQ ID NO: 60 (indicated as SEQ ID No. 117 in the priority application) carrying Cas9, the tracrRNA and a CRISPR array was programmed to target a position within the lacZ gene. The resulting plasmid pCas9::lacZ2 (carrying a spacer targeting the lacZ gene) having the sequence of SEQ ID No. 119 was transformed in cells carrying a plasmid with homologies to the target region but carrying a mutation preventing Cas9 cleavage (pLCX SEQ ID NO: 66). (D) CFU numbers are reported after transformation either in wild-type (black bars) or recA− cells (white bars), showing that the presence of a repair template rescues killing induced by Cas9 cleavage of the lacZ2 target (mean±s.d., n≥3).

FIGS. 3A to 3C: Cas9 cleavage in the chromosome induces the SOS response. (A) The pCRRNA plasmid programmed to target the lacZ1 position (black bars) or a control empty pCRRNA (white bars) were introduced in cells expressing Cas9 under the leaky control of a non-induced ptet promoter in the chromosome. SOS induction is reported by a GFPmut2 gene under the control of the sulA promoter (pZA31-sulA-GFP). GFP fluorescence was measured during exponential growth (mean±s.d., n≥3). (B) SOS response induced by targeting with different spacers. The bar marked as "control" indicates the auto-fluorescence level of *E. coli* without the pZA31-sulA-GFP plasmid. Spacers that cannot be transformed under constitutive Cas9 expression from the pCas9 (see FIG. 1B) are shown in white. Spacers that can be transformed but lead to the formation of small colonies (see FIG. 1B) are shown in grey. Finally, spacers that can be transformed in the presence of pCas9 and form colonies of regular size (see FIG. 1B) are shown in black (mean±s.d., n≥3). (C) analysis of Cas 9 induced deletions in recB-strain: the deletions observed after transformation of the stain are indicated.

DETAILED DESCRIPTION OF THE INVENTION

Figure 2:
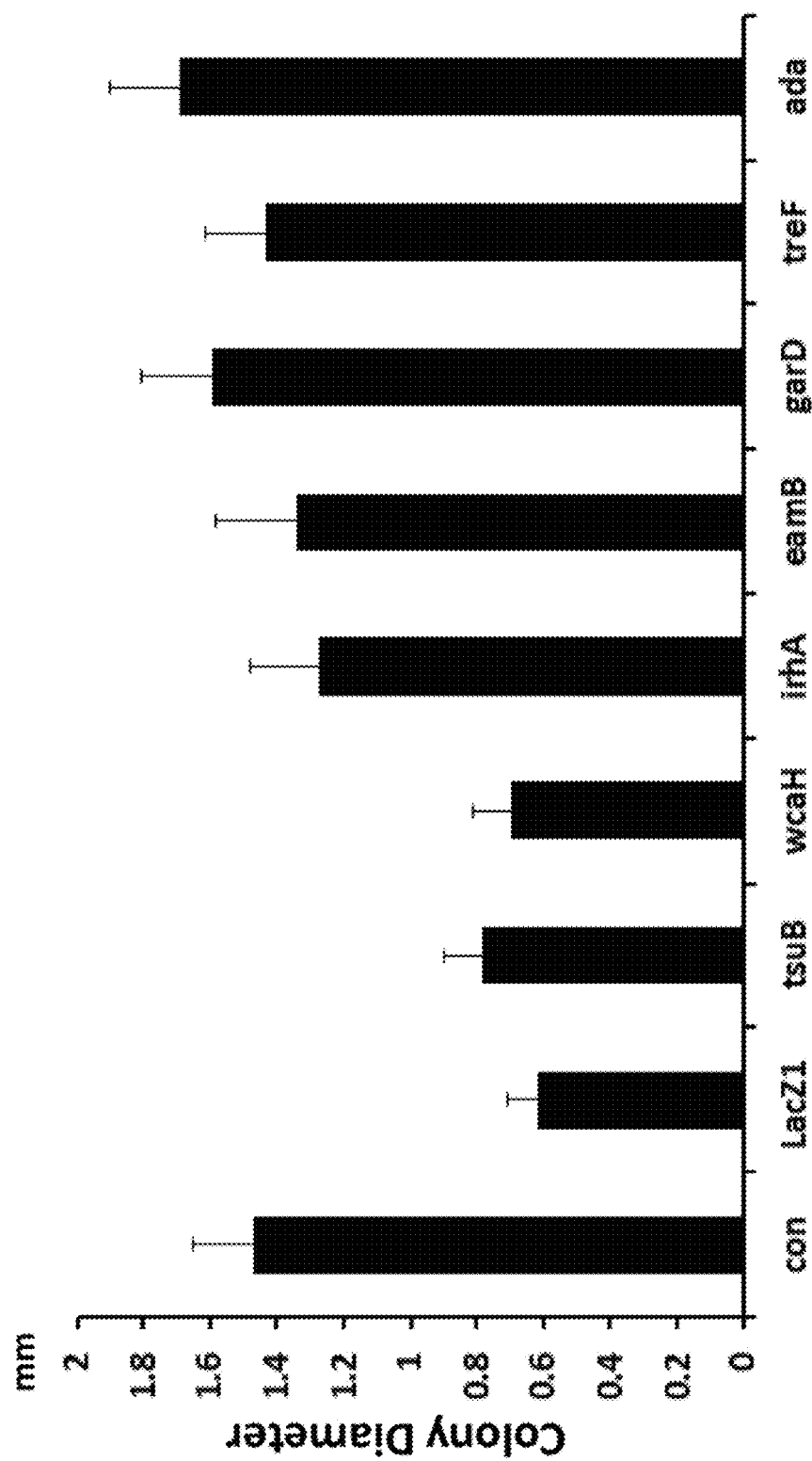
FIG. 2: Colony size after transformation with self-targeting CRISPR systems. The pCRRNA plasmid carrying different spacers was transformed in MG1655 cells expressing Cas9 constitutively from plasmid pCas9. Cells were plated on selective medium and colony diameter was quantified after 16H of incubation at 37° C. using the ImageJ software. A minimum of 50 colonies were counted for each individual transformation.

In the aim to avoid bacterium DNA sequence repair after nuclease cleavage, the inventor found that specific proteins that bind the end of cleaved site may be used. The inventors thus implemented a method for killing bacterium comprising contacting the bacterium with an endonuclease, preferably encoded by a recombinant phagemid(s) or plasmid(s), wherein the recombinant phagemid(s) or plasmid(s) encodes an endonuclease that creates a double-stranded break in the chromosomal DNA of the bacterium, and an exogenous molecule that inhibits DNA repair.

In a preferred embodiment, the molecule is an exogenous protein that binds to the ends of the double-stranded break and inhibits DSB repair.

In another embodiment, the exogenous protein does not bind to the ends of the double strand break but affects other repairing mechanism, preferably recBCD.

In a particular embodiment, the method encompasses generating a double-strand break (DSB) in the chromosomal DNA of the cell using a chemical reagent such as nuclease, in particular a meganuclease selected from a Homing endonuceases (HEs) or an artificial endonuclease selected from the group comprising or consisting of a Zinc Finger Nuclease, TALEN and a CRISPR-Cas system, or using a physical reagent such as irradiation, or expressing said chemical reagent in the cell as a result of expression of a polynucleotide encoding the same when said cell has been genetically transformed with said polynucleotide.

In one embodiment, the endonuclease specifically cleaves the chromosomal or extrachromosomal DNA of the bacterium at less than 2, 3, 4, 5, 6, 7, 8, 9, or 10 different sites. Most preferably, the endonuclease specifically cleaves the chromosomal or extrachromosomal DNA of the bacterium at a single site.

In another embodiment of the invention, the protein which binds cleaved ends of DNA and block in such way DNA repair is selected from the group comprising or consisting of Mu phage Gam protein, a lambda phage Gam protein, or a phage T7 gp5.9 protein. Preferably, the protein is a recBCD or AddAB inhibitor. Other inhibitors of recBCD or AddAB are known in the art [43] In various embodiments, the bacterium comprises a recBCD homologous repair pathway or an AddAB system. In various embodiments, the bacterium does not comprise a recBCD homologous repair pathway or an AddAB system.

In the present invention a programmable nucleases and in particular the CRISPR-Cas9 system can be used as a sequence specific antimicrobial when delivered in bacterial populations [15] This system relies on the ability of the RNA-guided Cas9 nuclease to kill bacteria when introducing a double strand break in the chromosome. However, some bacterial DNA repair pathways can compete with Cas9 cleavage allowing cells to survive. The recBCD homologous repair pathway can indeed repair breaks introduced when Cas9 is guided by weak guide RNAs that do not lead to the simultaneous cleavage of all copies of the target sequence, leaving an intact copy of the target sequence available as a repair template at any given time.

The term "CRISPR" or "Clustered regularly interspaced short palindromic repeats" as used in the present invention relates to segments of prokaryotic DNA containing short repetitions of base sequences. Each repetition is followed by short segments of "spacer DNA" from previous exposures to a bacteriophage virus or plasmid.

The term "CRISPR/Cas9 system" as used in the present invention relates to a prokaryotic immune system that confers resistance to foreign genetic elements such as those present within plasmids and phages and provides a form of acquired immunity. CRISPR spacers recognize and cut these exogenous genetic elements in a manner analogous to RNA interference in eukaryotic organisms. By delivering the Cas9 nuclease and appropriate guide RNAs into a cell, the cell's genome can be cut at a desired location, allowing existing genes to be removed and/or new ones added [07].

According to preferred embodiment of the invention, a DNA end binding protein known as Gam is used to prevent the action of the DNA repair machinery upon Cas9 cleavage. Gam is a protein from bacteriophage Mu that is orthologue to the Ku protein of NHEJ systems [44]. It is however not involved in repair but protects the Mu phage DNA in its linear form from host exonucleases [45]. Gam binds double strand ends (DSE) and protects them from recBCD exonuclease activity. It was shown that upon UV exposure, the survival of cells expressing Gam is similar to that of a recB mutant, indicating that Gam blocks DNA repair [46]. The inventors shown here that Gam expression can be combined with Cas9 targeting to efficiently kill bacteria even when using weak guide RNAs that would otherwise be tolerated by the cell.

The fact that not all targets are able to kill *E. coli* means that it might be difficult to use Cas9 as a reliable tool for genome editing or as a sequence-specific antimicrobial. In order to make Cas9 killing more reliable, the inventors investigated methods to prevent DNA repair which can restore Cas9's or other endonucleases' ability to kill a bacterium (e.g., *E. coli*) even when directed by a weak crRNA. The Gam protein of phage Mu binds double stranded ends and protects the phage DNA from degradation by host exonucleases. The inventors cloned the Mu gam gene under the control of a pBAD promoter and measured the transformation efficiency of pCas9 programmed either with a spacer that they previously described as weak (lacZ1) or with a stronger spacer (lacZ2). Surprisingly, transformation of pCas9::lacZ1 in the presence of arabinose led to ~250× fewer colonies than in the absence of arabinose, while the expression of Gam had no effect on CFU numbers of a non-targeting control pCas9 plasmid. Also surprisingly, the efficiency of killing of the lacZ2 spacer, which is already good, was further improved ~14× in the presence of Gam. Together, these results demonstrate the usefulness of using an inhibitor of double strand break repair pathways in combination with Cas9 or other endonucleases to ensure that it will kill the targeted cells.

As used herein the term "plasmid" relates to a small DNA molecule within a cell that is physically separated from a chromosomal DNA and can replicate independently. The plasmids are most commonly found in bacteria as small circular, double-stranded DNA molecules; however, plasmids are sometimes present in archaea and eukaryotic organisms. The artificial plasmids are widely used as vectors in molecular cloning, serving to drive the replication of recombinant DNA sequences within host organisms.

As used herein the term "phagmid" refers to a plasmid that can be packaged into a phage capsid. This includes f1/M13 filamentous phages but also other type of phages. A phagemid is thus defined as a DNA circuit that can be packaged into a phage capsid and delivered to target bacteria. Typically a phagemid is obtained from a temperate phage by cloning the packaging signal of the phage on a plasmid. The production of phagemid particles, i.e. the plasmid DNA packaged into the phage protein capsids, is achieved by using a production strain carrying the lysogenic helper phage and the phagemid. Upon induction of the phage lytic cycle, phage capsids are produced that will package the phagemid DNA. The packaging signal can be removed from the helper phage in order to obtain pure phagemid particles.

According to one embodiment of the method of the present invention a phagemid(s) or bacterial conjugation can be used to deliver the endonuclease and the inhibitor of DSB repair, particularly a protein that binds to the ends of the double-stranded break and inhibits DSB repair. Suitable phagemids can be based on the following phages, including M13, lambda, p22, T7, Mu, T4 phage, PBSX, P1Puna-like, P2, I3, Bcep 1, Bcep 43, Bcep 78, T5 phage, phi, C2, L5, HK97, N15, T3 phage, P37, MS2, Qß, or Phi X 174. Preferred phages are selected from λ phage, T2 phage, T4 phage, T7 phage, T12 phage, R17 phage, M13 phage, MS2 phage, G4 phage, P1 phage, Enterobacteria phage P2, P4 phage, Phi X 174 phage, N4 phage, *Pseudomonas* phage φ6, φ29 phage, and 186 phage. Other suitable phages can be found in the Felix d'Herelle collection (phage.ulaval.ca/en/accueil).

According to one embodiment of the invention, one phagimid or plasmid encodes the endonuclease and another phagemid or plasmid encodes the protein inhibiting DSB repair.

According to another embodiment, the protein inhibiting DSB repair is synthetized prior to contacting it with bacterium.

In a specific embodiment of the method, the prokaryotic cell, in particular a bacterial cell, is transformed with DNA polynucleotide(s) encoding the polypeptide(s) and RNA transcripts of a bacterial CRISPR-Cas system comprising (i) a nucleic acid molecule encoding a programmable double-stranded DNA Cas endonuclease and (ii) DNA molecule(s) comprising a combination of sequences encoding a guide RNA (gRNA) encompassing the crRNA and tracrRNA transcripts, wherein the DNA molecule(s) is (are) either a two-molecule DNA encoding crDNA and tracrRNA independently or a chimeric DNA encoding a single crRNA-tracrRNA transcript (said chimeric DNA being designated as sgRNA for single guide RNA), wherein the nucleic acid molecule and DNA molecule(s) are under the control of regulatory elements for transcription including promoter(s).

The crRNA (CRISPR RNA) is encoded by a DNA molecule comprising a CRISPR array that comprises one or multiple distinct DNA sequence(s) (designated spacer(s)) suitable for screening or for recognition of and base pairing hydridization to one or respectively multiple distinct target nucleotide sequence(s) in a genomic nucleic acid in said prokaryotic cell said spacer sequence(s) being framed by a repeat sequence, said DNA being transcribed as a primary transcript which gives rise to short crRNA by processing.

crRNA is obtained as a result of the processing of the primary transcript of the CRISPR array, said processing involving binding of the tracrRNA transcript to the repeat region of the CRISPR primary transcript and recognition of the tracrRNA::CRISPR RNA duplex by Cas, especially Cas 9 and cleavage by the host RNAseIII.

According to the invention, the DNA polynucleotide(s) encoding the polypeptide(s) and RNA transcripts of the CRISPR-Cas system are borne by a vector, in particular a recombinant plasmid(s) or phagemid(s).

In the DNA polynucleotide(s) encoding the guide RNA, the DNA molecule encoding the tracrRNA can be combined or fused, on a single plasmid or phagemid, with the sequence encoding the crRNA comprising the CRISPR array. In the CRISPR array a leader sequence may be present adjacent to the spacer sequences framed by the repeat sequences.

In the plasmid(s) or phagemid(s), the coding sequences are under the control of a promoter for transcription, in particular a constitutive promoter or an inducible promoter.

According to the invention, the DNA polynucleotide(s) encoding the polypeptide(s) and RNA transcripts of the CRISPR-Cas system comprise(s) (i) a nucleic acid molecule encoding a programmable double-stranded DNA Cas endocuclease and (ii) DNA molecule(s) comprising a combination of or alternatively a fusion of a sequence encoding a guide RNA (gRNA) which comprises the crRNA and the tracrRNA transcripts, wherein the DNA molecule encoding the crRNA encompasses (a) a CRISPR array and (b) a sequence complementary to part of a sequence of the tracrRNA coding sequence.

In a particular embodiment, the CRISPR system is from a *Streptococcus*, particularly a *Streptococcus pyogenes*.

In one embodiment, the bacterium is a *Mycobacterium*, in particular *Mycobacterium tuberculosis*, or a *Pseudomonas*, in particular *Pseudomonas aeruginosa*. In various embodiments, the bacterium is selected from the group comprising or consisting of an *E. coli*, a *Bacillus subtilis*, a *Pseudomonas Aeruginosa*, a Mycobacteria, a *Streptococcus pyogenes*, or a *Staphylococcus aureus*. In various embodiments, the bacterium is selected from the group comprising or consisting of an Enterococci, *Clostridium difficile*, Enterobacteriaceae, *Neisseria gonorrhoeae, Acinetobacter, Campylobacter, Salmonella, Shigella*, or *Streptococcus pneumonia.*

In preferred embodiment, bacteria are selected from the group comprising *Enterobacter*, Streptococci, Staphylococci, Enterococci, particularly *E. coli, Salmonella, Pseudomonas Aeruginosa, Mycobacterium tuberculosis, Streptococcus pyogenes, Staphylococcus aureus* and *Enterococcus faecali*.

Particularly, bacteria are antibiotic resistant bacteria.

The invention further relates to the use of the method of the invention for making a bacterium more susceptible to an antibiotic comprising contacting the bacterium with an endonuclease, preferably encoded by a recombinant phagemid(s) or plasmid(s), wherein the endonuclease creates a double-stranded break in an antibiotic resistance gene encoded by the bacterium, the antibiotic, and an exogenous molecule that inhibits DNA repair. In a preferred embodiment, the molecule is an exogenous protein that binds to the ends of the double-stranded break and inhibits DSB repair that binds to the ends of the double-stranded break and inhibits DSB repair. Preferably, the protein is Mu phage Gam protein, a lambda phage Gam protein, or a phage T7 gp5.9 protein. Preferably, the protein is a recBCD or AddAB inhibitor. Other inhibitors of recBCD are for example genes abc1 and abc2 from phage P22 [43].

Introduction of a DSB in the chromosome (and in the presence of Gam) will kill the bacterium, no matter where the target is. If the target is in an antibiotic resistance gene, the bacterium will die and will thus not be resensitized to the antibiotic. On the other hand, if the target is carried by a plasmid, no matter where the target is on the plasmid sequence, then the plasmid will be destroyed. If the plasmid carries an antibiotic resistance gene, then the bacterium will be made more susceptible to the antibiotic.

Preferably, the double-strand break(s) is (are) performed in a chromosomal context, i.e. on a double strand DNA when it is present on the chromosomal DNA of the cell, either naturally or as a result of insertion of a DNA sequence in said cell chromosome(s).

The prokaryotic cell, in particular the bacterial cell used to carry out the methods of the invention can be an isolated cell or a culture of cells.

The invention also relates to a method for making a bacterium more susceptible to an antibiotic comprising contacting the bacterium with an endonuclease, preferably encoded by a recombinant phagemid(s) or plasmid(s), wherein the endonuclease creates a double-stranded break in an antibiotic resistance gene encoded by the bacterium, the antibiotic, and an exogenous molecule that inhibits DNA repair. This method have the same characteristics as the method of the invention for making a bacterium more susceptible to an antibiotic described above.

The invention encompasses phagemid vectors and plasmids encoding endonucleases and/or proteins that inhibit DSB repair. Preferably, the phagemid or plasmid vector(s) encodes the endnuclease and the protein that binds to the ends of the double-stranded break and inhibits DSB repair.

According to one embodiment of the invention, the plasmid or phagimig vector encodes only the endonuclease and the protein inhibiting DSB repair is encoded by another plasmid or phagimid.

In one embodiment the endonuclease encoded by phagemid and/or plasmid vectors is selected from a meganuclease, preferably a Homing endonuclease (HEs) or an artificial endonuclease, preferably selected from the group comprising a Zinc Finger Nuclease, TALEN and Cas nuclease of CRISPR-Cas system, more preferably, a Cas9 nuclease, a guide RNA, and the exogenous protein is selected from the group comprising Mu phage Gam protein, a lambda phage Gam protein, a phage T7 gp5.9 protein, preferably a Mu phage Gam protein and a lambda phage Gam protein.

According to one preferred embodiment of the invention, the phagemid(s) or plasmid(s) encode a nuclease, a guide RNA, and an exogenous protein.

According to another preferred embodiment the guide RNA encompasses a two molecule DNA encoding a CRISPR system's crRNA and tracrRNA independently or a chimeric DNA (sgRNA) encoding a single crRNA-tracrRNA transcript.

Most preferably, the phagemid(s) or plamid(s) encode a Cas9 nuclease, a guide RNA, and an exogenous Gam protein. In various embodiments, the guide RNA targets an antibiotic resistance plasmid or a plasmid carrying virulence genes. In various embodiments, the guide RNA targets the bacterial chromosome. In various embodiments, the phagemid vector is a P1 bacteriophage. In various embodiments, the phagemid vector is a λ bacteriophage.

The invention accordingly relates in particular to a plasmid or phagemid vector encoding a CRISPR-Cas system, in particular wherein the CRISPR-Cas system is a type II CRISPR associated (Cas) system comprising DNA polynucleotide(s) encoding the polypeptide(s) and RNA transcripts of a bacterial CRISPR-Cas system encompassing (i) a polynucleotide comprising a sequence encoding a Cas double-stranded DNA endonuclease, in particular Cas 9, (ii) DNA molecule(s) comprising a combination of sequences encoding a guide RNA (gRNA) encompassing the crRNA and tracrRNA transcripts, wherein the DNA molecule(s) is (are) either a two-molecule DNA encoding crRNA and tracrRNA independently or a chimeric DNA encoding a single crRNA-tracrRNA transcript (said chimeric DNA being designated as sgRNA for single guide RNA), wherein the nucleic acid molecule and DNA molecule(s) are under the control of regulatory elements for transcription including promoter(s) wherein in the gRNA a succession of DNA targeting nucleotide sequences (designated spacers) having 20 to 40 nucleotides, in particular 30 nucleotides or any value in the ranges defined by the thus disclosed values is present and wherein each spacer's transcript is intended to screen or is able to target a specific DNA sequence of interest to form a RNA-DNA interaction with the target sequence and wherein each spacer is framed by identical DNA repeat sequences. Said CRISPR associated Cas system is provided in the cell as a single operon or as multiple polynucleotides.

The so-called spacer sequence may be designed to target a specific nucleotide sequence in the chromosomal DNA of the cell, i.e. to target a determined polynucleotide strand. In a particular embodiment, the spacer sequence may be designed to possibly hybridize with a known sequence of nucleotides of a chromosome in a determined polynucleotide of interest. Alternatively it may be designed randomly, i.e., with no predetermined target in the chromosomal sequence of the cell and accordingly the polynucleotide of interest may be a sequence randomly targeted or screened in said chromosomal DNA. The spacer(s) sequence may thus be the natural sequence of the CRISPR system or may be a sequence heterologous to said natural CRISPR system, selected for its ability to target a proper determined or undetermined sequence in the chromosomal DNA of the prokaryotic cell. Accordingly, the CRISPR system is designed for programmed targeting in the chromosomal DNA of the prokaryotic cell whether the sequence of the targeted polynucleotide comprising the target is known or not said sequence being of prokaryotic origin or brought to the prokaryotic cell from a eukaryotic DNA by recombination of the prokaryotic cell.

The targeted polynucleotide may be of any type and is further disclosed hereafter.

The "repeat sequence" that frames the spacer sequences in the CRISPR system is involved in the maturation of the preCRISPR RNA transcript and in the mature transcript designated crRNA. Accordingly, part of the repeat sequence is contained in the crRNA. The repeat sequence may encompass 20 to 50, in particular 20 to 40 or 35 to 40 nucleotides or any range that may be defined having recourse to these disclosed values, or any value in-between and especially 36 nucleotides as illustrated in the example of *S. pyrogenes.*

For Illustration, particular repeat sequences are SEQ ID Nos 1 to 10 below (these sequences correspond to the SEQ ID Nos: 99 to 108 of the priority application):

```
                                              SEQ ID No. 1
(GTTTTTGTACTCTCAAGATTTAAGTAACTGTACAAC)

SEQ ID No. 2
(GATATAAACCTAATTACCTCGAGAGGGGACGGAAAC)

SEQ ID No. 3
(GTTTTGGAACCATTCGAAACAACACAGCTCTAAAAC)

SEQ ID No. 4
(GTTTTAGAGCTATGCTGTTTTGAATGGTCCCAAAAC)

SEQ ID No. 5
(ATTTCAATCCACTCACCCATGAAGGGTGAGAC)

SEQ ID No. 6
(GTTTCAGTAGCTAGATTATTTGATATACTGCTGTTAG)

SEQ ID No. 7
(AATCAGAGAATACCCCGTATAAAAGGGGACGAGAAC)

SEQ ID No. 8
(GTTCACTGCCGCACAGGCAGCTTAGAAA)

SEQ ID No. 9
(GGTTGTAGCTCCCTTTCTCATTTCGCAGTGCTACAAT)

SEQ ID No. 10
(CCGGATTCCCGCCTGCGCGGGAATGACG)
```

As mentioned above, alternatively to being composed of a DNA molecule encoding the Cas9 protein and DNA molecules encoding tracrRNA and crRNA transcripts provided as separate genes, the CRISPR-Cas system is a type II CRISPR associated (Cas) system encompassing (i) a polynucleotide comprising a sequence encoding a Cas double-stranded DNA endonuclease, in particular Cas 9, and (ii) a chimeric DNA that is transcribed as a chimeric RNA i.e., single guide RNA (sgRNA) encompassing a fusion of the nucleic acids transcribed as the tracrRNA and the crRNA on the same or on a different plasmid or phagemid as the one expressing Cas.

The CRISPR associated system may encompass a Cas double-stranded DNA endonuclease the gene of which flanks the polynucleotide encoding the gRNA or the sgRNA in a Cas operon. This CRISPR associated system may involve in particular the programmable endonuclease Cas 9 as described in detail in the Examples and illustrated for the performance of DSB in *E. coli.*

Alternatively, the gene of the CAS endonuclease may be provided on a separate DNA construct. The polynucleotide encoding the gRNA or the sgRNA (CRISPR genetic construct) and the polynucleotide encoding the endonuclease may thus be introduced into the cell by transformation with a single or multiple plasmids or phagemids.

The CRISPR array comprises one or multiple spacer sequences framed by a repeat sequence that are transcribed into pre-CRISPR RNA which is processed to small RNA sequences (crRNA) that allow DNA targeting in the chromosomal nucleic acid of the prokaryotic cell, the DNA target being complementary enough to the spacer transcript present in the crRNA to hybridize with it when the target DNA comprises, in addition, immediately downstream to the target region, a recognition sequence designated PAM sequence (Photospacer-adjacent Motif).

The spacer sequence(s) of the CRISPR array may advantageously consist of 20 to 40 nucleotides, in particular 30 nucleotides or any value in the ranges defined by the thus disclosed values and the sequence(s) are chosen by reference to the target in the chromosomal nucleic acid or as a random sequence when no specific sequence is targeted in the nucleic acid. The repeat sequence in the CRISPR system is one which may be processed by the enzymes of the prokaryotic cell thereby giving rise to the small crRNA encompassing a transcript of at least part of the repeat sequence. Illustration of spacer sequences is provided herein as SEQ ID No. 1 to 10 and in the Examples.

The polynucleotide transcribed into the tracrRNA is a short RNA antisense to the precursor RNA. The formed tracrRNA enables the loading of the crRNA on the Cas protein and accordingly participates in a RNA-protein complex that involves tracrRNA, crRNA and Cas protein (so-called dual-RNA:Cas) that targets the chromosomal nucleic acid to then allow the DSB to take place at the targeted loci. As mentioned above, the nucleic acids transcribed as the tracrRNA and the crRNA may be fused in a chimeric nucleic acid giving rise to a sgRNA when the CRISPR system is active in the cell.

In a particular embodiment, the CRISPR-Cas system is composed of associated nucleic acid molecules, one of them encoding the Cas 9 protein and the additional one(s) being transcribed as the tracrRNA, and as the crRNA, the nucleic acids being under the control of distinct or common regulatory sequences for expression, including a promoter. In a particular embodiment the tracrRNA and crRNA give rise to a chimeric transcript i.e., a sgRNA and are under the control of the same transcription promoter.

Optionally, the nucleic acid molecules are borne by different plasmids or phagemids and remain independent. The polynucleotide or nucleic acid molecules are under the control of suitable transcription or expression control elements.

In a particular embodiment, the CRISPR-associated Cas9 system is encoded by a nucleic acid from a *Streptococcus* genus in particular from a *Streptococcus pyrogenes* strain.

In a preferred embodiment, the CRISPR system comprises the sequence of the leader and the repeat sequence from the locus of *Streptococcus pyrogenes* disclosed as SF370 under accession number NC_002737.

In a particular embodiment the CRISPR-Cas system is provided by plasmid pCas9 (also named pCas9-a) having the sequence of SEQ ID NO: 60 (indicated as SEQ ID No. 117 in the priority application) or a derivative thereof, particularly a phagemid, wherein the region corresponding to the control spacer, from nucleotide position 6520 to position 6549, is substituted by one or multiple spacer(s) of choice or is provided by plasmid pCas9-LacZ2 having the sequence of SEQ ID NO: 61 (indicated as SEQ ID No. 119 in the priority application) or a derivative thereof, particularly a phagemid, wherein the region from nucleotide position 6520 to position 6549 (CRISPR target ELZ2) is substituted by one or multiple spacer(s) of choice.

Other bacterial species may provide the Cas 9 protein or nucleic acid molecule encoding the Cas 9 protein. These species include, for illustrative purposes only: *Francisella novicida, Legionella pneumophila, Streptococcus thermophulus, Streptococcus mutans, Coriobacterium glomerans, Staphylococcus lugdumensis, Enterococcus faecalis, Mycoplasma canis, Campylobacter jejuni, Neisseria meningitidis, Pasteurella multocida.*

According to another particular embodiment of the invention, the CRISPR system is provided by two plasmids or phagemids used for the transformation of the cell: a first plasmid or phagemid provides the polynucleotides encoding the Cas protein (said first plasmid or phagemid can be built on the same basis as the pCas9 provided it is not recombined with the sequence encoding the crRNA and the tracrRNA transcripts), a second plasmid or phagemid that encodes the crRNA and the tracrRNA transcripts said second plasmid or phagemid comprising in a particular embodiment a DNA polynucleotide that comprises the "gRNA scaffold for the CRISPR/Cas 9 system" having the sequence from nucleotide 1565 to nucleotide 1640 in the sequence of SEQ ID NO:62 (indicated as SEQ ID No. 123.in the priority application).

Said second plasmid or phagemid can be in particular derived from plasmid psgRNAc BsaI (SEQ ID No. 62).

According to a particular embodiment of the invention, in the second plasmid or phagemid, the DNA polynucleotide(s) comprise(s) in addition, the sequence of the tracrRNA ending at position 1647 in the sequence of SEQ ID No. 62.

According to a particular embodiment of the invention, said second recombinant plasmid or phagemid encoding the single guide RNA for the CRISPR/Cas 9 system comprises the sequence of SEQ ID No.62. In said phagemid, the sequence of the control spacer from nucleotide position 1545 to nucleotide position 1564 in the sequence of SEQ ID No. 62 may be substituted by any selected sequence of choice for a spacer and in particular a spacer sequence disclosed herein.

The protein that binds to the ends of the double-stranded break and inhibits DSB repair can be expressed from either the first or second recombinant plasmid or phagemid or on a third plasmid or phagemid.

In a particular embodiment the CRISPR-associated Cas9 system is expressed in the recombinant prokaryotic cell as a ternary complex that involves tracrRNA paired to crRNA and bound to Cas9 wherein the crRNA targets DNA on the chromosome of the recombinant prokaryotic cell to cause at least one DSB in the DNA.

In a particular embodiment, the CRISPR array comprises 1 to 10, in particular 1 to 5 spacer sequences. When multiple spacer sequences are thus contained in the CRISPR array, this array is transcribed as multiple crRNA molecules having distinct spacer sequence, thereby enabling multiplex DSB to take place at different loci of the chromosomal DNA of the prokaryotic cell.

In a particular embodiment of the invention, the method is used to introduce DSBs at any locus (loci) of interest in the chromosome simply by changing the sequence of the guide spacer.

According to the invention, a chromosomal sequence, in which a DSB is generated is defined as a "polynucleotide of interest". According to a particular embodiment, as stated above, a polynucleotide of interest can be a targeted polynucleotide despite it does not require that its nucleotide sequence upstream and downstream of the cut site for DSB is determined. Targeting in this respect may rely on criteria such as location into the chromosome, functional parameters of the target DNA, which are known or are to be identified, involvement in phenotypic traits, or structural parameters of the DNA. Targeting may take into consideration possible functional or structural relationship among multiple DNA. Alternatively, in another embodiment of the invention, the said polynucleotide of interest is a nucleic acid which is heterologous with respect to the natural chromosomal nucleic acid of the prokaryotic cells wherein the invention is carried out. The expression "heterologous" means that said nucleic acid is originating from a different cell, species or organism than the cell type which is used to perform the invention, or is a non-naturally occurring nucleic acid such as a chimeric or an artificial nucleic acid. Such heterologous polynucleotide may nevertheless have been inserted in the genome of the cell, possibly using recombinant technologies. In a particular embodiment the heterologous sequence may be a eukaryotic DNA sequence, especially a chromosomal eukaryotic sequence.

The polynucleotide of interest may comprise the cleavage site where the DSB is generated and the required PAM (photospacer adjacent motif) sequence the latter corresponding to a sequence either naturally present in the target DNA or introduced in it.

The PAM sequence is recognized by the Cas protein and is accordingly dependent of the choice of this protein. The PAM sequence functional with the Cas9 protein is a sequence 5'XGG3' on the complementary strand of the target polynucleotide, wherein X means any nucleotide.

Alternatively, the polynucleotide of interest may have been inserted into the chromosomal substrate through the action of an agent or of an organism, such as a bactreiophage.

The polynucleotide of interest can be in its native form, or it may have undergone modifications with respect to a reference wild-type form if any, especially when it is a polynucleotide which is inserted and integrated in the chromosomes of the cell. The modifications may be carried out prior to or after the insertion into the cell or as a result of recombination into the cell genome.

The polynucleotide of interest of the invention, either known in its composition or randomly selected (random polynucleotide), may be a nucleic acid of a gene or of a gene fragment, including an exon, an intron, an expression regulatory sequence such as a promoter, a coding sequence, a non-coding sequence. It may be a nucleic acid of prokaryotic or of eukaryotic origin. It may be a nucleic acid, especially of prokaryotic origin, originating from a pathogenic organism, such as a viral or bacterial or parasite nucleic acid, including a protein coding sequence. It may be a nucleic acid of prokaryotic origin, originating from a non-pathogenic organism.

The polynucleotide of interest of the invention may be present as a single sequence in the chromosomal substrate of the cell or rather may be present as multiple copies of its sequence, either contiguous in the chromosome or spread on the chromosome. In a particular embodiment, different polynucleotides, i.e., polynucleotides having different nucleotide sequences, present in the chromosomal substrate of the cell are subject to the double-strand break.

According to a first step of the method of the invention, a DSB is generated in a targeted way in the DNA sequence of the targeted polynucleotide, which means that a specific locus of the polynucleotide is the target of the break in the prokaryotic cell.

In another embodiment of the invention, the site for the DSB is not a single site, i.e., there can be multiple sites in the polynucleotide.

Double-strand break site for the purpose of the invention may be unique in the polynucleotide of interest (giving rise to a single DSB event) or may be multiple (giving rise to multiple DSB events) especially as a result of the presence of multiple distinct spacers in the CRISPR system. DSB sites are indeed determined by the sequence of the spacer(s) of the CRISPR system and the presence in the chromosomal DNA (possibly after modification) of PAM sequences.

As a result of the CRISPR construct used, it is possible to perform double-strand break, especially targeted DSB, in one or more than one locus of the chromosomal DNA of prokaryotic cells.

As examples of DNA targets of interest, the invention provides nucleic acids consisting in or contained in:
- a gene expressing an enzyme, such as a kinase, in particular wherein the sequence of the polynucleotide of interest encodes the active site of the enzyme,
- a gene expressing a cell receptor,
- a gene expressing a structural protein, a secreted protein,
- a gene expressing resistance to an antibiotic, or to a drug in general
- a gene expressing a toxic protein or a toxic factor,
- a gene expressing a virulence protein or a virulence factor,
- a polynucleotide, especially a gene of a pathogen such as a virus a bacterium or a parasite,
- regulatory sequences for transcription or for expression of said genes.

In one embodiment, the method of the invention may be used for increasing the nuclease activity, particularly when in suboptimal conditions (variating the in vitro used conditions) or when there is one or several mutations in target DNA, the nuclease activity is decreased. Thus, the method of the invention may be used for enhancing nuclease efficiency.

In one aspect the present invention also relates to a host cell comprising a vector encoding an endonuclease according to the invention and a vector encoding a protein inhibiting DSB repair.

In one embodiment, the host cell can contain a vector encoding an endonuclease and a protein inhibiting DSB repair.

Such host cell may be used for research purposes.

In another aspect, the invention also relates to a pharmaceutical composition comprising the vector as described above and a pharmaceutical acceptable vehicle for the treatment of diseases due to a bacterium infection.

In the context of the present invention "pharmaceutical acceptable vehicle" refers to a compound, or a combination of compounds, entering a pharmaceutical composition that does not cause secondary reactions and that, for example, facilitates administration of the active compounds, increases its lifespan and/or effectiveness in the organism, increases its solubility in solution or improves its storage. Such pharmaceutical carriers are well-known and will be adapted by a person skilled in the art according to the nature and the administration route of the active compounds selected.

The pharmaceutical composition according to the invention further comprises a vector encoding the protein inhibiting DSB repair or protein inhibiting DSB repair.

In one embodiment, the pharmaceutical composition is suitable for the treatment of diseases due to a bacterium selected from the group comprising *Enterobacter*, Streptococci, Staphylococci, Enterococci, *Salmonella, Pseudomonas, Mycobacterium*.

In another embodiment, the pharmaceutical composition further comprising an antibiotic, particularly a suitable antibiotic for treating infection due to a bacterium selected from the group of *Enterobacter*, Streptococci, Staphylococci, Enterococci, *Salmonella, Pseudomonas, Mycobacterium*.

According to a further aspect, the invention relates to a product comprising
- at least one phagemid or plasmid vector of the invention as described above or a pharmaceutical composition of the invention, and
- at least another therapeutic agent, in particular an antibiotic as a combination product for simultaneous, separate or sequential use for the treatment of at least one disease due to a bacterium infection, particularly an infection due to at least one bacterium selected from the group comprising *Enterobacter*, Streptococci, Staphylococci, Enterococci, *Salmonella, Pseudomonas, Mycobacterium*.

According to another aspect, the invention also relates to a method for treating diseases due to a bacterial infection, said method comprising administering at least one phagemid or plasmid vector or a pharmaceutical composition or a product according to the invention to a subject suffering from a bacterium infection.

According to one embodiment, the therapeutic method of the invention is used for treating a patient suffering from an infection with at least one bacterium selected in the group comprising *Enterobacter*, Streptococci, Staphylococci, Enterococci, *Salmonella, Pseudomonas, Mycobacterium*.

Further characteristics and embodiments will be apparent from the Examples which follow and from the figures.

EXAMPLES

Example 1 Effect of Double Strand Breaks Introduced by Cas9 on Cell Death and Conditions for Survival to Such DNA Damage Clustered Regularly Interspaced Short Palindromic Repeats (CRISPR) and CRISPR associated (Cas) genes are the adaptive immune system of bacteria and archaea [1]. The RNA-guided Cas9 nuclease from *Streptococcus pyogenes* has emerged as a useful and versatile tool [2]. The ease with which it can be reprogrammed has in particular been driving its adoption for genome editing applications. Cas9 is guided by a small CRISPR RNA (crRNA) that is processed from the initial transcript of the CRISPR locus by Cas9 together with a trans-activating CRISPR RNA (tracrRNA) and the host RNAseIII [3]. Both the tracrRNA and the processed crRNA remain bound to Cas9 and act as a complex to direct interference against target DNA molecules[4]. Alternatively, the crRNA and tracrRNA can be fused forming a chimeric single guide RNA (sgRNA) [4]. Cas9 scans DNA looking for a short sequence motif known as the Protospacer Adjacent Motif (PAM) [5]. Once a PAM is found, DNA is unwound to make base-pair contacts between the crRNA and the target DNA. If base-pairing occurs, a conformational shift in Cas9 brings two nuclease domains in contact with the target DNA leading to the creation of a double strand break (DSB) [6].

Genome editing using Cas9 has been reported in a large number of eukaryotes including insects, plants, mammals, yeast, zebrafish, xenopus and nematode [2]. However it has so far only been demonstrated in a few bacteria species and with a handful of target positions [7-9]. In eukaryotic cells DSB introduced by Cas9 can be repaired through Homology Directed Repair (HDR) with a template DNA molecule carrying a mutation of interest [10,11]. Alternatively, error-prone repair by Non-Homologous End Joining (NHEJ) can lead to small indels at the target site which are used to knockout genes [10,11]. In contrast, most bacteria lack a NHEJ system [12,13] and Cas9-induced breaks in bacterial genomes lead to cell death [14-16]. This repair pathway thus cannot be used to introduce small deletions and knockout genes. However, the ability to kill bacteria carrying a specific sequence in the chromosome can be used in conjunction with a mutagenesis strategy to select for cells that carry a desired mutation [7].

More recently, the ability of chromosome-targeting CRISPR systems to kill bacteria was used to develop sequence-specific antimicrobials [14,15]. In these studies phage capsids are used to deliver a CRISPR system programmed to target antibiotic resistance or virulence genes either in E. coli or S. aureus. In both cases this strategy was able to efficiently kill the targeted bacteria specifically.

First, the inventors investigated why DSB introduced by Cas9 leads to cell death and whether some cells can survive such DNA damage.

Example 2 Bacterial Strains and Media

E. coli strains were grown in Luria-Bertani (LB) broth (10 g Tryptone, 5 g Yeast Extract, 10 g NaCl, add ddH2O to 1000 ml, PH7.5, autoclaved). 1.5% LB Agar was used as solid medium. Different antibiotics (20 ug/ml chloramphenicol, 100 ug/ml carbenicillin, 50 ug/ml kanamycin) were used as needed. Plates containing IPTG (100 uM) and X-gal (40 ug/ml) were used for blue/white screening. Escherichia coli strain MG1656 (a Δlacl-lacZ derivative of MG1655) was used as a cloning strain for plasmid pCas9::lacZ2 (see below). E. coli strains N4278 (MG1655 recB268::Tn10)[29], MG1655 RecA::Tn10 and JJC443 (lexAind3 MalF::Tn10)[30] are gifts from the Mazel lab.

Example 3 Plasmid Cloning pCRRNA was assembled by amplification of pCRISPR using primer B299/LC34 and of the tracrRNA fragment from pCas9 using primers LC35/LC36, followed by Gibson assembly [31]. Novel spacers were cloned into pCRRNA or pCas9 plasmids as previously described [7]. The vector was digested with BsaI, followed by ligation of annealed oligonucleotides designed as follows: 5'-aaac+(target sequence)+g-3' and 5'-aaaac+(reverse complement of the target sequence)-3'. A list of all spacers tested in this study is provided in (Table 2 in the present application was indicated with the number 4 in the text of the priority application corresponding to the table 2 of the priority application).

The pLCX plasmid was assembled from the pCRISPR backbone amplified using primers LC41/LC42 and two lacZ fragments amplified from MG1655 genomic DNA using primers LC38/LC39 and LC37/LC40. The pZA31-sulA-GFP plasmid was assembled from pZA31-Luc [32] linearized with primers LC192/LC193, the sulA promoter fragment amplified with primers LC194/LC196 and GFPmut2 [33] amplified with primers LC191/LC195. All PCR primers are listed in (Table 3 in the present application was indicated with the number 5 in the text of the priority application corresponding to the table 3 of the priority application).

Example 4 CRISPR Transformation Assays

The pCRRNA or pCas9 plasmids (with different spacers) were transformed in recipient E. coli strains by chemical transformation using 100 ng of plasmid DNA. CFU numbers were normalized by pUC19 transformation efficiency. All transformations were repeated at least 3 times.

Example 5 SOS Response

The pZA31-sulA-GFP plasmid was used to monitor SOS induction [34]. The OSIP system [36] was used to integrate cas9 or dcas9 under the control of a ptet promoter [20] in the chromosome of strains MG1655, N4278 (MG1655 recB268::Tn10) [29], MG1655 RecA::Tn10 and JJC443 (lexAind3 MalF::Tn10) [30] (Table 1 in the present application was indicated with the number 3 in the text of the priority application corresponding to the table 1 of the priority application). pCRRNA plasmids with different spacers were transformed by chemical transformation. Colonies isolated from the transformation plate were re-suspended in 200 ul LB in a 96 well microtiter plate. The microtiter plate was loaded into a TECAN infinite M200 Pro machine. OD (600 nm) and GFP fluorescence (excitation filter set to 486 nm and emission filter set to 518 nm) were measured over a 10 hour time course. GFP values at OD of 0.4 are reported.

Example 6 Cloning of the pLC13 Plasmid

The pLC13 plasmid was constructed through Gibson assembly of plasmid pBAD18 [47, amplified with primers LC2/LC296 together with the gam gene of bacteriophage Mu amplified with primers LC397/LC398 from the genomic DNA of E. coli S17-1 LPIR[5]. The sequence of pLC13 (which is fully present in the text of the description of the priority application) corresponds to SEQ ID NO: 11 of the sequence listed annexed to the present specification.

Example 7 pCas9 Transformation and Plating Assay

The pCas9, pCas9:LacZ1 and pCas9:LacZ2 plasmids were transferred into MG1655 cells carrying the pLC13 plasmid. Cells were plated on LB-agar with or without 0.2% L-arabinose. Serial dilutions were performed to quantify CFU for each transformation.

TABLE 4

Primers used for pCas9 transfection.

| SEQ ID NO: | Primer Name | Primer sequences (5' to 3') |
| --- | --- | --- |
| 12 | LC2 | CCTTCTTAAAGTTACCGAGCTCGAATTCGC |
| 13 | LC296 | TATATTTTAGGAATTCTAAAGATCTTTGACAGCTAGCTCAGTCCTAGGTATAATACTAGT |
| 14 | LC397 | ATCCGCCAAAACAGCCAATTAAATACCGGCTTCCTGTTC |
| 15 | LC398 | GCGAATTCGAGCTCGGTAACTTTAAGAAGGAGATATACCATGGCTAAACCAGCAAAACGTA |

Example 8 E. coli can Survive Cas9 Cleavage Through Homology Directed Repair Evidence that CRISPR interference directed against the chromosome leads to cell death first came from the observation that an active CRISPR system and its target cannot coexist in the same cell [16-18]. Transformation of E. coli by a plasmid carrying a CRISPR system targeting the chromosome is very inefficient, typically resulting in 1,000-fold decrease in transformation efficiency compared to a non-targeting control [7, 17, 19]. In a previous study, we took advantage of this to introduce a mutation in the rpsL gene of E. coli [7]. Targeting of the rpsL gene by Cas9 killed the cells that did not incorporate a desired mutation provided by an oligonucleotide. To investigate whether this approach could be extended to other loci, we programmed a plasmid-born CRISPR array to target 12 positions spread throughout the E. coli chromosome and compared them with the rpsL target previously published. All targets were chosen in non-essential genes to ensure that killing by Cas9 would be the result of DNA cleavage and not repression of the target gene [20,21]. The pCRRNA plasmid carries the tracrRNA and a minimal CRISPR array consisting of the leader sequence and a single spacer framed by two repeats. This plasmid was transformed in cells containing the pCas9 plasmid expressing Cas9 constitutively [7]. Surprisingly, 8 out of 12 spacers could be readily transformed with efficiencies comparable to that of the non-targeting control (FIG. 1). Interestingly, three of them (lacZ1, tsuB and wcaH) resulted in colonies smaller than the control (FIG. 2). The inventors hypothesized that Cas9 cleavage in these cells might be inefficient and that competition with the bacteria repair system would stress the cells and slow down colony growth. To test this idea, the inventors repeated this transformation experiment in cells deleted for recA. Consistently with inventors' hypothesis, no colonies could be recovered after transformation of spacers lacZ1, tsuB and wcaH, but also after transformation of all the other spacers. This shows that all spacers are able to direct Cas9 cleavage in the chromosome, including those that can be transformed efficiently, and all spacers induce lethal DSB in the absence of recA. However, only some spacers are able to kill cells in the presence of recA. This indicates that weak spacers might be tolerated in wild-type cells thanks to the Homology Directed Repair (HDR) pathway.

Homologous recombination can only rescue a DSB if an intact sister chromosome is available. This suggests that for some spacers Cas9 cleavage is not efficient enough to cut all copies of the chromosome simultaneously. A corollary is that spacers that do lead to cell death probably kill the cells because no repair template is available. If this is true, then providing an intact repair template during targeting should be able to rescue the cells. To test this hypothesis the inventors constructed a plasmid, pLCX, carrying a 1 kb fragment homologous to the target region of spacer lacZ2, but with a point mutation in the PAM motif blocking CRISPR interference (FIG. 1C). Transformation of the lacZ2 spacer led to ~100× more colonies in the presence of pLCX than in cells carrying a control empty plasmid, and no colonies could be recovered in the recA mutant (FIG. 1D). The lacZ gene of the recovered colonies was sequenced and confirmed to carry the point mutation provided by the pLCX plasmid, showing that it was indeed used as a template for HDR.

Example 9 Cas9 Cleavage Leads to SOS Induction

Figure 4:
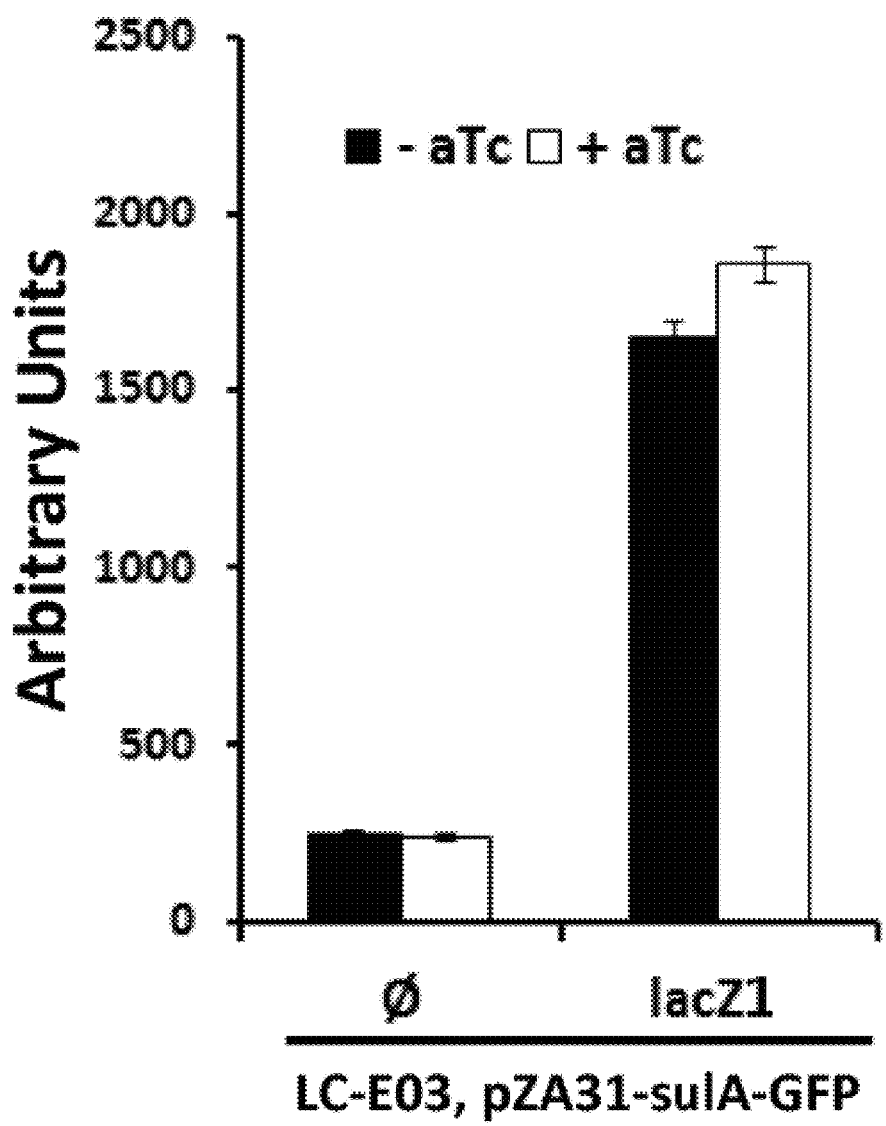
FIG. 4: SOS activation by Cas9 cleavage of the lacZ1 target with or without anhydrotetracyclin (aTc) induction. The pZA31-sulA-GFP plasmid was used to monitor SOS induction after pCRRNA::∅ or pCRRNA::lacZ1 transformation in LCE03 cells expressing cas9 under the control of a ptet promoter in the chromosome (see Table 1). Cells were grown to an OD of 0.4 and 1 uM aTc was added. GFP fluorescence was measured 2H after induction. The strong GFP signal measured in the absence of aTc indicates that the ptet promoter controlling Cas9 is leaky.
Figure 5:
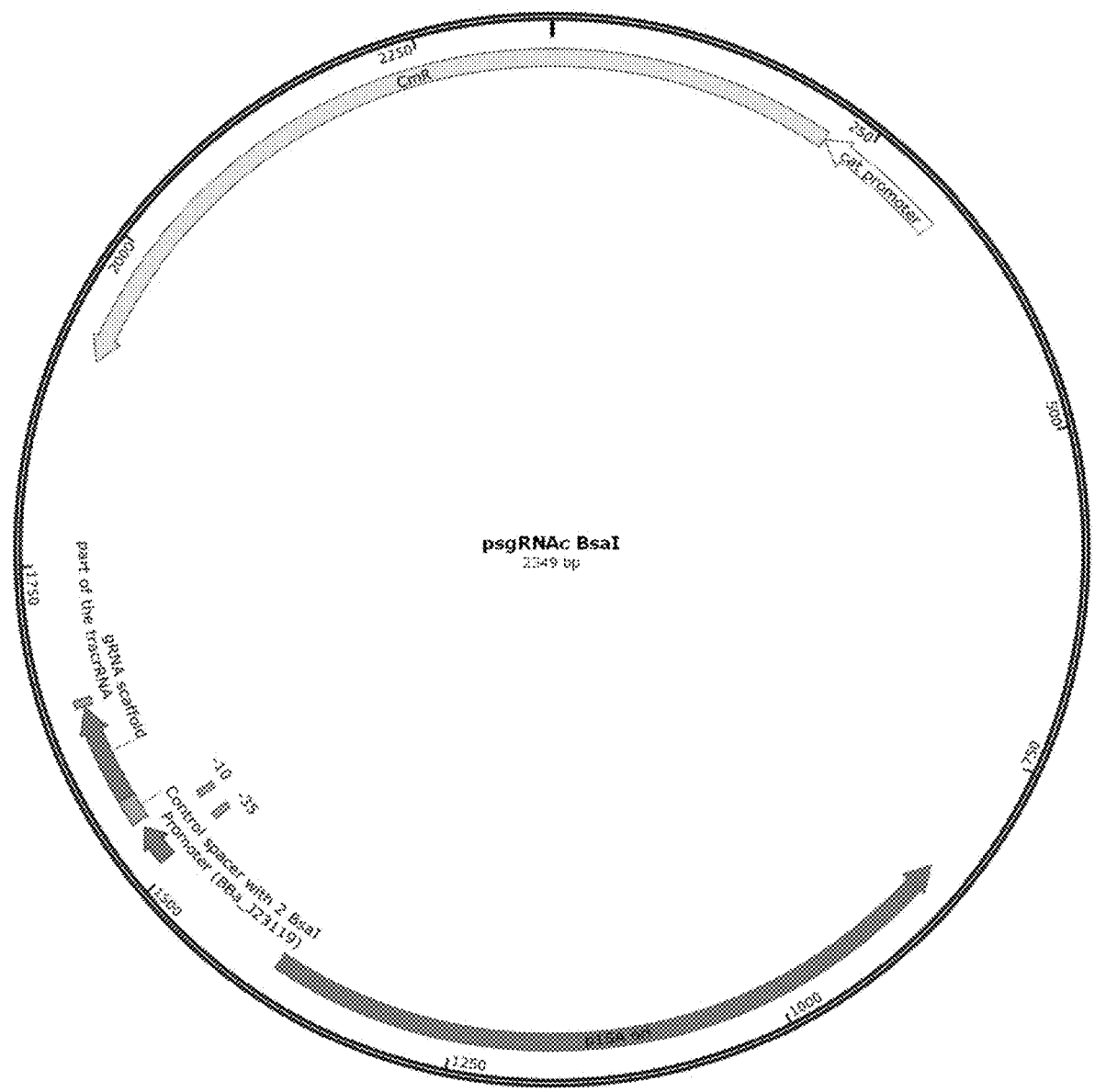
FIG. 5: Map of plasmid psgRNAc BsaI SEQ ID NO: 62 (indicated as SEQ ID No. 123 in the priority application)

Spacers that can be tolerated likely result in constant Cas9 cleavage and recA mediated repair. This should lead to an elevated level of SOS induction. To test this the inventors integrated cas9 in the chromosome under the control of a ptet promoter and monitored SOS levels with a GFP reporter plasmid. Spacers were provided on the pCRRNA. Targeting with the lacZ1 spacer led to elevated GFP fluorescence levels when aTc was added to the media, but more surprisingly also in the absence of induction (FIG. 3A and FIG. 4). This demonstrates that the ptet promoter controlling Cas9 is leaky and that the small amount of Cas9 proteins produced can already lead to the introduction of DSB resulting in SOS induction. Consistently with an induction of the SOS pathway, no fluorescence could be observed in recA, recB or lexA(ind-) mutants (FIG. 3A). Mutations in the catalytic sites of Cas9 also abolished SOS induction showing that cleavage of DNA and not mere binding is the cause of the SOS induction (FIG. 3A, dCas9). We further measured the SOS response triggered by all 13 spacers (FIG. 3B). Interestingly, the strength of SOS induction correlates well with the ability of the spacers to kill the cells. This corroborates the idea that efficient cleavage of all copies of the chromosome is responsible for cell death.

TABLE 1

Integrated E. coli strains.
This table shows the backbones and fragments used for integrations in the chromosome of E. coli following methods described previously (ref 35). The pOSIP backbone was removed from the chromosome using plasmid pE-FLP. Primers and templates used to generate the fragments are listed in Table 3.

| Name of the new strain | pOSIP Backbone | Fragment 1 | Fragment 2 | Integration site | Original strains | pOSIP backbone | Strain description |
|---|---|---|---|---|---|---|---|
| LC-E01 | pOSIP-KH | Mt-LigD promoter | Mt-LigD fragment | HK022 attB | MG1655, RecB- | removed | MG1655 with Mt-LigD |
| LC-E02 | pOSIP-KO | Tet-dCas9 | N/A | 186 attB | MG1655 | removed | MG1655 with inducible dCs9 |
| LC-E03 | pOSIP-KO | Tet-wtCas9 | N/A | 186 attB | MG1655 | removed | MG1655 with inducible wtCs9 |
| LC-E05 | pOSIP-KO | Mt-Ku promoter | Mt-Ku fragment | 186 attB | LC-E01 | removed | MG1655 with Mt-LigD and Mt-Ku |
| LC-E06 | pOSIP-KO | Tet-wtCas9 | N/A | 186 attB | MG1655, RecA- | removed | MG1655 (RecA-) with inducible wtCs9 |
| LC-E07 | pOSIP-KO | Tet-wtCas9 | N/A | 186 attB | N4278 | removed | MG1655 (RecB-) with inducible wtCs9 |
| LC-E08 | pOSIP-KO | Tet-wtCas9 | N/A | 186 attB | JJC443 | removed | MG1655 (LexA-) with inducible wtCs9 |

TABLE 2

CRISPR spacers used in this invention.

| CRISPR spacer name | CRISPR spacer sequence (from 5' to 3') / SEQ ID NO: | | Targeted strand | PAM |
|---|---|---|---|---|
| lacZ1 | TCACTGGCCGTCGTTTTACAACGTCGTGAC | 16 | Template strand | TGG |
| lacZ2 | CCATTACGGTCAATCCGCCGTTTGTTCCCA | 17 | Template strand | CGG |
| rpsL | TACTTTACGCAGCGCGGAGTTCGGTTTTTT | 18 | Non template strand | AGG |
| mhpR | GGAATTAATCGAAATGTTAGCCTCCCGCCC | 19 | Template strand | CGG |
| tsuB | TAAGGTCTTCGTTCAGGGCATAGACCTTAA | 20 | Non template strand | TGG |
| wcaH | TTTTCTCGCTGAGAAGCGTACCGGAGTACC | 21 | Template strand | CGG |
| irhA | ATTCCGCTGCGCAGTACCAGTGTGTTGGCG | 22 | Non template strand | AGG |
| eamB | CAGCGGTACACCTTTTGAGTTGGGCGGGGG | 23 | Template strand | CGG |
| speA | AGCAGAACGTCTGAATGTCGTTCCTCGTCT | 24 | Template strand | GGG |
| garD | CGTGGTGGGGCTGAATCATTTGTACGGTTG | 25 | Template strand | TGG |
| treF | GTACCGCGATTTACGCGCGGGGGCGGCCTC | 26 | Template strand | CGG |
| yfaP | ATTCGTGCACGTTTACGGCTGGTTCTCTCG | 27 | Template strand | TGG |
| ada | GGTGCGTTACGCGCTGGCTGATTGTGAGCT | 28 | Template strand | GGG |

The SEQ ID Nos: 16 to 28 in table 2 correspond to SEQ ID Nos: 39 to 51 of the priority application.

TABLE 3

Primers used in this invention.

| Primer Name | Primer sequences (from 5' to 3') | SEQ ID NO: | Template | Fragments generated (of primer function) |
|---|---|---|---|---|
| B299 | CATGAATTCAACTCAACAAGTCTCAGTGTGCTG | 29 | pCRISPR | pCRISPR backbone |
| LC34 | TTTAGGCGCTGCCATCTTAAGACGAAAGGGCCTCGTGATA | 30 | pCRISPR | pCRISPR backbone |
| LC35 | TTCAGCACACTGAGACTTGTTGAGTTGAATTCATGAGTATT AAGTATTGTTTTATGGCTGATA | 31 | pCas9 | TracrRNA fragment |
| LC36 | TATCACGAGGCCCTTTCGTCTTAAGATGGCAGCGCCTAAA | 32 | pCas9 | TracrRNA fragment |
| LC41 | TGCAGCGCGATCGTAATCAGGATCCCATGGTACGCGT | 33 | pCRISPR | pCRISPR backbone |
| LC42 | ACAGAACTTAATGGGCCCGAAGACGAAAGGGCCTCGT | 34 | pCRISPR | pCRISPR backbone |

TABLE 3-continued

Primers used in this invention.

| Primer Name | Primer sequences (from 5' to 3') | SEQ ID NO: | Template | Fragments generated (of primer function) |
|---|---|---|---|---|
| LC37 | TCCGCCGTTTGTTCCCACGTAGAATCCGACGGGTTGTTAC | 35 | MG1655 genomic DNA | the 2nd lacZ homologous fragment |
| LC38 | GTAACAACCCGTCGGATTCTACGTGGGAACAAACGGCGGA | 36 | MG1655 genomic DNA | the 1st lacZ homologous fragment |
| LC39 | ACGAGGCCCTTTCGTCTTCGGGCCCATTAAGTTCTGT | 37 | MG1655 genomic DNA | the 1st lacZ homologous fragment |
| LC40 | ACGCGTACCATGGGATCCTGATTACGATCGCGCTGCA | 38 | MG1655 genomic DNA | the 2nd lacZ homologous fragment |
| LC191 | GTCTAGGGCGGCGGATTTG | 39 | pDB127 | GFPmut2 fragment |
| LC192 | CGCTCTCCTGAGTAGGACAAAT | 40 | pZA31-Luc | pZA31-Luc backbone |
| LC193 | ACAATTGAATACCGATCGGCCTCGTGATACGCCTAT | 41 | pZA31-Luc | pZA31-Luc backbone |
| LC194 | ATAGGCGTATCACGAGGCCGATCGGTATTCAATTGTGCCCAA | 42 | MG1655 genomic DNA | sulA promoter fragment |
| LC195 | CAGGGGCTGGATTGATTATGAGTAAAGGAGAAGAACTTTTC | 43 | pDB127 | GFPmut2 fragment |
| LC196 | TTCTTCTCCTTTACTCATAATCAATCCAGCCCCTGTGA | 44 | MG1655 genomic DNA | sulA promoter fragment |
| LC95 | CTCCGACGCCGAACCCATACAACCTCCTTAGTACATCAAGCA | 45 | pE-FLP | Mt-LigD promoter |
| LC96 | GCAGGACGCCCGCCATAAACTGCCAGGAATTGGGGATCGGG GGGTTCCGCGCACATTT | 46 | pE-FLP | Mt-LigD promoter or Mt-Ku promoter |
| LC94 | TGCTTGATGTACTAAGGAGGTTGTATGGGTTCGGCGTCGGAG | 47 | M. tuberculosis H37Rv genomic DNA | Mt-LigD fragment |
| LC98 | AGTTTAGGTTAGGCGCCATGCATCTCGAGGCATGCCTGCATC ATTCGCGCACCACCTCA | 48 | M. tuberculosis H37Rv genomic DNA | Mt-LigD fragment |
| LC93 | CGTCCAAATGGCTCGCATACAACCTCCTTAGTACATCAAGCA | 49 | pE-FLP | Mt-Ku promoter |
| LC92 | TGCTTGATGTACTAAGGAGGTTGTATGCGAGCCATTTGGACG | 50 | M. tuberculosis H37Rv genomic DNA | Mt-Ku fragment |
| LC97 | AGTTTAGGTTAGGCGCCATGCATCTCGAGGCATGCCTGCATC ACGGAGGCGTTGGGAC | 51 | M. tuberculosis H37Rv genomic DNA | Mt-Ku fragment |

TABLE 3-continued

Primers used in this invention.

| Primer Name | Primer sequences (from 5' to 3') | SEQ ID NO: | Template | Fragments generated (of primer function) |
|---|---|---|---|---|
| LC100 | GCAGGACGCCCGCCATAAACTGCCAGGAATTGGGGATCGGTTAAGACCCACTTTCACATTTAAG | 52 | pdCas9-bacteria or pwtCas9-bacteria | Tet-dCas9 or Tet-Cas9 fragment |
| LC101 | AGTTTAGGTTAGGCGCCATGCATCTCGAGGCATGCCTGCATATAAACGCAGAAAGGCCC | 53 | pdCas9-bacteria or pwtCas9-bacteria | Tet-dCas9 or Tet-Cas9 fragment |
| LC33 | GACTGGAAAGCGGGCAGT | 54 | | Sequencing |
| LC47 | CGCACGATAGAGATTCGGGA | 55 | | Sequencing |
| LC80 | TCAGGCGGGATGAAGATGAT | 56 | | PCR verification |
| LC153 | GCTGGGATACGCTGGTGTTTA | 57 | | PCR verification |
| LC154 | CACAGCGCAAGGACGTTGA | 58 | | PCR verification |
| LC155 | ACACAACATGACGGGCTT | 59 | | PCR verification |

The SEQ ID Nos: 29 to 59 in table 3 correspond to SEQ ID Nos: 52 to 82 of the priority application.

The ability of Cas9 to kill bacteria when directed to cut in their chromosome has been used as a counter-selection tool for the purpose of gene editing and for the development of sequence-specific antimicrobials [7, 14, 15]. However, the mechanism of Cas9-mediated cell death has so far remained unclear. Here the inventors shown that not all targets are equal and *E. coli* can survive active targeting at some positions. Cas9-induced breaks activate the SOS response and can be repaired by the HDR pathway. This enables *E. coli* to tolerate the presence of weak self-targeting CRISPR systems. Other targets can be cleaved efficiently leading to the introduction of DSB in all copies of the chromosome simultaneously. In the absence of a template for HDR, extensive recession of the DNA ends by RecBCD and other nucleases is likely the cause of cell death.

Variations in the efficiency of Cas9 cleavage between different targets have been reported previously [10,26,27]. The ability to predict the efficacy of guide RNAs is of prime importance for all applications of Cas9 technologies. High-throughput screens of sgRNA libraries in human or mouse cells have allowed identifying good targets[26,28], and were used to build predictive models for the design of highly active sgRNAs. However, the most recent model from Jong and colleagues [28] gave very poor prediction for the activity of the 13 targets that were used in our study. This could stem from differences in the requirements for efficient Cas9 targeting between mammalian cells and *E. coli*, as well as the fact that these screens were performed using sgRNAs instead of the dual crRNA and tracrRNA system. In particular some features that influence the expression of the sgRNA, loading of the sgRNA on Cas9, or the accessibility of the target DNA are likely not generalizable to present system. This highlights the necessity to perform similar screens in bacteria. The inventors demonstrate here that the level of SOS induction can be used to estimate the efficiency of Cas9 interference in *E. coli*, with good targets showing a more pronounced SOS response (FIG. 3B). This might be useful to score candidate targets and could also be used in combination with Fluorescence-Activated Cell Sorting (FACS) to screen for highly active guides in a library. A better knowledge of what makes a good CRISPR target will be critical for the development of reliable genome engineering tools as well as CRISPR antimicrobials.

Interestingly cell death is not the only possible outcome of efficient Cas9 cleavage in the chromosome of *E. coli*. Large deletions can be introduced through recombination between distant homologous sequences. This is consistent with rearrangements observed in a previous study where a mRFP gene integrated in the genome was targeted by Cas9 [20].

Figure 6:
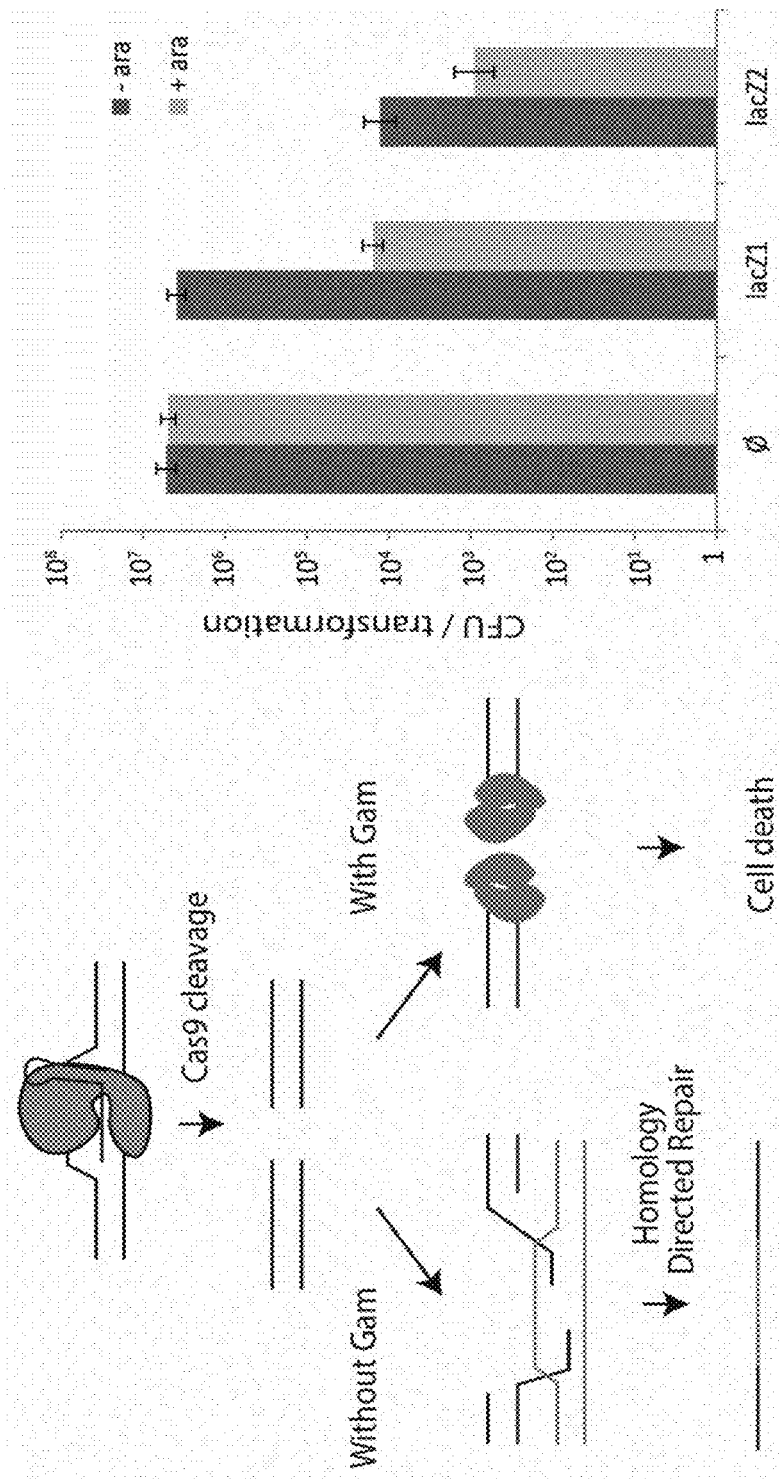
FIGS. 6A to 6B: Gam can block DNA repair of double strand breaks introduced by Cas9. A) Representation of possible outcomes of Cas9 cleavage in the presence or absence of Gam. Upon targeting by weak spacers or in any other situation where a homologous template molecule is present in the cell, Cas9 breaks can be repaired through homology directed repair (HDR). In *E. coli* this can be achieved by the recBCD homologous recombination pathway. In the presence of Gam, DNA ends are protected from the action of recombinases. The presence of unrepaired DNA in the cell will ultimately lead to cell death. B) The pCas9 plasmid carrying either an empty CRISPR array, the lacZ1 spacer or the lacZ2 spacer was transformed in cells containing the pLC13 plasmid which carries the Mu gam gene under the control of a pBAD promoter. Transformants were plated on selective medium either with or without arabinose (−ara/+ara). The number of colony forming units is reported. Error bars represent the standard deviation of three independent assays.

The pCas9 plasmid carrying either an empty CRISPR array, the lacZ1 spacer or the lacZ2 spacer was transformed in cells containing the pLC13 plasmid which carries the Mu gam gene under the control of a pBAD promoter. Transformants were plated on selective medium either with or without arabinose (−ara/+ara). The results are shown in FIG. 6A-B. Upon Mu-Gam induction with arabinose, Cas9 killing efficiency using the weak lacZ1 spacer is increased more than 1000x. A more moderated increase in killing efficiency is also observed when targeting with the stronger lacZ2 spacer.

Example 10

Figure 7:
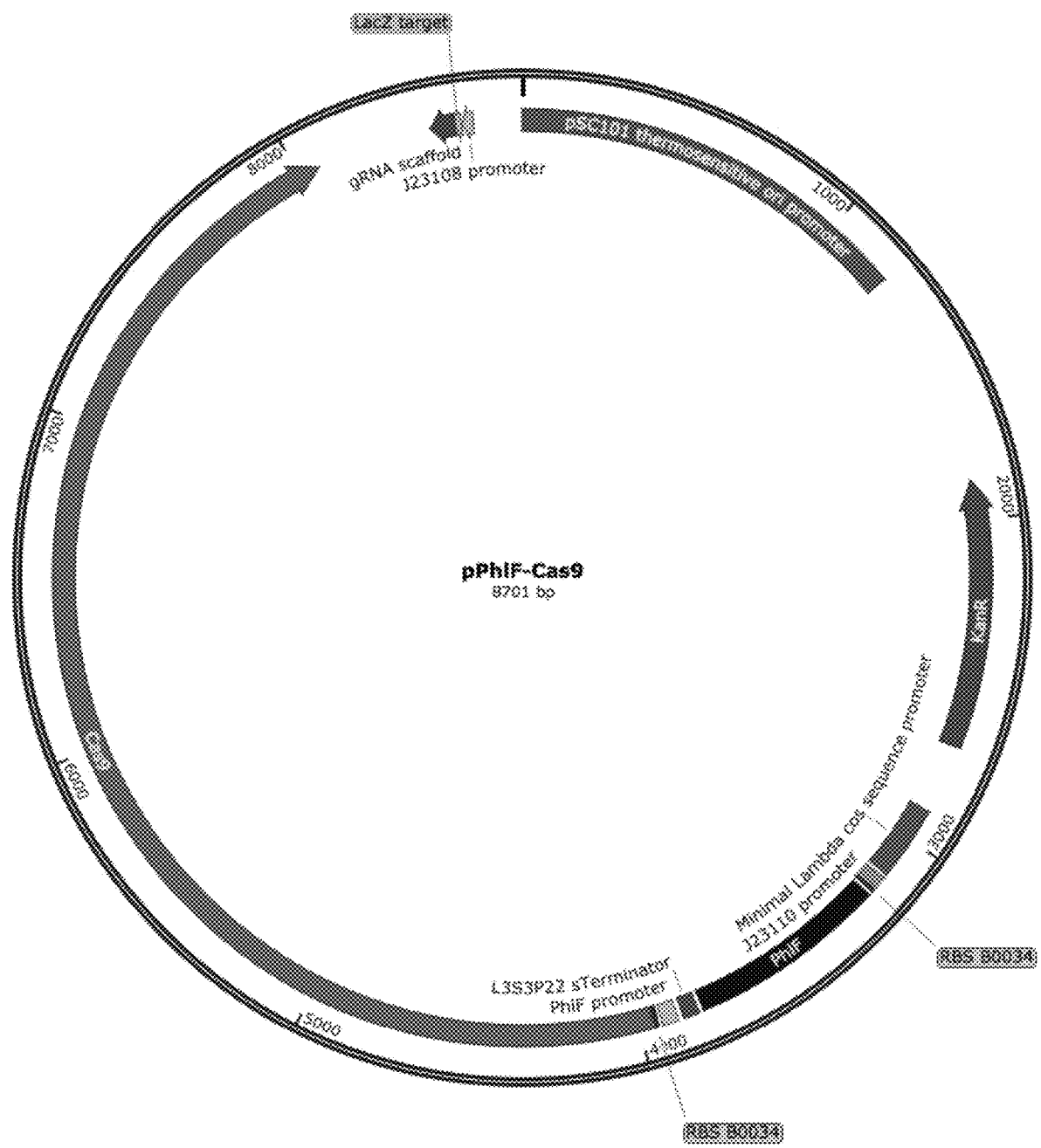
FIG. 7: pPhlF-Cas9 plasmid map (SEQ ID NO: 68)

The inventors have developed an inducible Cas9-sgRNA system targeting the *E. coli* chromosome with very low leakiness and high cleaving efficiency. This setup allows for a 3-log difference in cell survival in the presence of inducer with virtually no difference in the amount of viable cells in its absence. In this architecture, Cas9 expression is under the control of the PhlF repressor (1), which can be activated upon addition of a small molecule, 2,4-diacetylphloroglucinol (DAPG). The transcription of the sgRNA, which targets a genomic sequence at the 5' end of the lacZ gene, is under the control of a synthetic constitutive promoter, PJ23108. Both elements are encoded in a low copy thermosensitive origin of replication, pSC101* (FIG. 7).

The inventors show that the co-expression of Mu-Gam, a viral protein that inhibits the host's homologous recombination machinery, can serve as an adjuvant to increase Cas9-mediated killing when targeting the bacterial chromosome. The effects can increase the efficiency of Cas9-mediated cell death by 15-200 fold. These results have been demonstrated for different crRNA sequences, especially when they are not optimized. This system implements a different architecture, relying on the tightly regulated expression of Cas9 as well as a constitutively transcribed sgRNA that targets a genomic sequence. The inventors assessed if the addition of Mu- and Lambda-Gam proteins to this system improves the efficiency of Cas9-mediated killing of target bacteria.

This approach is important, since there exist a variety of conditions where cleavage may be suboptimal as compared to in vitro assays. Even though laboratory experiments show that invention's current Cas9-sgRNA design allows for a 3-log killing upon induction, the conditions may vary in other setups; for instance, natural SNPs of the target sequence or escape mechanisms due to mutations in the targeted sequence can reduce the efficiency of Cas9 cleavage; non-optimally designed sgRNAs or targeting a heterogeneous population; protein expression inducers may not be efficiently administered or show toxicity in different setups, such as in vivo models, reducing expression levels of Cas9 and hence efficiency; and finally, the physiological state of the cell may influence the expression levels and cleavage efficiency of Cas9: in a laboratory setup, cells are typically maintained in the log growth phase, while in many other situations they may enter different growth regimes (such as stationary phase). For all these situations, an adjuvant for Cas9 activity will be beneficial to achieve the desired effects.

A) Use Non-Optimally Designed sgRNA Sequences to Reduce Cas9 Efficiency Even in the Presence of Maximal Amounts of Inducer.

It has been shown that the Cas9-sgRNA machinery can tolerate mismatches at the 5' end of the sgRNA in the targeted genomic sequence, although with reduced cleavage efficiency. To do this, the inventors constructed variants of the plasmid pPhlF-Cas9 possessing sequential mutations in the first 5 nucleotides at the 5' end of the sgRNA. The cleavage efficiency of these variants was assessed in LB-agar plates by the droplet method at different concentrations of DAPG. These plasmid variants were used in subsequent experiments to assess the effect of the Mu-Gam and the Lambda-Gam proteins in suboptimal cleavage conditions caused by non-optimized sgRNA sequences.

B) Optimize Mu- and Lambda-Gam Expression Levels.

Figure 8:
FIG. 8: pBAD-MuGam plasmid map (SEQ ID NO: 69)
Figure 9:
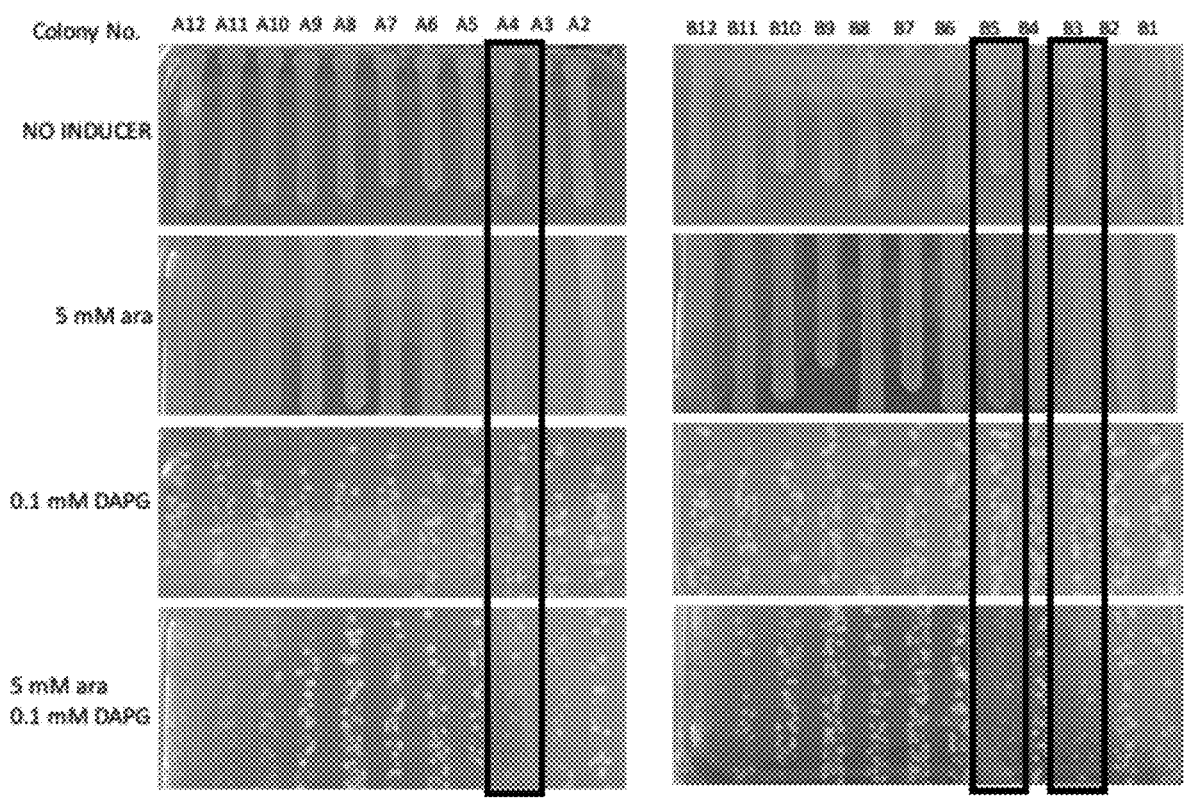
FIG. 9: MuGam RBS library (selection). Black squares mark selected clones for further characterization. The RBS sequence upstream of the mu-gam gene in pBAD-MuGam was modified by running an iPCR reaction on the plasmid followed by a one-pot phosphorylation-ligation reaction. The religated plasmids were co-transformed into MG1655 cells containing the pPhlF-Cas9 plasmid, plated in LB-agar supplemented with 50 μg/mL kanamycin, 100 μg/mL chloramphenicol, 0.1 mM IPTG and 40 μg/mL X-gal and grown for 20 hours at 30° C. Next, 95 single colonies were selected and grown in 500 μL LB supplemented with 50 μg/mL kanamycin and 100 μg/mL chloramphenicol in 96-deep-well plates for 18 hours at 1000 rpm at 30° C. Next day, each culture was diluted 1:100 in distilled water. The cells were assayed in four conditions: plates without inducer; plates that contained 5 mM arabinose; plates that contained 0.1 mM DAPG; and plates that contained both 5 mM arabinose and 0.1 mM DAPG. This experiment allows for the comparison of cell morphology and/or toxicity in the presence of Mu-Gam only and its effects when Cas9-sgRNA is co-expressed. Highlighted RBS library hits (black rectangles) shows dying colonies upon induction of Cas9 and Mu-Gam.

The inventors verified that a defined expression level exists for the Mu/Lambda-Gam proteins to act as adjuvants of Cas9-mediated killing while proving non-toxic upon expression on their own. In an initial step to facilitate the characterization and further engineering of the system, several RBS sequences for the Mu-Gam protein were screened in a separate plasmid, pBAD-MuGam (SEQ ID NO: 69):

The RBS sequence upstream of the mu-gam gene in pBAD-MuGam (FIG. 8) was modified by running an iPCR reaction on the plasmid followed by a one-pot phosphorylation-ligation reaction. The religated plasmids were co-transformed into MG1655 cells containing the pPhlF-Cas9 plasmid, plated in LB-agar supplemented with 50 µg/mL kanamycin, 100 lag/mL chloramphenicol, 0.1 mM IPTG and 40 µg/mL X-gal and grown for 20 hours at 30° C. Next, 95 single colonies were selected and grown in 500 µL LB supplemented with 50 µg/mL kanamycin and 100 µg/mL chloramphenicol in 96-deep-well plates for 18 hours at 1000 rpm at 30° C. Next day, each culture was diluted 1:100 in distilled water and assayed by the droplet method in LB agar plates. Briefly, individual 8 µL droplets were plated onto the surface of LB-agar plates supplemented with 50 µg/mL kanamycin, 25 µg/mL chloramphenicol, 0.1 mM IPTG and 40 µg/mL X-gal. The plates were then gently turned in a vertical position to allow the droplets to slide down the surface of LB-agar and incubated o/n at 30° C. for 18 hours. The cells were assayed in four conditions: plates without inducer; plates that contained 5 mM arabinose; plates that contained 0.1 mM DAPG; and plates that contained both 5 mM arabinose and 0.1 mM DAPG. This experiment allows for the comparison of cell morphology and/or toxicity in the presence of Mu-Gam only and its effects when Cas9-sgRNA is co-expressed (FIG. 9).

The initial RBS screening yielded several clones that had altered cell morphology and appearance (smaller and translucent) in the presence of both Mu-Gam and Cas9-sgRNA while showing a normal aspect in the presence of Mu-Gam only. These clones were also verified for Cas9-sgRNA activity and achieved similar killing efficiencies as the pPhlF-Cas9 system alone.

Figure 10:
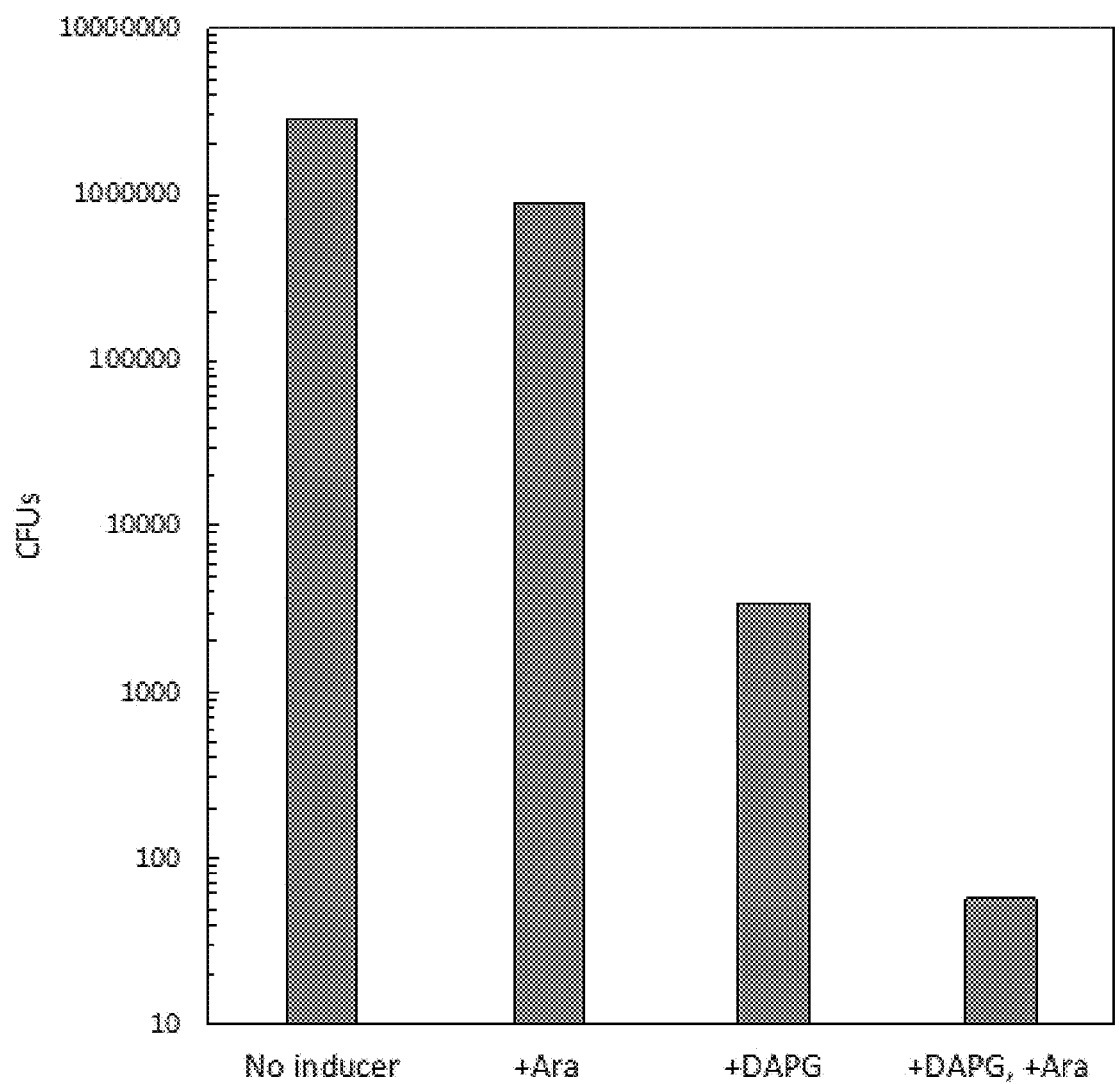
FIG. 10: CFUs of droplet dilutions of selected MuGam RBS clone. One clone were selected for its potential Mu_Gam adjuvant activity and a more detailed characterization was performed on LB-agar plates in the particular conditions (no inducer; plus arabinose; plus DAPG; plus DAPG and arabinose). After an additional 24-hour incubation period CFUs were counted. For the "+DAPG, +Ara" dataset, colonies were directly counted from the undiluted droplet. For the "+DAPG" dataset, colonies were counted at $10^{-2}$ and $10^{-3}$ dilutions, the dilution factor calculated and the number of CFUs in the undiluted droplet estimated. For "No inducer" and "+Ara" conditions, the number of CFUs in the undiluted droplet was estimated by counting the number of colonies in the $10^{-5}$ and $10^{-6}$ dilutions and calculation the dilution factor.
Figure 11:
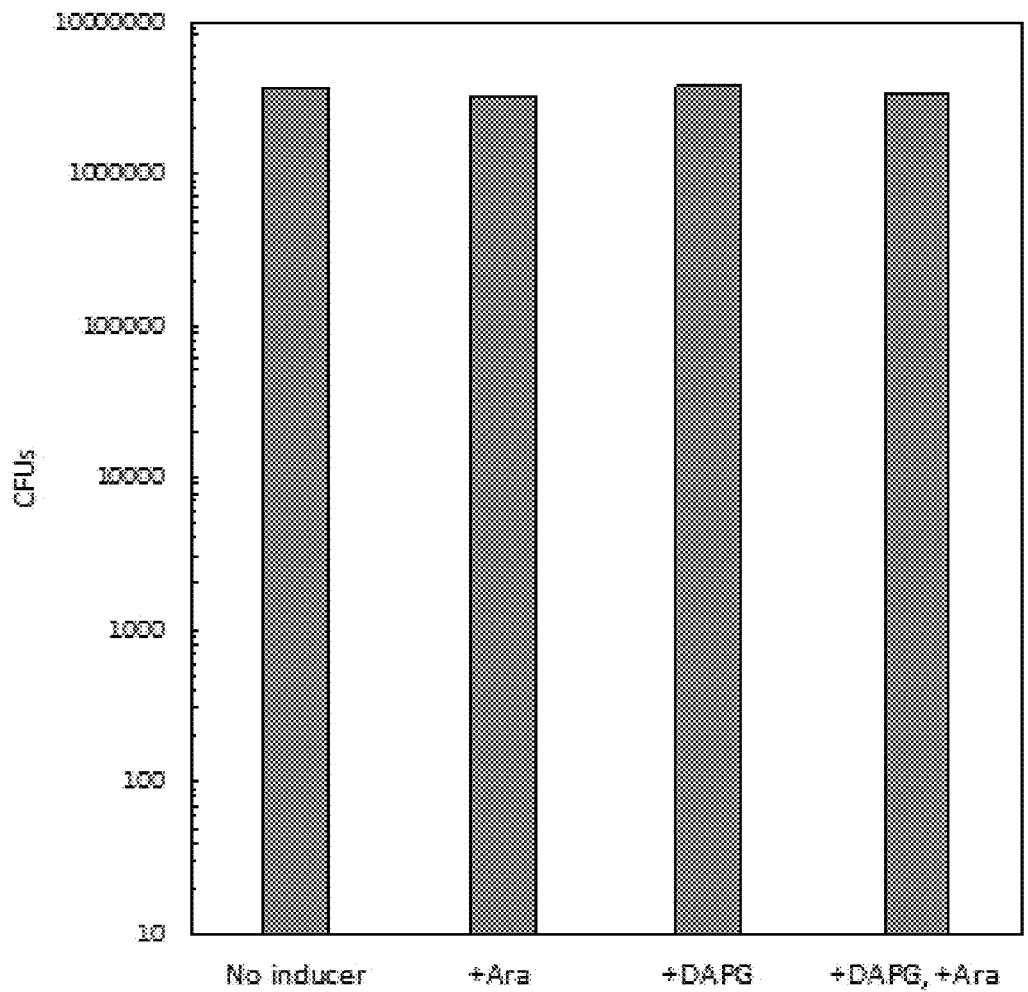
FIG. 11: Activity of MuGam in a non-targeted sgRNA background. Cells containing pBAD-MuGam hit were co-transformed with a pPhlF-Cas9 variant with a non-targeted sgRNA sequence. Cells were analyzed by the droplet method as explained in (A) and CFUs counted. To estimate the CFUs in the undiluted droplet, CFUs were counted at the $10^{-6}$ and $10^{-5}$ dilutions, the dilution factor calculated and the number of CFUs in the undiluted droplet calculated. No toxicity of MuGam can be observed in the absence of Cas9 targeting in the chromosome.
Figure 12:
FIG. 12: pBAD-LambdaGam plasmid map (SEQ ID NO: 72).

The inventors selected one clone based on its potential Mu-Gam adjuvant activity and performed a more detailed characterization on LB-agar plates in the same four conditions described above (no inducer; plus arabinose; plus DAPG; plus DAPG and arabinose). After a 24-hour incubation period, massive cell death occurred, which was especially pronounced in cells that were plated at a higher density, as can be seen in FIG. 10. For the "+DAPG, +Ara" dataset, colonies were directly counted from the undiluted droplet. For the "+DAPG" dataset, colonies were counted at $10^{-2}$ and $10^{-3}$ dilutions, the dilution factor calculated and the number of CFUs in the undiluted droplet estimated. For "No inducer" and "+Ara" conditions, the number of CFUs in the uniduluted droplet was estimated by counting the number of colonies in the $10^{-5}$ and $10^{-6}$ dilutions and the dilution factor calculated. Moreover, if the same experiment is performed in cells containing pBAD-MuGam and a pPhlF-Cas9 variant with a sgRNA not targeting the genome, no cell death is seen for any conditions (FIG. 11). Cells containing pBAD-MuGam hit were co-transformed with a pPhlF-Cas9 variant with a non-targeted sgRNA sequence. Cells were analyzed by the droplet method as explained in (A) and CFUs counted. To estimate the CFUs in the undiluted droplet, CFUs were counted at the $10^{-6}$ and $10^{-5}$ dilutions, the dilution factor calculated and the number of CFUs in the undiluted droplet calculated. These results indicate that expression of Gam together with a targeted Cas9-sgRNA system leads to improved cell killing, in an assay where Cas9-mediate killing is already very efficient in itself. This assay was also performed under sub-optimal targeting conditions through the introduction of mismatches between the guide RNA and the target. Additionally, the same experiments can be performed with Lambda-Gam by constructing the plasmid pBAD-LambdaGam (FIG. 12):

C) Construction of an Integrated Architecture Encoding Cas9-sgRNA and Mu/Lambda-Gam.

Both Cas9-sgRNA and Mu/Lambda-Gam inducible cassettes can be integrated in the same plasmid containing a low copy origin of replication (pSC101) as well as a cos site.

Figure 13:
FIG. 13: pCas9-MuGam/LambdaGam plasmid map (SEQ ID NO: 71/SEQ ID NO: 72).

This architecture possesses two advantages: a low copy origin of replication allows for a wider tunable range of RBS strengths and reduced leakiness, hence increasing the expression space for a given protein; and also offers a platform for generating packaged cosmids to transduce the genetic program into a target strain. The integrated vectors, pCas9-MuGam and pCas9-LambdaGam, are shown on FIG. 13.

The expression levels of the Mu/Lambda-Gam proteins was tuned and characterized as described in (B) in MG1655 using transformed cells as a testbed.

D) Packaging of pCas9-MuGam and pCas9-LambdaGam into Cosmid Particles.

Once optimal expression levels for Mu-Gam and Lambda-Gam have been found as described in (C), the inventors performed transduction experiments with the packaged cosmid particles. To do this, the optimized pCas-MuGam/Lambda-Gam plasmids was transformed in CY2120 cells, plated on LB-agar plus 50 µg/mL kanamycin and incubated o/n at 30° C. A single colony was picked and grown in liquid LB to an OD600 of 0.5 at 30° C. To induce the packaging, the culture was heat-shocked at 42° C. for 20 minutes and subsequently incubated at 37° C. for 4 hours. Cells were harvested, resuspended in lambda dilution buffer and lysed by adding chloroform. The packaged cosmid was isolated from the supernatant by centrifugation to pellet cell debris. The titer of the packaged cosmid was then determined by transduction of E. coli DH5-alpha.

Both pPhlF-Cas9 and pCas9-MuGam or pCas9-LambdaGam cosmids were generated and assayed in parallel to assess the efficiency of Cas9-mediated cell death and the effects of the addition of one of the viral proteins.

E) Pathogenic E. coli Strains.

Finally, the same tests are performed in pathogenic E. coli strains The sgRNA variant used in all experiments described above also targets the genome of E. coli LF82, a known human pathogen. The efficiency of the engineered cosmids was assessed in this bacterial strain and can be potentially expanded to many other known human pathogens.

REFERENCES

1. Sorek, R., Lawrence, C. M. & Wiedenheft, B. CRISPR-mediated adaptive immune systems in bacteria and archaea. Annual review of biochemistry 82, 237-266, doi:10.1146/annurev-biochem-072911-172315 (2013).
2. Hsu, P. D., Lander, E. S. & Zhang, F. Development and applications of CRISPR-Cas9 for genome engineering. Cell 157, 1262-1278, doi:10.1016/j.cell.2014.05.010 (2014).
3. Deltcheva, E. et al. CRISPR RNA maturation by trans-encoded small RNA and host factor RNase III. Nature 471, 602-607, doi:10.1038/nature09886 (2011).
4. Jinek, M. et al. A programmable dual-RNA-guided DNA endonuclease in adaptive bacterial immunity. Science 337, 816-821, doi:10.1126/science.1225829 (2012).
5. Sternberg, S. H., Redding, S., Jinek, M., Greene, E. C. & Doudna, J. A. DNA interrogation by the CRISPR RNA-guided endonuclease Cas9. Nature 507, 62-67, doi:10.1038/nature13011 (2014).
6. Jinek, M. et al. Structures of Cas9 endonucleases reveal RNA-mediated conformational activation. Science 343, 1247997, doi:10.1126/science.1247997 (2014).
7. Jiang, W., Bikard, D., Cox, D., Zhang, F. & Marraffini, L. A. RNA-guided editing of bacterial genomes using CRISPR-Cas systems. Nature biotechnology 31, 233-239, doi:10.1038/nbt.2508 (2013).
8. Oh, J. H. & van Pijkeren, J. P. CRISPR-Cas9-assisted recombineering in Lactobacillus reuteri. Nucleic acids research 42, e131, doi:10.1093/nar/gku623 (2014).
9. Cobb, R. E., Wang, Y. & Zhao, H. High-Efficiency Multiplex Genome Editing of Streptomyces Species Using an Engineered CRISPR/Cas System. ACS synthetic biology, doi:10.1021/sb500351f (2014).
10. Cong, L. et al. Multiplex genome engineering using CRISPR/Cas systems. Science 339, 819-823, doi: 10.1126/science.1231143 (2013).
11. Mali, P. et al. RNA-guided human genome engineering via Cas9. Science 339, 823-826, doi:10.1126/science.1232033 (2013).
12. Shuman, S. & Glickman, M. S. Bacterial DNA repair by non-homologous end joining. Nature reviews. Microbiology 5, 852-861, doi:10.1038/nrmicro1768 (2007).
13. Bowater, R. & Doherty, A. J. Making ends meet: repairing breaks in bacterial DNA by non-homologous end-joining. PLoS genetics 2, e8, doi:10.1371/journal.pgen.0020008 (2006).
14. Citorik, R. J., Mimee, M. & Lu, T. K. Sequence-specific antimicrobials using efficiently delivered RNA-guided nucleases. Nature biotechnology, doi:10.1038/nbt.3011 (2014).
15. Bikard, D. et al. Exploiting CRISPR-Cas nucleases to produce sequence-specific antimicrobials. Nature biotechnology, doi:10.1038/nbt.3043 (2014).
16. Bikard, D., Hatoum-Aslan, A., Mucida, D. & Marraffini, L. A. CRISPR interference can prevent natural transformation and virulence acquisition during in vivo bacterial infection. Cell host & microbe 12, 177-186, doi:10.1016/j.chom.2012.06.003 (2012).
17. Edgar, R. & Qimron, U. The Escherichia coli CRISPR system protects from lambda lysogenization, lysogens, and prophage induction. Journal of bacteriology 192, 6291-6294, doi:10.1128/JB.00644-10 (2010).
18. Stern, A., Keren, L., Wurtzel, O., Amitai, G. & Sorek, R. Self-targeting by CRISPR: gene regulation or autoimmunity? Trends in genetics: TIG 26, 335-340, doi:10.1016/j.tig.2010.05.008 (2010).
19. Gomaa, A. A. et al. Programmable removal of bacterial strains by use of genome-targeting CRISPR-Cas systems. mBio 5, e00928-00913, doi:10.1128/mBio.00928-13 (2014).
20. Qi, L. S. et al. Repurposing CRISPR as an RNA-guided platform for sequence-specific control of gene expression. Cell 152, 1173-1183, doi:10.1016/j.cell.2013.02.022 (2013).
21. Bikard, D. et al. Programmable repression and activation of bacterial gene expression using an engineered CRISPR-Cas system. Nucleic acids research 41, 7429-7437, doi:10.1093/nar/gkt520 (2013).
22. Ton-Hoang, B. et al. Structuring the bacterial genome: Y1-transposases associated with REP-BIME sequences. Nucleic acids research 40, 3596-3609, doi:10.1093/nar/gkr1198 (2012).
23. Kofoid, E., Bergthorsson, U., Slechta, E. S. & Roth, J. R. Formation of an F' plasmid by recombination between imperfectly repeated chromosomal Rep sequences: a closer look at an old friend (F'(128) pro lac). Journal of bacteriology 185, 660-663 (2003).
24. Malyarchuk, S. et al. Expression of Mycobacterium tuberculosis Ku and Ligase D in Escherichia coli results in RecA and RecB-independent DNA end-joining at regions of microhomology. DNA repair 6, 1413-1424, doi:10.1016/j.dnarep.2007.04.004 (2007).

25. Chayot, R., Montagne, B., Mazel, D. & Ricchetti, M. An end-joining repair mechanism in *Escherichia coli*. *Proceedings of the National Academy of Sciences of the United States of America* 107, 2141-2146, doi:10.1073/pnas.0906355107 (2010).
26. Wang, T., Wei, J. J., Sabatini, D. M. & Lander, E. S. Genetic screens in human cells using the CRISPR-Cas9 system. *Science* 343, 80-84, doi:10.1126/science.1246981 (2014).
27. Shalem, O. et al. Genome-scale CRISPR-Cas9 knockout screening in human cells. *Science* 343, 84-87, doi: 10.1126/science.1247005 (2014).
28. Doench, J. G. et al. Rational design of highly active sgRNAs for CRISPR-Cas9-mediated gene inactivation. *Nature biotechnology* 32, 1262-1267, doi:10.1038/nbt.3026 (2014).
29. Meddows, T. R., Savory, A. P., Grove, J. I., Moore, T. & Lloyd, R. G. RecN protein and transcription factor DksA combine to promote faithful recombinational repair of DNA double-strand breaks. *Molecular microbiology* 57, 97-110, doi:10.1111/j.1365-2958.2005.04677.x (2005).
30. Bierne, H., Seigneur, M., Ehrlich, S. D. & Michel, B. uvrD mutations enhance tandem repeat deletion in the *Escherichia coli* chromosome via SOS induction of the RecF recombination pathway. *Molecular microbiology* 26, 557-567 (1997).
31. Gibson, D. G. et al. Enzymatic assembly of DNA molecules up to several hundred kilobases. *Nature methods* 6, 343-345, doi:10.1038/nmeth.1318 (2009).
32. Lutz, R. & Bujard, H. Independent and tight regulation of transcriptional units in *Escherichia coli* via the LacR/O, the TetR/O and AraC/I1-I2 regulatory elements. *Nucleic acids research* 25, 1203-1210 (1997).
33. Cormack, B. P., Valdivia, R. H. & Falkow, S. FACS-optimized mutants of the green fluorescent protein (GFP). *Gene* 173, 33-38 (1996).
34. Cole, S. T. Characterisation of the promoter for the LexA regulated sulA gene of *Escherichia coli*. *Molecular & general genetics: MGG* 189, 400-404 (1983).
35. St-Pierre, F. et al. One-step cloning and chromosomal integration of DNA. *ACS synthetic biology* 2, 537-541, doi:10.1021/sb400021j (2013).
36. Makarova, K. S., D. H. Haft, R. Barrangou, S. J. Brouns, E. Charpentier, P. Horvath, S. Moineau, F. J. Mojica, Y. I. Wolf, A. F. Yakunin, J. van der Oost and E. V. Koonin (2011). "Evolution and classification of the CRISPR-Cas systems." *Nat Rev Microbiol* 9 (6): 467-477.
37. Pennisi, E. (2013). "The CRISPR craze." Science 341 (6148): 833-836.
38. Weller G. R. (2002) Science, 297, pp. 1686-1689
39. Ahu H. and Shuman S. (2005) J Biol Chem, 280, pp 25973-25981
40. Cong C. et al (2005) Nat Struct. Mol. Biol., 12 pp 304-312
41. Datsenko K. A. and Wanner B. L. (PNAS Jun. 6, 2000, vol 97, no. 12 pp 6640-6645).
42. Fernandez de Henestrosa A. R. (2002) Molecular Microbiology Vol 35, Issue 6, pages 1560-1572
43. Murphy, J Bacteriol. 1993 March; 175(6): 1756-1766.
44. di Fagagna, F. D., et al., The Gam protein of bacteriophage Mu is an orthologue of eukaryotic Ku. Embo Reports, 2003. 4(1): p. 47-52.
45. Akroyd, J. and N. Symonds, Localization of the Gam Gene of Bacteriophage-Mu and Characterization of the Gene-Product. Gene, 1986. 49(2): p. 273-282.
46. Shee, C., et al., Engineered proteins detect spontaneous DNA breakage in human and bacterial cells. Elife, 2013, 2.
47. (Guzman et al., J. Bacteriology 177(14): 4121-4130, 1995).

The invention claimed is:

1. A method for killing a bacterium comprising contacting the bacterium with at least one recombinant phagemid(s) or plasmid(s), wherein the recombinant phagemid(s) or plasmid(s) encodes:
   an endonuclease that creates a double-stranded break (DSB) in the chromosomal or extrachromosomal DNA of the bacterium, and
   an exogenous protein that inhibits DSB repair selected from the group consisting of a Mu phage Gam protein, a lambda phage Gam protein and a phage T7 gp5.9 protein.

2. The method of claim 1, wherein the exogenous protein is encoded by the same vector as the endonuclease or by a separate vector.

3. The method of claim 1, wherein the endonuclease specifically cleaves the chromosomal or extrachromosomal DNA of the bacterium at less than 2, 3, 4, 5, 6, 7, 8, 9, or 10 different sites.

4. The method of claim 1, wherein the at least one recombinant phagemid(s) is selected from the group consisting of M13, lambda, p22, T7, Mu, T4, PBSX, P1Puna-like, P2, I3, Bcep 1, Bcep 43, Bcep 78, T5, phi, C2, L5, HK97, N15, T3, P37, MS2, Qβ, Phi X 174, T2, T12, R17, G4, Enterobacteria phage P2, P4, N4, Pseudomonas phage φ6, φ29 and 186.

5. The method of claim 1, wherein the bacterium comprises a recBCD homologous repair pathway or addAB system.

6. The method of claim 1, wherein the bacterium is selected from the group consisting of *Enterobacter*, Streptococci, Staphylococci, Enterococci, *Salmonella*, *Pseudomonas* and *Mycobacterium*.

7. The method of claim 1, wherein the recombinant phagemid(s) or plasmid(s) encode(s) an endonuclease that creates a double-stranded break (DSB) in an antibiotic resistance gene encoded by the bacterium.

8. A phagemid or plasmid vector encoding an endonuclease and an exogenous protein inhibiting DSB repair, wherein said phagemid or plasmid vector encodes:
- an endonuclease that creates a double-stranded break (DSB) in the chromosomal or extrachromosomal DNA of a bacterium, and
- an exogenous protein that inhibits DSB repair selected from the group consisting of a Mu phage Gam protein, a lambda phage Gam protein and a phage T7 gp5.9 protein.

9. The phagemid or plasmid vector of claim 8, wherein the recombinant phagemid(s) is selected from the group comprising M13, lambda, p22, T7, Mu, T4, PBSX, P1Puna-like, P2, I3, Bcep 1, Bcep 43, Bcep 78, T5, phi, C2, L5, HK97, N15, T3, P37, MS2, Qβ, Phi X 174, T2, T12, R17, G4, Enterobacteria phage P2, P4, N4, Pseudomonas phage φ6, φ29 and 186.

10. The phagemid or plasmid vector of claim 8, wherein the phagemid vector is derived from a P1 bacteriophage.

11. The phagemid or plasmid vector of claim 8, wherein the phagemid vector is derived from a λ bacteriophage.

12. A method of treating a disease due to bacterium infection, comprising administering a composition comprising a phagemid or plasmid vector according to claim 8 and a pharmaceutically acceptable vehicle to a subject in need thereof.

13. A pharmaceutical composition comprising a phagemid or plasmid vector encoding an endonuclease that creates a double-stranded break (DSB) in the chromosomal or extrachromosomal DNA of a bacterium, and an exogenous protein inhibiting DSB repair or a vector encoding an exogenous protein inhibiting DSB repair wherein said exogenous protein is selected from the group consisting of a Mu phage Gam protein, a lambda phage Gam protein and a phage T7 gp5.9 protein, and a pharmaceutically acceptable vehicle.

14. The pharmaceutical composition of claim 13 further comprising an antibiotic.

15. The pharmaceutical composition of claim 13 containing a phagemid or plasmid vector encoding said endonuclease and a vector encoding said exogenous protein inhibiting DSB repair.

16. The pharmaceutical composition of claim 13, wherein said exogenous protein is encoded by the same vector as said endonuclease.

17. The method of claim 1, wherein the endonuclease is a Zinc Finger Nuclease or a Transcription Activator-Like Effector Nuclease.

18. The phagemid or plasmid vector of claim 8, wherein the endonuclease is a Zinc Finger Nuclease or a Transcription Activator-Like Effector Nuclease.

* * * * *